US012747424B2

(12) United States Patent
Ng et al.

(10) Patent No.: US 12,747,424 B2
(45) Date of Patent: Sep. 29, 2026

(54) HAEMATOPOIETIC STEM/PROGENITOR CELLS

(71) Applicant: MURDOCH CHILDRENS RESEARCH INSTITUTE, Parkville (AU)

(72) Inventors: Elizabeth Ng, Parkville (AU); Edouard Stanley, Ascot Vale (AU); Andrew Elefanty, Surrey Hills (AU)

(73) Assignee: MURDOCH CHILDRENS RESEARCH INSTITUTE, Parkville (AU)

( * ) Notice: Subject to any disclaimer, the term of this patent is extended or adjusted under 35 U.S.C. 154(b) by 69 days.

(21) Appl. No.: 18/045,296

(22) Filed: Oct. 10, 2022

(65) Prior Publication Data

US 2023/0323303 A1 Oct. 12, 2023

Related U.S. Application Data

(63) Continuation of application No. 16/300,490, filed as application No. PCT/AU2017/050440 on May 12, 2017, now abandoned.

(30) Foreign Application Priority Data

May 13, 2016 (AU) ................................ 2016901785

(51) Int. Cl.

| | |
|---|---|
| ***C12N 5/0789*** | (2010.01) |
| ***A61K 35/28*** | (2015.01) |
| ***A61P 35/02*** | (2006.01) |
| *A61K 35/12* | (2015.01) |

(52) U.S. Cl.

CPC ............ *C12N 5/0647* (2013.01); *A61K 35/28* (2013.01); *A61P 35/02* (2018.01); *A61K 2035/124* (2013.01); *C12N 2501/105* (2013.01); *C12N 2501/115* (2013.01); *C12N 2501/125* (2013.01); *C12N 2501/14* (2013.01); *C12N 2501/145* (2013.01); *C12N 2501/155* (2013.01); *C12N 2501/16* (2013.01); *C12N 2501/165* (2013.01); *C12N 2501/2303* (2013.01); *C12N 2501/2306* (2013.01); *C12N 2501/26* (2013.01); *C12N 2501/33* (2013.01); *C12N 2501/415* (2013.01); *C12N 2501/999* (2013.01); *C12N 2506/02* (2013.01); *C12N 2506/45* (2013.01)

(58) Field of Classification Search

CPC ............ C12N 5/0647; C12N 2501/105; C12N 2501/115; C12N 2501/125; C12N 2501/14; C12N 2501/145; C12N 2501/15; C12N 2501/16; C12N 2501/165; C12N 2501/2303; C12N 2501/26; C12N 2501/415; A61K 35/28

See application file for complete search history.

(56) References Cited

U.S. PATENT DOCUMENTS

2008/0159994 A1* 7/2008 Mantalaris ................ A61P 1/02 435/363
2016/0137981 A1 5/2016 Yamanaka et al.
2019/0119643 A1 4/2019 Daley et al.
2019/0144828 A1 5/2019 Ng et al.

FOREIGN PATENT DOCUMENTS

WO 2016123100 A1 8/2016

OTHER PUBLICATIONS

Denham et al. Multipotent Caudal Neural Progenitors Derived from Human Pluripotent Stem Cells That Give Rise to Lineages of the Central and Peripheral Nervous System. Stem Cells 2015;33:1759-1770 (Year: 2015).*

Osei-Sarfo et al. Wnt Signaling Controls the Specification of Definitive and Primitive Hematopoiesis From Human Pluripotent Stem Cells. Nat Biotechnol. Jun. 2014 ; 32(6): 554-561. (Year: 2014).*

International Search Report corresponding to PCT/AU2017/050440, mailed on Jul. 20, 2017, 6 pages.

Supplementary European Search Report for European Patent Application No. EP 17795198, mailed on Nov. 20, 2019, 15 pages.

Written Opinion of the International Searching Authority corresponding to PCT/AU2017/050440, completed on Jul. 20, 2017, 9 pages.

Bruveris et al. (2015) "Blood Cells Form From Phenotypically Distinct Precursors During Human Blast Colony Differentiation", Poster Presentations/Experimental Hematology, 43:S60 (1 page, Poster Presentations No. 3039).

(Continued)

*Primary Examiner* — Taeyoon Kim

(74) *Attorney, Agent, or Firm* — Morgan, Lewis & Bockius LLP

(57) ABSTRACT

The invention relates to an isolated cell having, after culturing a pluripotent stem cell (PSC) in a medium comprising a WNT agonist and an ACTIVIN antagonist, increased HOXA gene expression relative to a PSC not cultured in a medium comprising a WNT agonist and an ACTIVIN antagonist, wherein the cell with increased HOXA gene expression is capable of generating a definitive haematopoietic stem/precursor cell. The invention also relates to use of the cell for generating a definitive haematopoietic stem/precursor cell, and a method for differentiating a PSC into a definitive haematopoietic stem/precursor cell and a definitive haematopoietic stem/progenitor cell differentiated from a PSC by the method. The invention further relates to a therapeutic composition comprising a cell of the invention, and to therapeutic methods and uses of a cell of the invention. The invention also relates to a reporter cell comprising distinguishable SOX17 and RUNXIC reporters, for use in tracking the differentiation of a PSC into a definitive haematopoietic stem/progenitor cell.

14 Claims, 18 Drawing Sheets

Specification includes a Sequence Listing.

(56) References Cited

OTHER PUBLICATIONS

Cerdan et al. (May 1, 2012) "Activin A Promotes Hematopoietic Fated Mesoderm Development Through Upregulation of Brachyury in Human Embryonic Stem Cells", Stem Cells and Development, 21(15):2866-2877.

Chanda et al. (Sep. 26, 2013) "Retinoic Acid Signaling is Essential for Embryonic Hematopoietic Stem Cell Development", Cell, 155:215-227.

Clarke et al. (May 2013) "The expression of Sox17 Identifies and Regulates Hemogenic Endothelium", Nature Cell Biology, 15(5):502-510 (18 pages).

Dou et al. (Jun. 2016) "Medial HOXA Genes Demarcate haematopoietic stem Cell Fate During Human Development", Nature Cell Biology, 18(6):595-606 (32 pages).

Ferrell et al. (2015) "The RUNX1 +24 Enhancer and P1 Promoter Identify a Unique Subpopulation of Hematopoietic Progenitor Cells Derived from Human Pluripotent Stem Cells", Stem Cells, 33:1130-1141 (13 pages).

Hatzimichael et al. (2010) "Hematopoietic Stem Cell Transplantation", Stem Cells and Cloning: Advances and Applications, 3:105-117.

Kennedy et al. (Dec. 27, 2012) "T Lymphocyte Potential Marks the Emergence of Definitive Hematopoietic Progenitors in Human Pluripotent Stem Cell Differentiation Cultures", Cell Reports, 2(6):1722-1735.

Kitajima et al. (Jan. 2016) "GSK3f3 Inhibition Activates the COXIHOX Pathway and Promotes Hemogenic Endothelial Progenitor Differentiation from Human Pluripotent Stem Cells", Experimental Hematology, 44(1):68-74 (10 pages).

Ng et al. (Apr. 10, 2008) "A Protocol Describing the Use of a Recombinant Protein-based, Animal Product-free Medium (APEL) for Human Embryonic Stem Cell Differentiation as Spin Embryoid Bodies", Nature Protocols, 3(5):768-776.

Ng et al. (Nov. 2016) "Differentiation of Human Embryonic Stem Cells to HOXA+ Hemogenic Vasculature that Resembles the Aorta-gonad-mesonephros", Nature Biotechnology, 34(11)1168-1179 (16 pages).

Ng et al. (2015) "HOXA Gene Expression Defines Definitive Fetal Hematopoietic Cells Differentiated from HESCS", Short Talk Presentations/Experimental Hematology, 43(9):S46.

Ng et al. (2005) "The Primitive Streak Gene MIXI1 is Required for Efficient Haematopoiesis and BMP4-induced Ventral Mesoderm Patterning in Differentiating ES Cells", Development, 132(5):873-884.

Pearson et al. (Mar. 21, 2008) "The Stepwise Specification of Embryonic Stem Cells to Hematopoietic Fate is Driven by Sequential Exposure to Bmp4, Activin A, bFGF and VEGF", Development, 135(8):1525-1535(13 pages).

Pick et al. (2007) "Differentiation of Human Embryonic Stem Cells in Serum-Free Medium Reveals Distinct Roles for Bone Morphogenetic Protein 4, Vascular Endothelial Growth Factor, Stem Cell Factor and Fibroblast Growth Factor 2 in Hematopoiesis", Stem Cells, 25:2206-2214.

Slukvin, Igori. (Dec. 12, 2013) "Hematopoietic Specification From Human Pluripotent Stem Cells: Current Advances and Challenges Toward De Novo Generation of Hematopoietic Stem Cells", 122(25):4035-4046.

Sturgeon et al. (2014) "Wnt Signaling Controls the Specification of Definitive and Primitive Hematopoiesis from Human Pluripotent Stem Cell", Nature Biotechnology, 32(6):554-561 (9 pages).

Wang et al. (Aug. 23, 2011) "TGFβ Inhibition Enhances the Generation of Hematopoietic Progenitors from Human ES Cell-derived Hemogenic Endothelial Cells Using a Stepwise Strategy", Cell Research, 22:194-207.

Yu et al. (Dec. 2, 2010) "Retinoic Acid Enhances the Generation of Hematopoietic Progenitors From Human Embryonic Stem Cell-Derived Hemato-Vascular Precursors", Blood, 116(23):4786-4794.

* cited by examiner

GLECDGKVNI CCKKQFFVSF KDIGWNDWII APSGYHANYC EGECPSHIAG TSGSSLSFHS
TVINHYRMRG HSPFANLKSC CVPTKLRPMS MLYYDDGQNI IKKDIQNMIV EECGCS

Figure 17

KKNKNCRRHS LYVDFSDVGW NDWIVAPPGY QAFYCHGDCP FPLADHLNST NHAIVQTLVN
SVNSSIPKAC CVPTELSAIS MLYLDEYDKV VLKNYQEMVV EGCGCR

Figure 18

MVGVGGGDVE DVTPRPGGCQ ISGRGARGCN GIPGAAAWEA ALPRRRPRRH PSVNPRSRAA
GSPRTRGRRT EERPSGSRLG DRGRGRALPG GRLGGRGRGR APERVGGRGR GRGTAAPRAA
PAARGSRPGP AGTMAAGSIT TLPALPEDGG SGAFPPGHFK DPKRLYCKNG GFFLRIHPDG
RVDGVREKSD PHIKLQLQAE ERGVVSIKGV CANRYLAMKE DGRLLASKCV TDECFFFERL
ESNNYNTYRS RKYTSWYVAL KRTGQYKLGS KTGPGQKAIL FLPMSAKS

Figure 19

APMAEGGGQN HHEVVKFMDV YQRSYCHPIE TLVDIFQEYP DEIEYIFKPS CVPLMRCGGC
CNDEGLECVP TEESNITMQI MRIKPHQGQH IGEMSFLQHN KCECRPKKDR ARQENPCGPC
SERRKHLFVQ DPQTCKCSCK NTDSRCKARQ LELNERTCRC DKPRR

Figure 20

MEGICRNRVT NNVKDVTKLV ANLPKDYMIT LKYVPGMDVL PSHCWISEMV VQLSDSLTDL
LDKFSNISEG LSNYSIIDKL VNIVDDLVEC VKENSSKDLK KSFKSPEPRL FTPEEFFRIF
NRSIDAFKDF VVASETSDCV VSSTLSPEKD SRVSVTKPFM LPPVA

Figure 21.

AYRPSETLCG GELVDTLQFV CGDRGFYFSR PASRVSRRSR GIVEECCFRS CDLALLETYC
ATPAKSE

Figure 22

PVPPGEDSKD VAAPHRQPLT SSERIDKQIR YILDGISALR KETCNKSNMC ESSKEALAEN
NLNLPKMAEK DGCFQSGFNE ETCLVKIITG LLEFEVYLEY LQNRFESSEE QARAVQMSTK
VLIQFLQKKA KNLDAITTPD PTTNASLLTK LQAQNQWLQD MTTHLILRSF KEFLQSSLRA
LRQM

Figure 23

SPAPPACDLR VLSKLLRDSH VLHSRLSQCP EVHPLPTPVL LPAVDFSLGE WKTQMEETKA
QDILGAVTLL LEGVMAARGQ LGPTCLSSLL GQLSGQVRLL LGALQSLLGT QLPPQGRTTA
HKDPNAIFLS FQHLLRGKVR FLMLVGGSTL CVRRAPPTTA VPSRTSLVLT LNEL

Figure 24

TQDCSFQHSP ISSDFAVKIR ELSDYLLQDY PVTVASNLQD EELCGGLWRL VLAQRWMERL
KTVAGSKMQG LLERVNTEIH FVTKCAFQPP PSCLRFVQTN ISRLLQETSE QLVALKPWIT
RQNFSRCLEL QCQPDSSTLP PPWSPRPLEA TAPTA

Figure 25

APMTQTTSLK TSWVNCSNMI DEIITHLKQP PLPLLDFNNL NGEDQDILME NNLRRPNLEA
FNRAVKSLQN ASAIESILKN LLPCLPLATA APTRHPIHIK DGDWNEFRRK LTFYLKTLEN
AQAQQTTLSL AIF

Figure 26

APPRLICDSR VLERYLLEAK EAENITTGCA EHCSLNENIT VPDTKVNFYA WKRMEVGQQA
VEVWQGLALL SEAVLRGQAL LVNSSQPWEP LQLHVDKAVS GLRSLTTLLR ALGAQKEAIS
PPDAASAAPL RTITADTFRK LFRVYSNFLR GKLKLYTGEA CRTGDR

Figure 27

MAPARSPSPS TQPWEHVNAI QEARRLLNLS RDTAAEMNET VEVISEMFDL QEPTCLQTRL
ELYKQGLRGS LTKLKGPLTM MASHYKQHCP PTPETSCATQ IITFESFKEN LKDFLLVIPF
DCWEPVQE

Figure 28

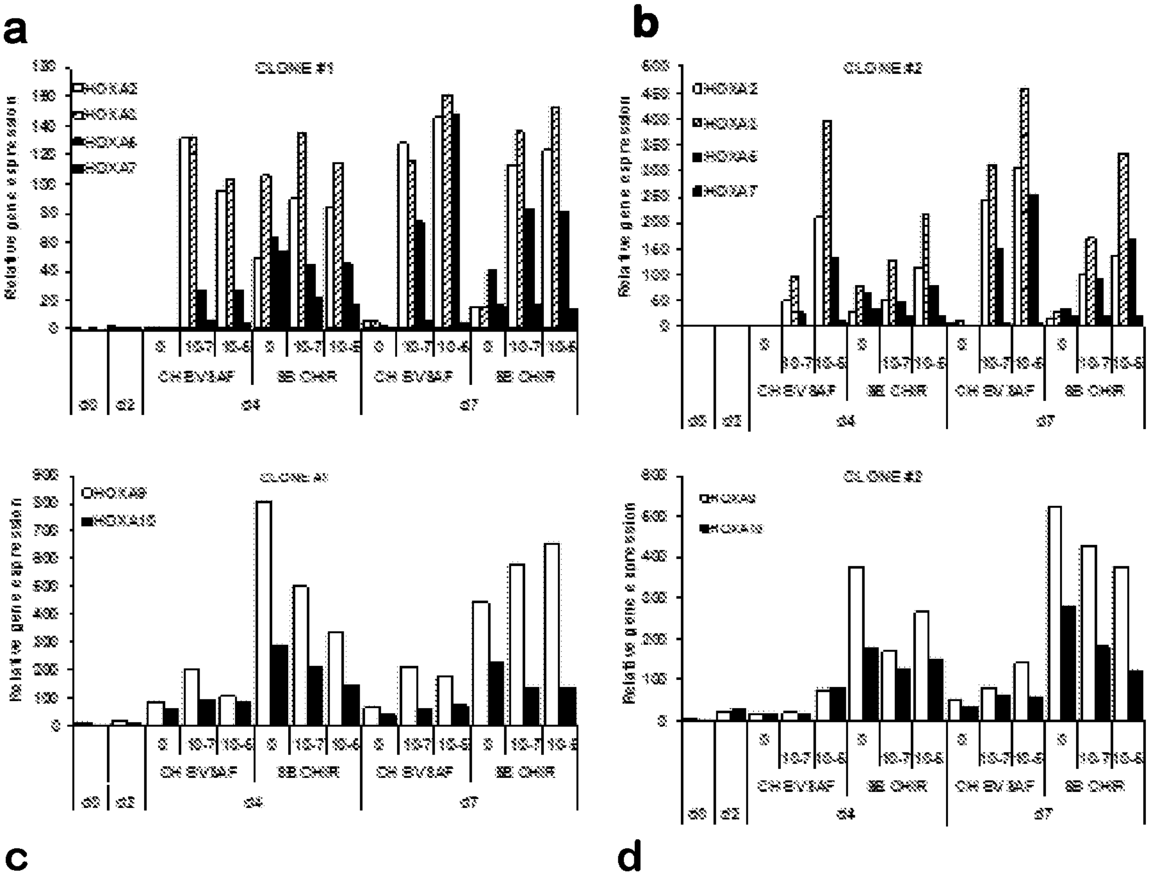

Figure 29

HAEMATOPOIETIC STEM/PROGENITOR CELLS

FIELD

The invention relates to differentiating a pluripotent stem cell (PSC) into a definitive haematopoietic stem/progenitor cell, and to therapeutic uses of the haematopoietic stem/progenitor cell.

REFERENCE TO A "SEQUENCE LISTING"

The present application contains a Sequence Listing, which is hereby incorporated by reference. The accompanying Sequence Listing is submitted in a file entitled "Sequence_Listing_045172-509C01US_ST26.xml," which was created on Oct. 19, 2022, and is approximately 34.3 KB in size.

BACKGROUND

Hematopoietic stem cell (HSC) transplantation permits the reconstitution of the blood cell compartment, for example in patients receiving myeloablative therapy. Because many patients do not have an optimal matched donor, the provision of HSCs from differentiated PSCs would be beneficial. Despite considerable efforts, in vitro haematopoietic differentiation remains skewed towards embryonic, yolk-sac like blood that lacks re-population activity, i.e. primitive haematopoiesis.

It follows that production of definitive haematopoietic stem/progenitor cells from PSCs, in particular human PSCs (hPSCs), remains a significant challenge, and identification of differentiation conditions that replicate early definitive mammalian blood cell development is needed.

It is to be understood that if any prior art publication is referred to herein, such reference does not constitute an admission that the publication forms a part of the common general knowledge in the art in Australia or any other country.

SUMMARY

RUNX1 and SOX17 encode transcription factors critical to definitive haematopoiesis. SOX17 expression is a marker of haemogenic endothelium, whereas one isoform of RUNX1, RUNX1C is a marker of haematopoietic stem/progenitor cells. In view of this, the inventors produced PSCs comprising a SOX17 reporter and/or RUNX1C reporter and used these PSCs to investigate definitive haematopoiesis.

Investigation of homozygous and heterozygous RUNX1C reporter PSCs together with repopulation-competent PSCs from cord blood revealed the surprising finding that HOXA genes were not expressed in the RUNX1C reporter PSCs.

The inventors then set about increasing expression of HOXA genes in RUNX1C/SOX17 dual reporter PSCs using a combination of WNT agonist and ACTIVIN antagonist, and established a robust in vitro differentiation system that encompasses the developmental period from mesoderm formation to AGM-like definitive haematopoiesis, providing a platform for definitive haematopoiesis and the generation of repopulating HSCs.

Based on the inventors' findings, a first aspect provides an isolated cell having, after culturing a pluripotent stem cell (PSC) in a medium comprising a WNT agonist and an ACTIVIN antagonist, increased HOXA gene expression relative to a PSC not cultured in a medium comprising a WNT agonist and an ACTIVIN antagonist, wherein the cell with increased HOXA gene expression is capable of generating a definitive haematopoietic stem/precursor cell.

A second aspect provides an isolated cell, comprising a SOX17 reporter and a RUNX1C reporter, wherein the SOX17 reporter and the RUNX1C reporter are distinguishable.

A third aspect provides use of the cell of the first aspect for generating a definitive haematopoietic stem/precursor cell.

A fourth aspect provides use of the cell of the second aspect for tracking differentiation of a PSC into a definitive haematopoietic stem/precursor cell.

A fifth aspect provides a method for differentiating a PSC into a definitive haematopoietic stem/precursor cell, the method comprising increasing HOXA gene expression by culturing the PSC in medium comprising a WNT agonist and an ACTIVIN antagonist, wherein increased HOXA gene expression is relative to a PSC not cultured in medium comprising a WNT agonist and an ACTIVIN antagonist.

A sixth aspect provides a definitive haematopoietic stem/progenitor cell differentiated from a PSC by the method of the fifth aspect.

A seventh aspect provides a therapeutic composition comprising the cell of the first or sixth aspect.

An eighth aspect provides an infusion bag comprising the cell of the first or sixth aspect or the therapeutic composition of the seventh aspect.

A ninth aspect provides a method for treating a condition, disease or disorder requiring HSC transplantation, the method comprising administering to a subject the cell of the first or sixth aspect or the therapeutic composition of the seventh aspect.

Alternatively or additionally to the ninth aspect, use of the cell of the first or sixth aspect in the manufacture of a medicament for treating a condition, disease or disorder requiring HSC transplantation is provided.

Alternatively or additionally, the cell of the first or sixth aspect or the therapeutic composition of the seventh aspect for use in a method for treating a condition, disease or disorder requiring HSC transplantation, the method comprising administering to a subject the cell or therapeutic composition is provided.

(a) Schematic of the wild type and the targeted RUNX1C allele with GFP sequences inserted into exon 1. The distal (D) and proximal (P) promoters are shown. Non-coding regions of exons are in white, coding in black and the runt domain in red. See also FIG. 2. (b) Brightfield (BF) and overlaid fluorescence images comparing haematopoietic differentiation of d22 RUNX1C$^{GFP/w}$ and RUNX1$^{GFP/GFP}$ cultures. Scale bar, 100 μM. (c) Summary of flow cytometric analyses of differentiating RUNX1$^{GFP/w}$ EBs, correlating the percentage of cells expressing RUNX1C$^{+}$ (R1C) with the expression of mesodermal (PDGFRα) and haematoendothelial cell surface markers (TIE2, CD34 and CD45). (d) Time course analysis showing the percentage of RUNX1C$^{+}$ (R1C) cells expressing each indicated marker. Data taken from experiments in (c). Data in (c, d) is the mean±SEM for 4 experiments. (e, f) Bar plots showing distribution of myeloid and erythroid colony forming cells in RUNX1C$^{GFP/w}$ and RUNX1C$^{GFP/GFP}$ cultures. Data is the mean±SEM of 3 independent experiments. *$p<0.05$, repeated measures ANOVA comparing all groups to $GFP^{+}$ $CD34^{lo}$ population with Tukey's Multiple Comparison Test. (g) Bar plot showing a similar distribution of colony morphology between RUNX1C heterozygous and nullizygous lines. Data represents mean±SEM of three independent experiments. (h) Photomicrographs illustrating examples of erythroid (ERY), granulocytic (GRAN), granulocyte-macrophage (GM) and macrophage or mast cell (MAC/MAST) colony types. Scale bar, 200 μM. (i) Cytocentrifuge preparations of haematopoietic colonies stained with May-Grunwald-Giemsa stain illustrating the morphology of cells derived from different colony types. Examples of nucleated erythroid cells (ERY), granulocytes (GRAN), mast cells (MAST), mixed macrophage and granulocyte (GM) and macrophage (MAC) colonies are shown. Scale bar, 20 μM. (j) Short-term bone marrow homing of d14 $RUNX1^{GFP/w}$ and $RUNX1C^{GFP/GFP}$ EBs sorted on GFP (G) and CD34 (34) expression. Data for 12 mice from 4 independent experiments are shown, with the mean±SEM marked. Only the $GFP^{+}CD34^{+}$ population derived from $RUNX1^{GFP/w}$ cells displayed significant short-term homing. **, $p<0.01$, one way ANOVA comparing all groups to $GFP^{-}$ $CD34^{+}$ from $RUNX1C^{GFP/w}$ with Holm-Sidak's multiple comparison test.

Figure 2:
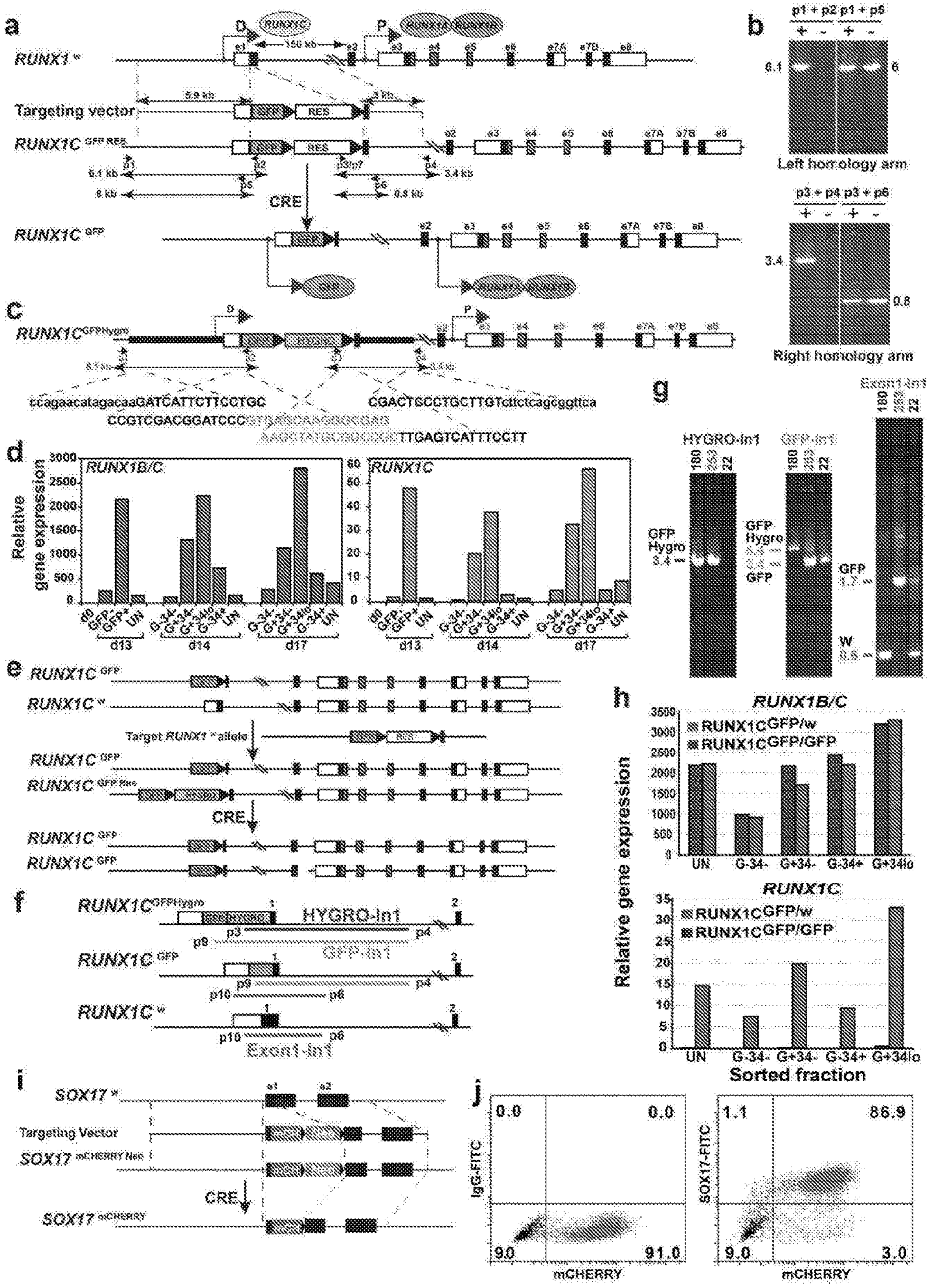

FIG. 2. Generation of RUNX and SOX reporter lines.

(a) Schematic representation of the RUNX1 locus, the targeting vector and the targeted allele with GFP sequences inserted into exon 1(e1). The distal (D) and proximal (P) promoters are shown. Exons (e) are numbered with non-coding exons boxed in white, coding exons in black and exons encoding the runt homology domain in red. e7A and e7B are alternately spliced exons that give rise to RUNX1A and RUNX1B transcripts. RES indicates a cassette encoding either G418 (Neo) or hygromycin resistance flanked by loxP sites (black triangles). The positions of primers used to identify homologously integrated alleles are shown (p1-p7), with the sizes of PCR products indicated. p3 identifies the hygromycin resistance gene whilst p7 is specific for the G418 resistance gene (b) A representative example of the PCR screen to detect homologous integration of the left and right homology arms with the hygromycin cassette containing vector. '+' refers to a clone where the targeting construct was homologously integrated into the RUNX1 locus, and '−' indicates a randomly integrated clone. The combinations of p1/p2 and p3/p4 identify correctly integrated left and right homology arms of the vector. p1/p5 identifies sequences of a wild type allele and p3/p6 identifies vector sequences present even in random integrations. Sequences for each primer are indicated in Table 1. (c) Homologous integration into the RUNX1 locus was further verified by cloning and sequencing the integration sites. An example using primers p1/p2 and p3/p4 is shown. Junction sequences from the genomic locus are shown in lower case. (d) $RUNX1c^{GFP/w}$ EBs harvested on day 13, 14 or 17 were flow-sorted on the basis of GFP and CD34 expression. cDNA synthesized from the sorted samples was analysed by RT-PCR using primers that detected both RUNX1B and RUNX1C (RUNX1B/C) or RUNX1C alone. Note that RUNX1B/C primers revealed expression in $GFP^{-}CD34^{+}$ cells, consistent with expression of the RUNX1B isoform in a subset of $CD34^{+}$ endothelial cells. Gene expression is shown relative to GAPDH. UN, unfractionated cells. (e) Schematic outlining the strategy for generation of the $RUNX1C^{GFF/GFF}$ cell line by re-targeting the wild type RUNX1C allele with the hygromycin targeting vector. (f) Schematic outlining the PCR based screening strategy to identify doubly targeted cell lines, prior to excision of the targeting cassette. (g) PCR analysis using primers shown in (e) to identify GFPHygro, GFP and wild type (w) alleles. Clone 180 depicts an example where the GFPHygro targeting vector has replaced the previous GFP allele, leaving one wild type allele, clone 22 represents depicts one previously targeted GFP allele and one wild type allele and clone 253 represents a clone in which GFPHygro has correctly integrated into the wild type allele resulting in both RUNX1C alleles being targeted. (h) PCR analysis of sorted fractions of RUNX1C GFP/w and RUNX1C GFP/GFP differentiated cells confirming the absence of RUNX1C transcripts from the $RUNX1C^{GFF/GFF}$ line without disruption of the RUNX1B transcripts. Cells were sorted at day 14 based on GFP (G) and CD34 expression. UN, unfractionated cells. (i) Schematic representation of the SOX17 locus, the targeting vector and the targeted allele with mCHERRY sequences inserted into exon 1(e1). The loxP flanked Neo selectable marker was excised with CRE recombinase. (j) Intracellular flow cytometry profiles of $SOX17^{mCHERRY/w}$ hESC differentiated for 5d to endoderm, showing specific staining of $mCHERRY^{+}$ cells with FITC-conjugated SOX17 antibody.

Figure 3:
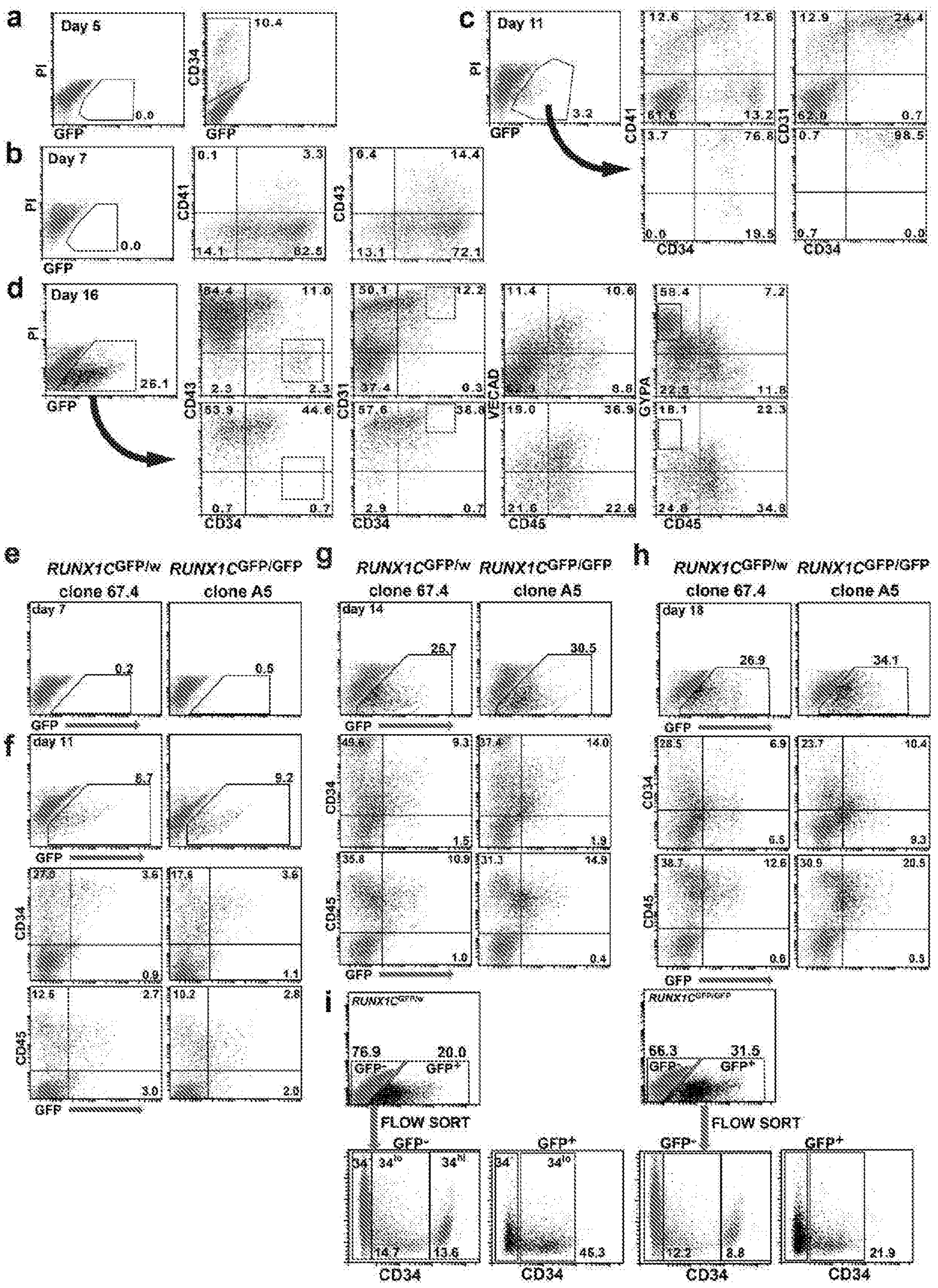

FIG. 3. Analysis of cell surface markers expressed on differentiating $RUNX1C^{GFP/w}$ and $RUNX1C^{GFP/GFP}$ cells.

(a-d) Expression of CD34, CD43 and CD41 precedes GFP expression in $RUNX1C^{GFP/w}$ EBs. Representative flow cytometry analyses of differentiating $RUNX1^{GFP/w}$ EBs indicating that expression of CD34 at day 5 (a) followed by CD41 and CD43 at day 7 (b) antedated GFP expression. Correlation of GFP expression with haematopoietic cell surface markers at day 11 (c) and day 16 (d) revealed that all GFP cells initially co-expressed CD34, CD31, and most expressed CD41. At day 16, GFP expression remained confined to haematopoietic cells expressing the indicated cell surface markers. Red boxed areas represent $CD34^{+}$ $CD31^{+}CD41^{-}CD43^{-}CD33^{-}CD45^{-}$ endothelial cells and the blue boxes mark $GYPA^{+}$ erythroid cells, both of which were $GFP^{-}$. A high proportion of d16 GFP cells co-expressed VECAD and CD45, a combination of surface markers found in mouse haematopoietic stem/progenitor cells. (e-h) Flow cytometry analysis of differentiation timecourse comparing $RUNX1^{GFP/w}$ heterozygous cells (clone 67.4) with $RUNX1C^{GFP/GFP}$ nullizygous clone A5 at (e) day 7, (f) day 11, (g) day 14 and (h) day 18. The percentage of GFP cells and CD34 and CD45 expression patterns were similar for all clones. (i) Strategy for flow cytometry sorting of d14 differentiating $RUNX1^{GFP/w}$ and $RUNX1C^{GFP/GFP}$ cultures based on GFP and CD34 expression.

Figure 4:
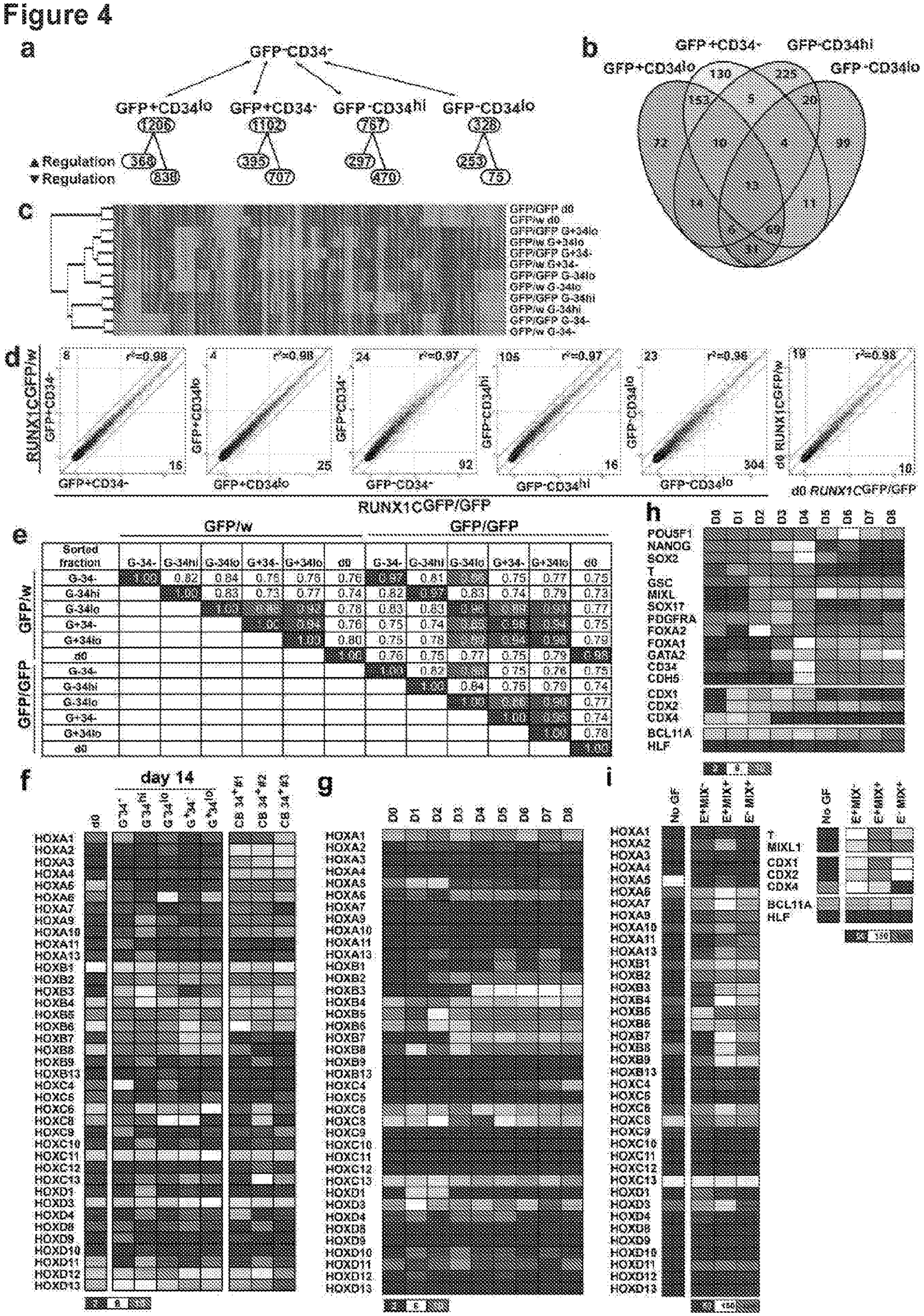

FIG. 4. Comparison of gene expression between $RUNX1C^{GFP/w}$ and $RUNX1C^{GFP/GFP}$ EBs.

(a) Differentially expressed probe sets between the indicated fractions and $GFP^{-}CD34^{-}$ cells for samples including both d14 $RUNX1^{GFP/w}$ and $RUNX1C^{GFP/GFP}$ EBs. (b) Venn diagram showing overlap between probe sets up-regulated in each cell fraction in (a). (c) Hierarchical cluster analysis of the fractions sorted on the basis of CD34 and GFP expression, as well as undifferentiated hESCs isolated from the heterozygote $RUNX1^{GFP/w}$ 67.4 line and the homozygous null $RUNX1C^{GFP/GFP}$ A5 line, based on the top 25% of probes with the greatest variance. (d) Scatter plot representations of the logarithmic signal intensities of the pairwise comparisons between the CD34 and GFP fractions as well as undifferentiated hESCs from the heterozygous and homozygous null lines. Numbers in the top left and bottom right corners indicate the number of probes that are outside of the 2-fold cut-off (indicated by red lines). The correlation coefficient for each differentiated population is similar to the correlation co-efficient for the undifferentiated cells, indicating the similarity of the differentiated progeny. (e) Table indicating the Pearson correlation co-efficient for each of the crosswise comparisons. Note the high correlation coefficients ($r^2 \geq 0.96$) between the equivalent fractions from heterogygous and homozygous RUNX1C cell lines and between the RUNX1C expressing populations ($G^+34^-$ and $G^+34^{lo}$; $r2 \geq 0.94$). (f) Heatmap showing HOX gene expression in sorted d14 $RUNX1^{GFP/w}$ EBs and three samples of CB $34^+$ cells. (g) Heatmap depicting expression of HOX cluster genes during differentiation of $RUNX1^{GFP/w}$ cells for 8 days. Note that the probes for HOXA7 and HOXB9 function poorly in this array, based on comparisons by RT-PCR and RNA-seq, FIG. 15*e*. (h) Heatmap depicting expression of key pluripotency (POU5F1, NANOG, SOX2), mesendoderm (T, GSC, MIXL, SOX17, PDGFRA, FOXA2, FOXA1) and hematopoietic genes (GATA2, CD34, CDH5), the homeobox regulatory CDX genes, and transcription factors BCL11A and HLF, expressed in definitive haematopoietic lineages. Heatmap legend represents log 2 transformed values of signal intensity applied to (g-i). (i) Heatmap showing HOX gene expression in d4 $MIXL1^{GFP/w}$ hESC differentiated in BMP4 and sorted into undifferentiated ($ECADHERIN^+MIXL1^-$ [$E^+MIXL^-$]), primitive streak-like ($E^+MIXL^+$) and nascent mesoderm ($E^+MIXL^+$). Also shown is the expression of selected mesendoderm genes (T, MIXL1), CDX genes, BCL11A and HLF. As a comparison, gene expression in EBs differentiated in the absence of growth factors is shown (No GF). In this case, EBs adopt an early neural fate and HOX genes are not expressed.

Figure 5:
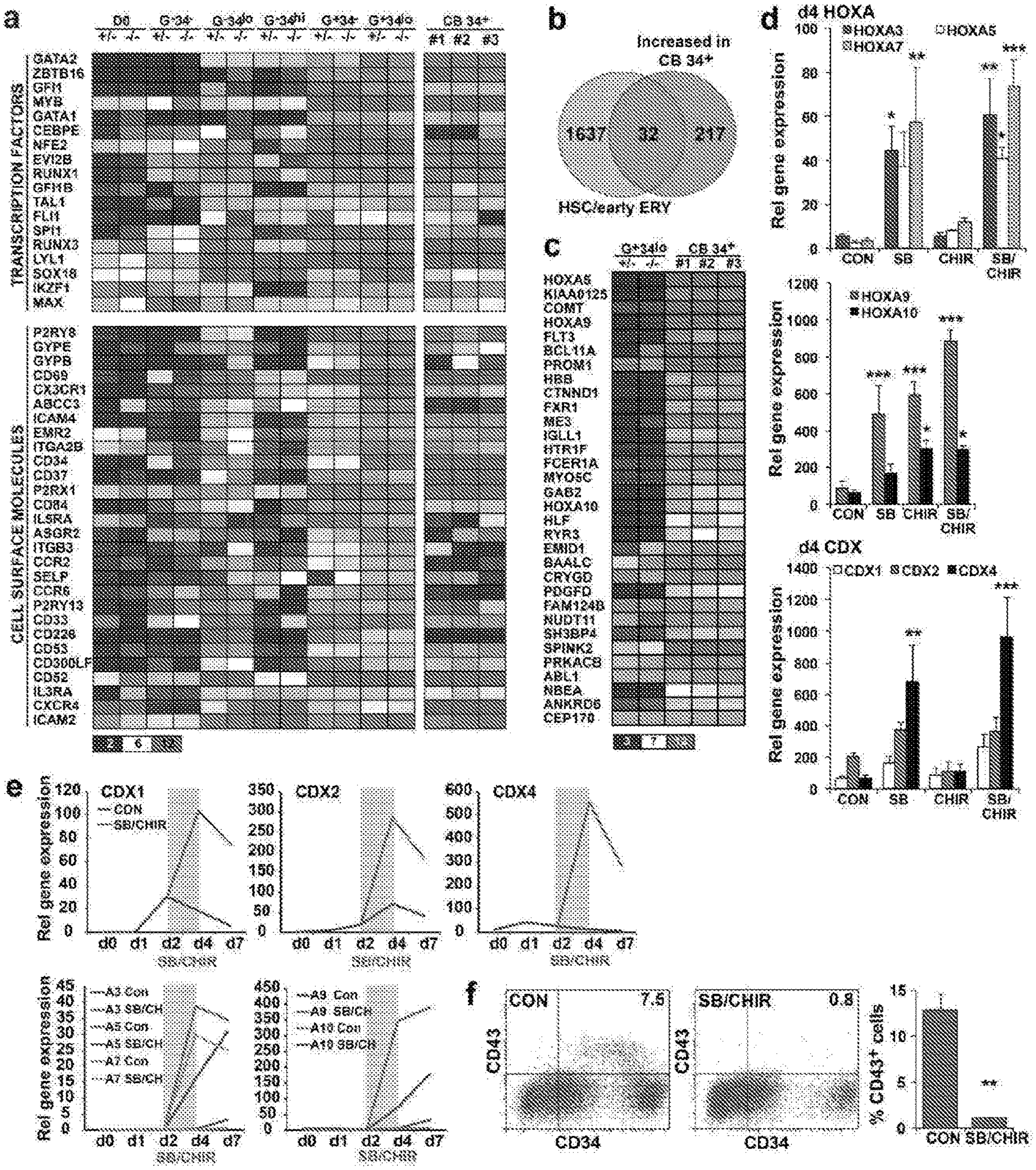
Figure 6:
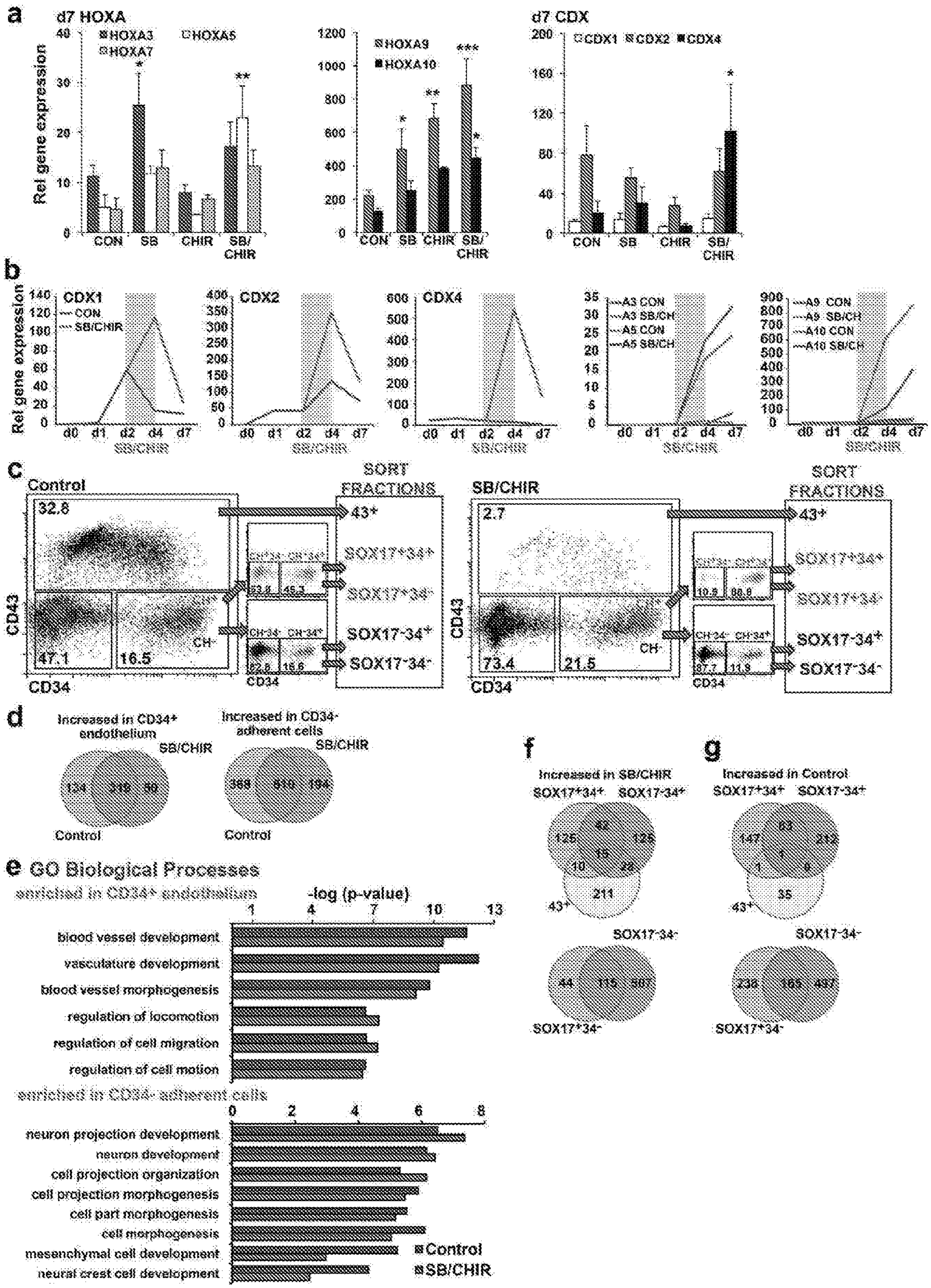

FIG. 5. Differential HOXA gene expression between hESC-derived haematopoietic cells and cord blood modulated by patterning with SB/CHIR. (a) Heatmap showing haematopoietic transcription factors and cell surface molecules differentially expressed between $GFP^+CD34^{lo}$ and $GFP^-CD34^-$ cells. Expression of these genes in $CD34^+$ cord blood (CB $34^+$) samples is shown. Scale reflects signal intensity as log 2. (b) Venn diagram showing overlap between 249 genes up-regulated in CB $34^+$ cells (compared with $GFP^+CD34^{lo}$ cells) and 1669 HSC genes. (c) Heat map showing gene expression of the 32 overlap genes identified in (b) in $GFP^+CD34^{lo}$ sorted samples from RUNX1C heterozygous(+/−) and null(−/−) lines and three samples of CB $34^+$ cells. (d) Relative expression by RT-PCR of HOXA and CDX genes at d4 of differentiation in cultures supplemented with SB431542 (SB), CHIR99021 (CHIR) and the combination of these agents (SB/CHIR). Data is the mean±SEM for 3-4 experiments. *, $p<0.05$; , $p<0.01$; *, $p<0.001$ compared to control using 2 way ANOVA with Holm-Sidak's multiple comparisons test. Data for the d7 timepoint is shown in FIG. 6*a*. (e) Flow cytometry profiles demonstrating reduced CD43 in d7 SB/CHIR EBs compared to controls. Bar graph of CD43 expression, with data showing the mean±SEM for 4 experiments. , $p<0.01$, using Student's t-test. (f) Time course correlating CDX and HOXA gene induction in control and SB/CHIR cultures. An independent CDX time course experiment is shown in FIG. 6***b*.

FIG. 6. HOXA expression in differentiating cultures and generation of RNA-Seq transcriptional profiling data.

(a) Relative expression by RT-PCR of HOXA and CDX genes at d7 of differentiation in cultures supplemented with SB431542 (SB), CHIR99021 (CHIR) and the combination of these agents (SB/CHIR). Data is the mean±SEM for 3-4 experiments. *, $p<0.05$; , $p<0.01$; *, $p<0.001$ compared to control using 2 way ANOVA with Holm-Sidak's multiple comparisons test. Data for the d4 timepoint is shown in FIG. 5*d*. (b) Time course correlating CDX and HOXA gene induction in control and SB/CHIR cultures. An independent CDX time course experiment is shown in FIG. 5*f*. (c) Gating strategy and representative FACS plots showing cell fractions sorted from Control and SB/CHIR treated cultures at day 10. Cells were sorted on the basis of CD43, CD34 and SOX17 (mCHERRY) to identify haematopoietic ($CD43^+$), and $SOX17^+$ and $SOX17^-$ endothelial (abbreviated to $SOX17^+34^+$ and $SOX17^-34^+$) and adherent cells (abbreviated to $SOX17^+34^-$ and $SOX17^-34^-$). (d) Venn diagrams showing overlap in genes whose expression was selectively increased in $CD34^+$ endothelium or $CD34^-$ adherent cells between Control and SB/CHIR cultures. (e) Gene ontology (GO) indicating that similar biological processes were enriched in control and SB/CHIR cultures in the $CD34^+$ and $CD34^-$ fractions from panel (d). (f, g) Venn diagrams showing overlap in (f) SB/CHIR and (g) Control culture differentially up-regulated genes between $CD34^+$ and $CD34^-$ fractions. Genes up-regulated in $CD43^+$ haematopoietic cells clustered more closely to the $CD34^+$ endothelial cells.

Figure 7:
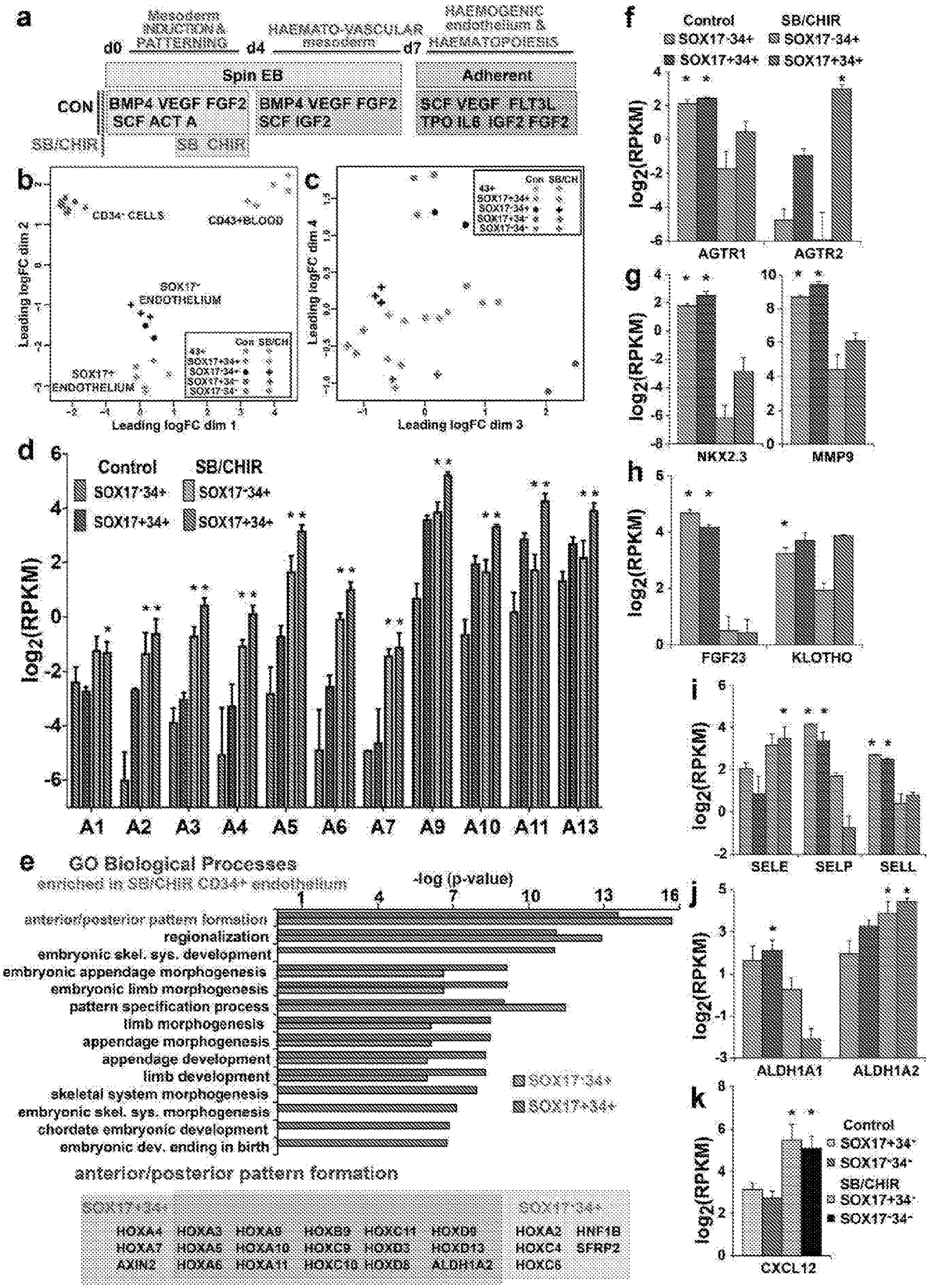

FIG. 7. Transcriptional profiling reveals differential expression of HOXA and endothelial identity genes in SB/CHIR cultures.

(a) Control and SB/CHIR differentiation protocols. (b, c) Multidimensional scaling plots of RNA-Seq data from d10 control (Con) and SB/CHIR (SB/CH) cultures sorted into endothelium, blood and $CD34^-$ adherent cell fractions demonstrating the clustering of sorted fractions by immunophenotype (b) and by culture condition (c). (d) $Log_2$ scale bar plot showing the expression by RNA-Seq of HOXA genes in $SOX17^+34^+$ and $SOX17^-$$34^+$ endothelial cells in control and SB/CHIR cultures (n=3, mean±SEM). Expression in SB/CHIR cultures was higher for asterisked (*) genes ($p<0.05$). See also HOXA expression in other sort fractions in FIG. 12*f, g*. (e) Gene ontology (GO) biological processes enriched in genes more highly expressed in SB/CHIR cultures compared to control in the $CD34^+$ endothelial fractions. The genes comprising the top category are shown. (f-j) $Log_2$ scale bar plots showing the expression of selected differentially expressed endothelial genes in $SOX17^+34^+$ and $SOX17^-34^+$ endothelium from SB/CHIR and control cultures. (k) $Log_2$ scale bar plot showing expression of CXCL12 in $SOX17^+34^-$ and $SOX17^-34^-$ adherent cells between SB/CHIR and control cultures. Asterisks (*) indicate significance ($p<0.05$) compared to the alternate culture condition (n=3, mean±SEM).

Figure 8:
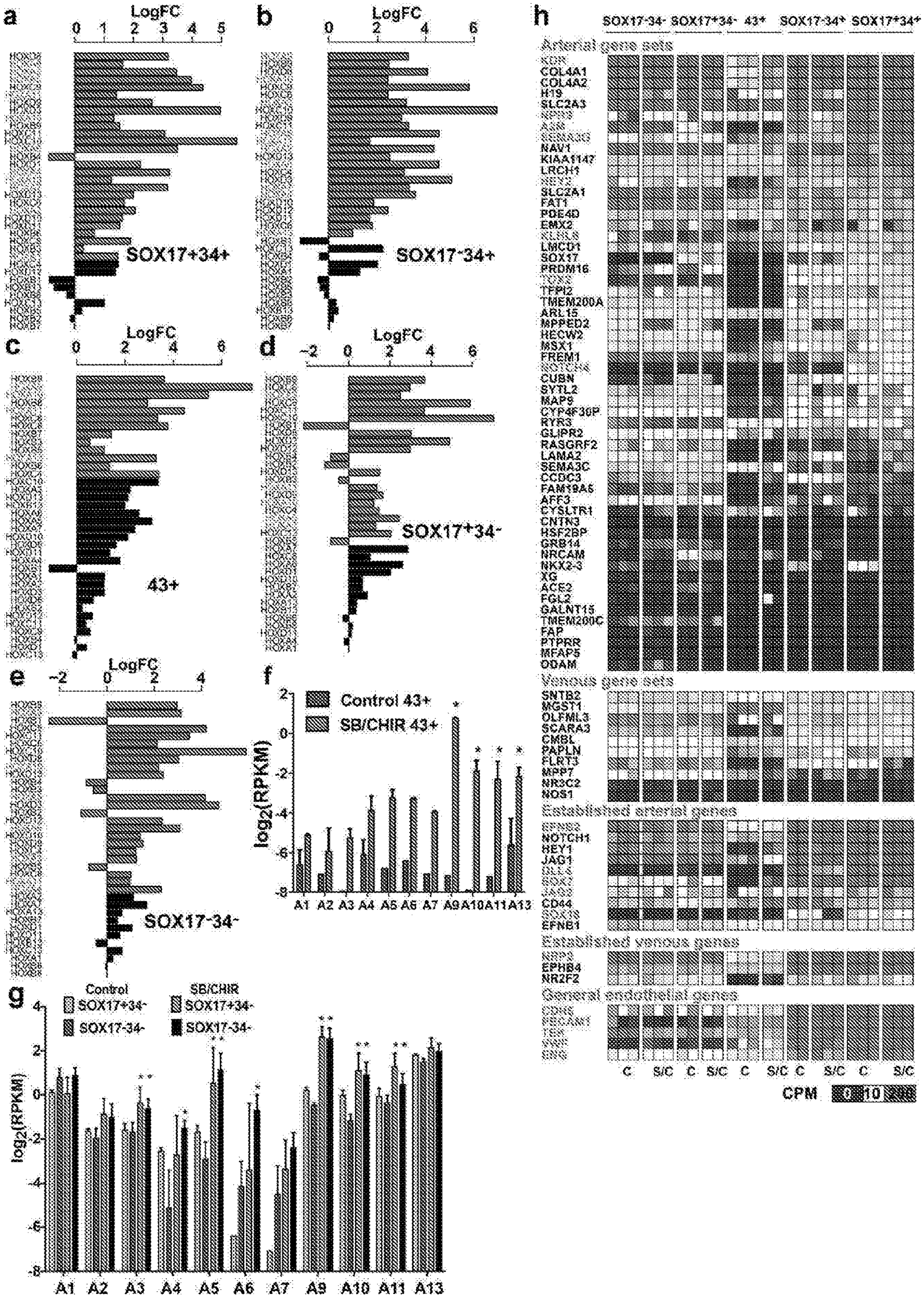

FIG. 8. Differential HOX gene expression and expression of vascular genes in sorted fractions from control and SB/CHIR cultures.

(a-e) Bar plots showing fold change (log 2) in HOX gene expression in SB/CHIR versus control cultures for each sorted fraction. Red fill indicates the difference was statistically significant ($p<0.05$). Bars are arranged in order of increasing p value from top to bottom. (f, g) Bar plot showing the expression by RNA-Seq of HOXA genes in (f) $CD43^+$ blood cells and (g) $SOX17^+$ and $SOX17^-$ $CD34^-$ adherent cells in control and SB/CHIR cultures (n=3, mean±SEM). Expression in SB/CHIR cultures was higher for asterisked (*) genes ($p<0.05$). (h) Expression of genes by RNA-Seq analysis discriminating arterial and venous gene signatures in umbilical artery and vein endothelium as reported by Aranguren et al. Blood 122, 3982-3992 (2013). Genes shown in red type were selectively expressed in $CD34^+$ sorted fractions as shown in FIG. 6*d*. The sorted cell fraction is indicated at the top of each pair of columns and the Control (C) or SB/CHIR (S/C) culture condition at the bottom.

Figure 9:
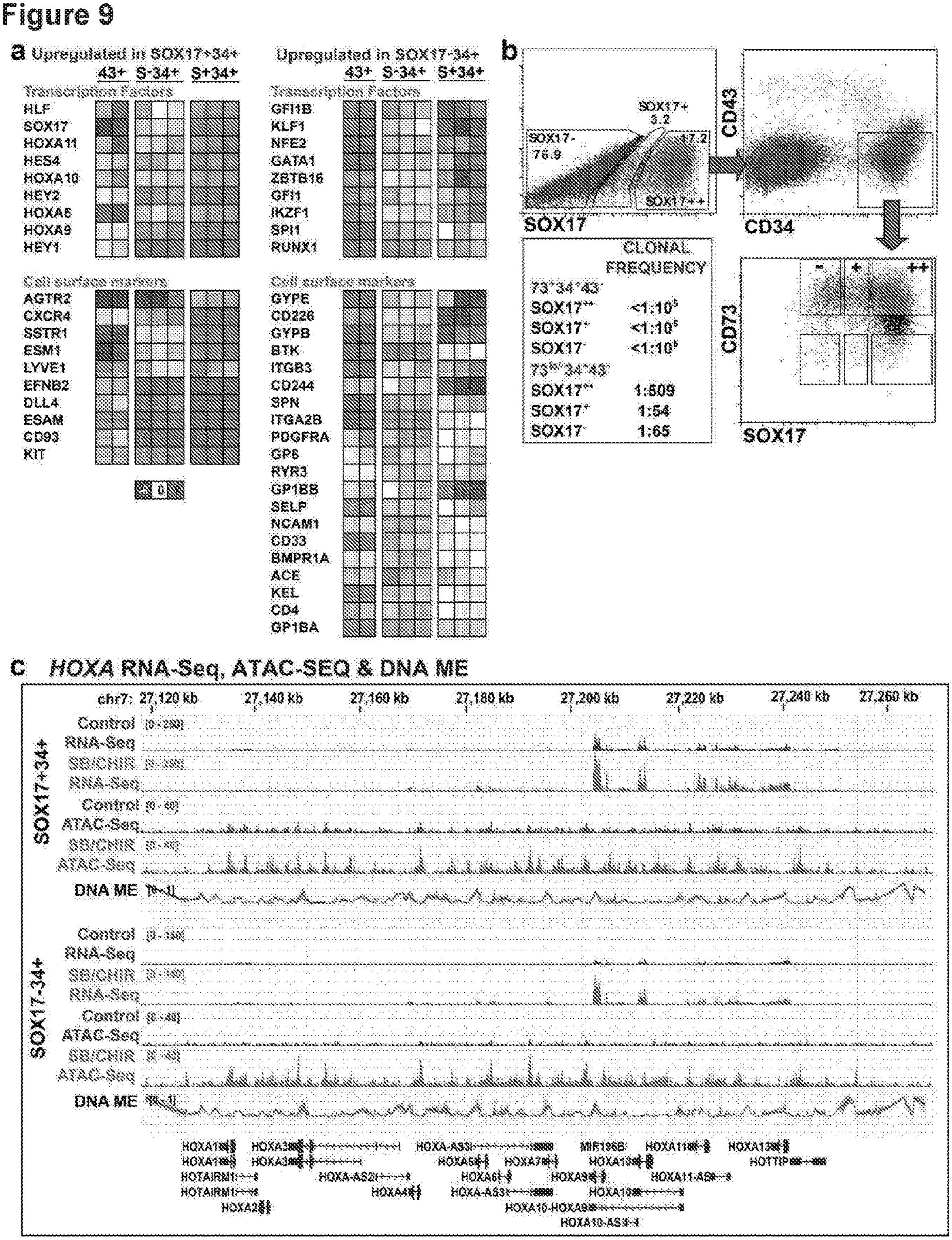

FIG. 9. Characterization of SB/CHIR endothelium reveals differences in gene expression and haemogenic function.

(a) Heatmap showing transcription factors and cell surface markers differentially expressed between d10 $SOX17^{+}$ and $SOX17^{+}$ endothelial cells in SB/CHIR cultures. Expression in sorted haematopoietic cells ($43^{+}$) is shown to demonstrate that genes increased in $SOX17^{-}$ endothelium include many haematopoietic regulators and surface markers. (b) Sorting strategy to determine the clonal frequency of haemogenic capacity of SB/CHIR endothelium, showing sequential gating on SOX17, CD34 and CD43, and CD73. SOX17 expression was stratified as bright (++), dull (+) and negative (−). Most $CD73^{lo/-}$ cells were also $DLL4^{-}$ and $CXCR4^{-}$. (c) RNA-Seq and DNA methylation (ME) array, and chromatin accessibility assessed by ATAC-Seq, comparing the HOXA cluster in control and SB/CHIR $CD34^{+}$ endothelial fractions. In the DNA ME array, the blue and red lines represent the fraction of methylated probe at each locus in control and SB/CHIR cultures, respectively. The shading represents 95% confidence intervals for the DNA ME value. Scale represents counts per million for RNA-Seq and ATAC-Seq. DNA ME is scored for mean probe methylation from 0 (unmethylated) to 1 (methylated).

Figure 10:
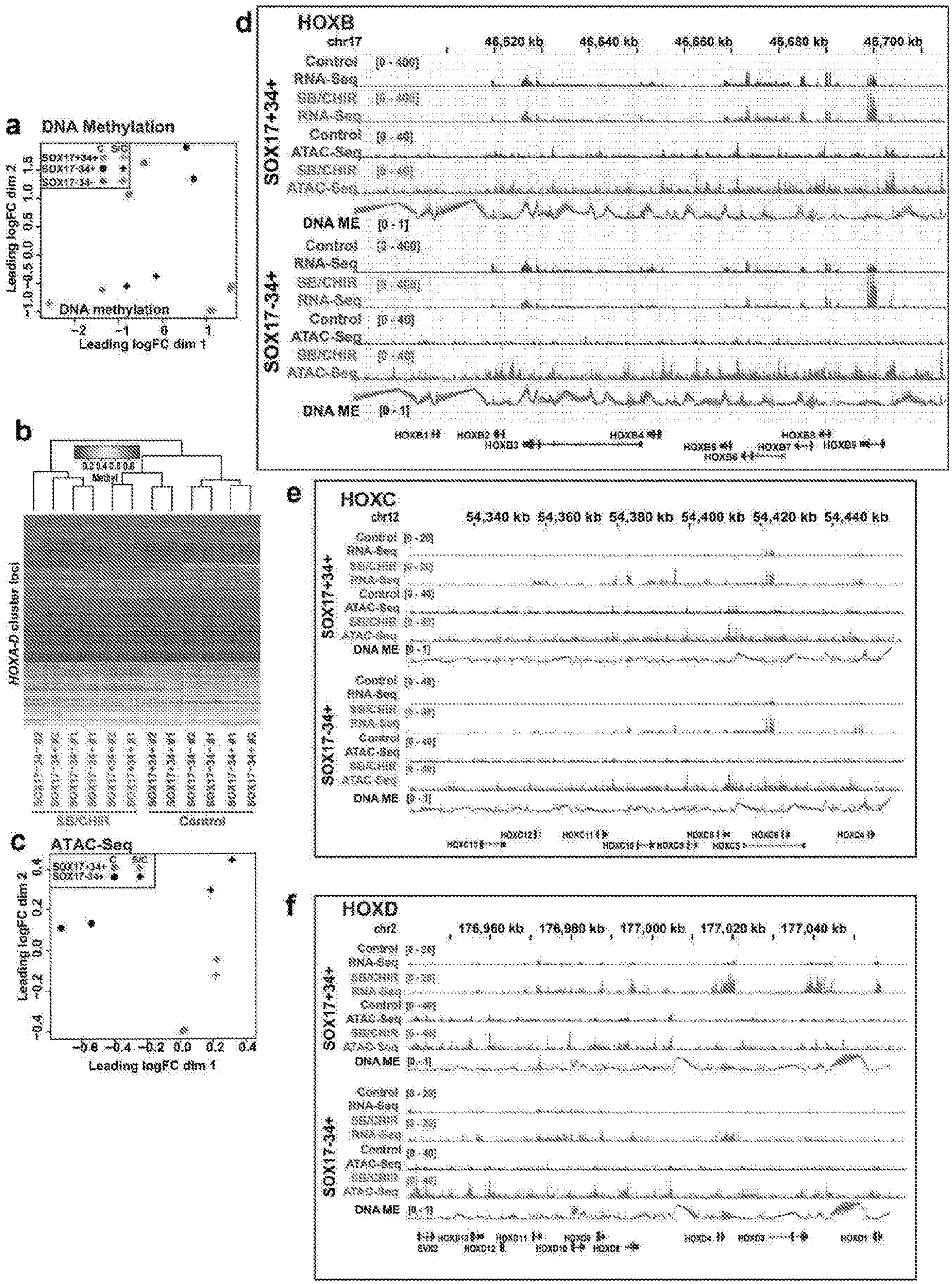

FIG. 10. DNA methylation, RNA-Seq and ATAC-Seq analyses of HOX genes in d10 $SOX17^{mCHERRY/w}RUNX1C^{GFP/w}$ cells.

(a) Multidimensional scaling plots of DNA methylation array data from d10 control (C) and SB/CHIR (S/C) cultures sorted into $SOX17^{+}$ and $SOX17^{+}$ endothelium, and $SOX17^{-}34^{-}$ adherent cell fractions demonstrating the clustering of sorted fractions by phenotype and by culture condition. The closer clustering of the control and SB/CHIR samples for the $SOX17^{+}CD34^{+}$ endothelium suggests more similar levels of methylation in these samples. (b) Heatmap of the 1002 methylation probes that encompassed the HOXA-D loci showing global hypomethylation in all samples. Hierarchical clustering indicates additional grouping of samples by treatment type. (c) Multidimensional scaling plots of ATAC-Seq data from d10 control (C) and SB/CHIR (S/C) cultures sorted into $SOX17^{+}$ and $SOX17^{-}$ endothelium, demonstrating the clustering of sorted fractions by phenotype and by culture condition. (d-f) RNA-Seq and DNA methylation (ME) array, and chromatin accessibility assessed by ATAC-Seq, comparing the (d) HOXB, (e) HOXC, and (f) HOXD clusters in control and SB/CHIR $CD34^{+}$ endothelial fractions. In the DNA ME array, the blue and red lines represent the fraction of methylated probe at each locus in control and SB/CHIR cultures cells respectively.

Figure 11:
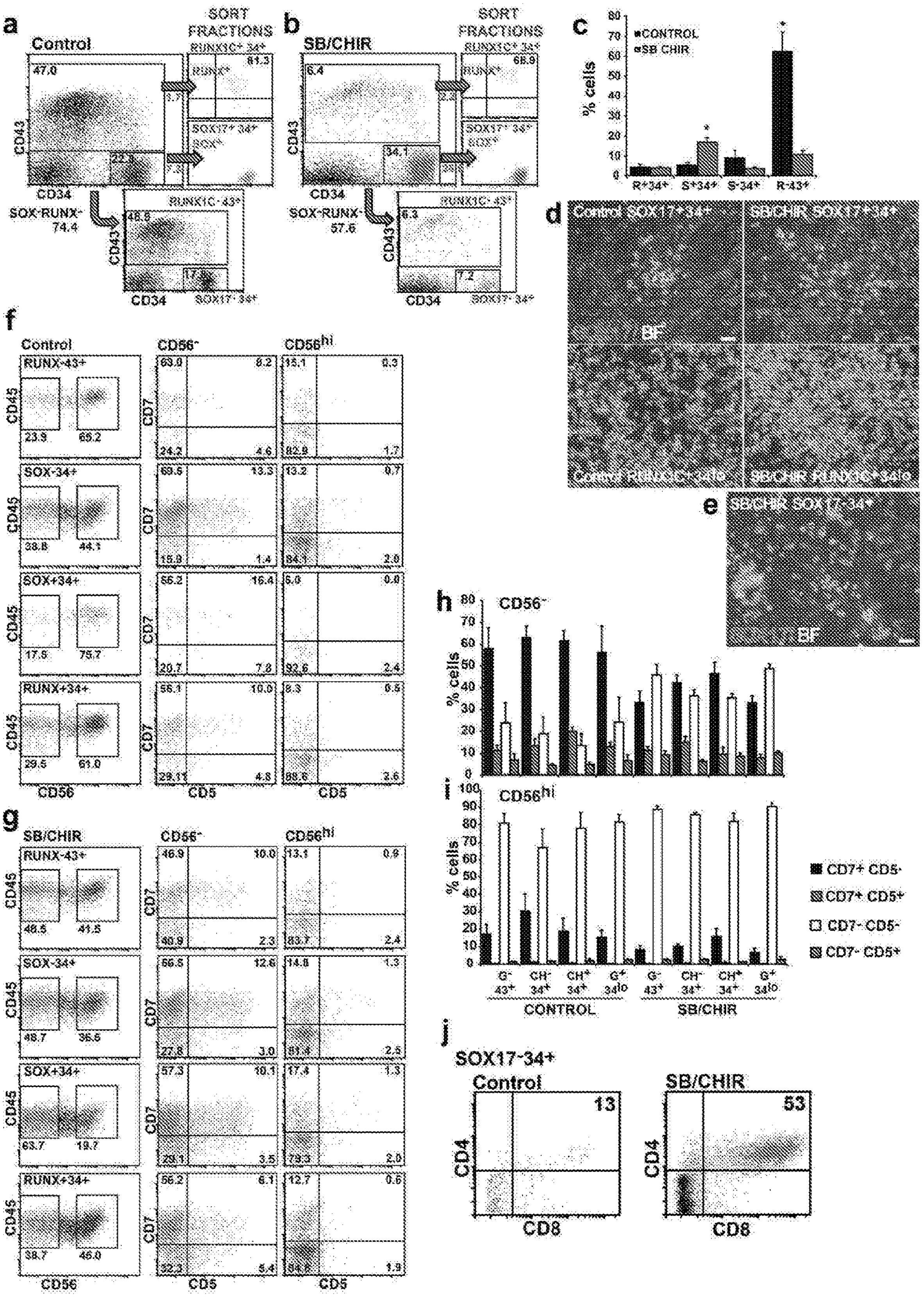

FIG. 11. Analysis of T cell generation in $SOX17^{mCHERRY/w}RUNX1C^{GFP/w}$ cells.

(a, b) Strategy used to sort $RUNX1C^{GFP/w}$ cells differentiated for 7 days in spinner cultures under Control (a) and SB/CHIR (b) conditions into $RUNX1C^{+}34^{+}$, $SOX17^{+}34^{+}$, $RUNX1C^{-}43^{+}$ and $SOX17^{-}34^{+}$ fractions prior to co culture with OP9 DL4 stromal cells. (c) Bar plot comparing the frequency of cells in each fraction indicating that $RUNX1C^{-}43^{+}$ ($R^{-}43^{+}$) cells were less frequent in SB/CHIR cultures, consistent with suppression of primitive hematopoieisis, and that $SOX17^{+}34^{+}$ ($S^{+}34^{+}$) cells increased in response to SB/CHIR. Data represent mean±SEM from 4 experiments. *, $p<0.05$ Student's t test. (d) Day 7 $SOX17^{+}CD34^{+}$ and $RUNX1C^{+}CD34^{lo}$ populations from control and SB/CHIR cultures after 5d on OP9 DL4 showing emerging haematopoietic cells. Scale bar, 50 μM (e) Image of $SOX17CD34^{+}$ sorted cells from SB/CHIR cultures after 9 days on OP9 DL4 showing the generation of $SOX17^{+}$ cells and emergence of haematopoietic cells. Scale bar, 50 μM. (f, g) Representative flow cytometry profiles of control (f) and SB/CHIR (g) d7 sorted fractions after 21 days co-culture on OP9 DL4. Live cells were gated for CD45, then for the NK cell marker CD56 (left panels). T cell progenitors ($CD45^{+}CD56^{-}CD7^{+}CD5^{\pm}$) are shown in red and NK cells ($CD45^{+}CD56^{lo}CD7^{\pm}$) are shown in blue. Whilst T cells and NK cells were generated from all sorted fractions, the yield appeared greater from the SB/CHIR treated cultures. (h, i) Bar plot showing the percentages of cells falling into the CD7 and CD5 quadrants shown in (e, f) for the $CD56^{-}$ T cell progenitors (h) and the $CD56^{hi}$ NK cells (i). (j) Generation of $CD4^{+}CD8^{+}$ T cells following 27 days co-culture on OP9 DL4 of $SOX17\text{-}CD34^{+}$ cells from SB/CHIR treated cultures.

Figure 12:
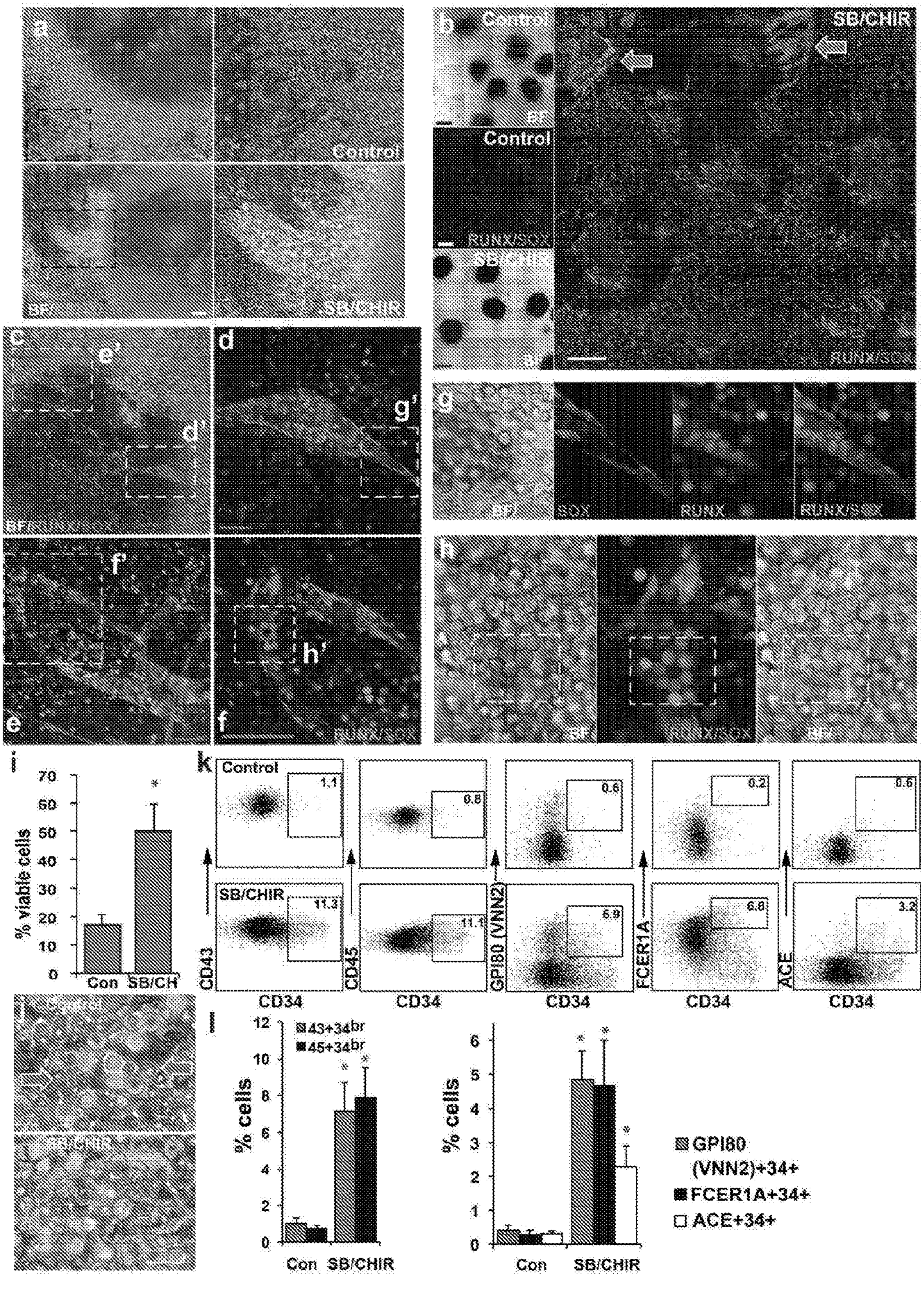

FIG. 12. Development of AGM-like $SOX17^{+}$ vascular structures in SB/CHIR cultures.

(a) Day 11 EBs from control and SB/CHIR cultures showing developing $SOX17^{+}$ vascular structures within and growing out from the EB, contrasting with the lack of identifiable vessels and the early production of blood cells in the control EBs. Boxed areas in left panels are magnified on the right. Scale Bar, 100 μM. (b) Tiled images of d15 EBs from control and SB/CHIR cultures showing multiple $SOX17^{+}$ vascular structures emanating from the SB/CHIR EBs. Arrows indicate two of the vascular structures. Scale bar, 500 μM. (c-f) Images of a d20 SB/CHIR EB in which some $SOX17^{+}$ vascular segments enclose $RUNX1C^{+}$ haematopoietic cells. Panels (d,e,f) show higher power views of boxed areas (d',e',f'). Scale bars, (c) 300 μM, (d-f) 100 μM. (g) Image of boxed area (g') showing $RUNX1C^{+}$ cells enclosed by $SOX17^{+}$ endothelium (h) Image of boxed area (h') showing $RUNX1C^{+}$ and $RUNX1C^{-}$ cells within a $SOX17^{+}$ vascular structure. Scale bar, (g,h) 50 μM. (i) increased viability of haematopoietic cells in d23-d29 cultures of SB/CHIR cells (n=6, mean±SEM; *, $p<0.05$ Student's t test). (j) Brightfield and $RUNX1C^{+}$ overlaid images of control and SB/CHIR cultures at d18 showing dying cells (arrows) in the control cultures. Scale bar, 50 μM. (k) Flow cytometry plots showing increased frequency of haematopoietic genes expressing the indicated stem cell markers at d23 in SB/CHIR cultures. (1) Bar plots showing the increased percentage of haematopoietic cells expressing CD34, GPI80, FCER1A and ACE in d23-29 SB/CHIR cultures (n=4, mean±SEM; *, $p<0.05$ Student's t test).

Figure 13:
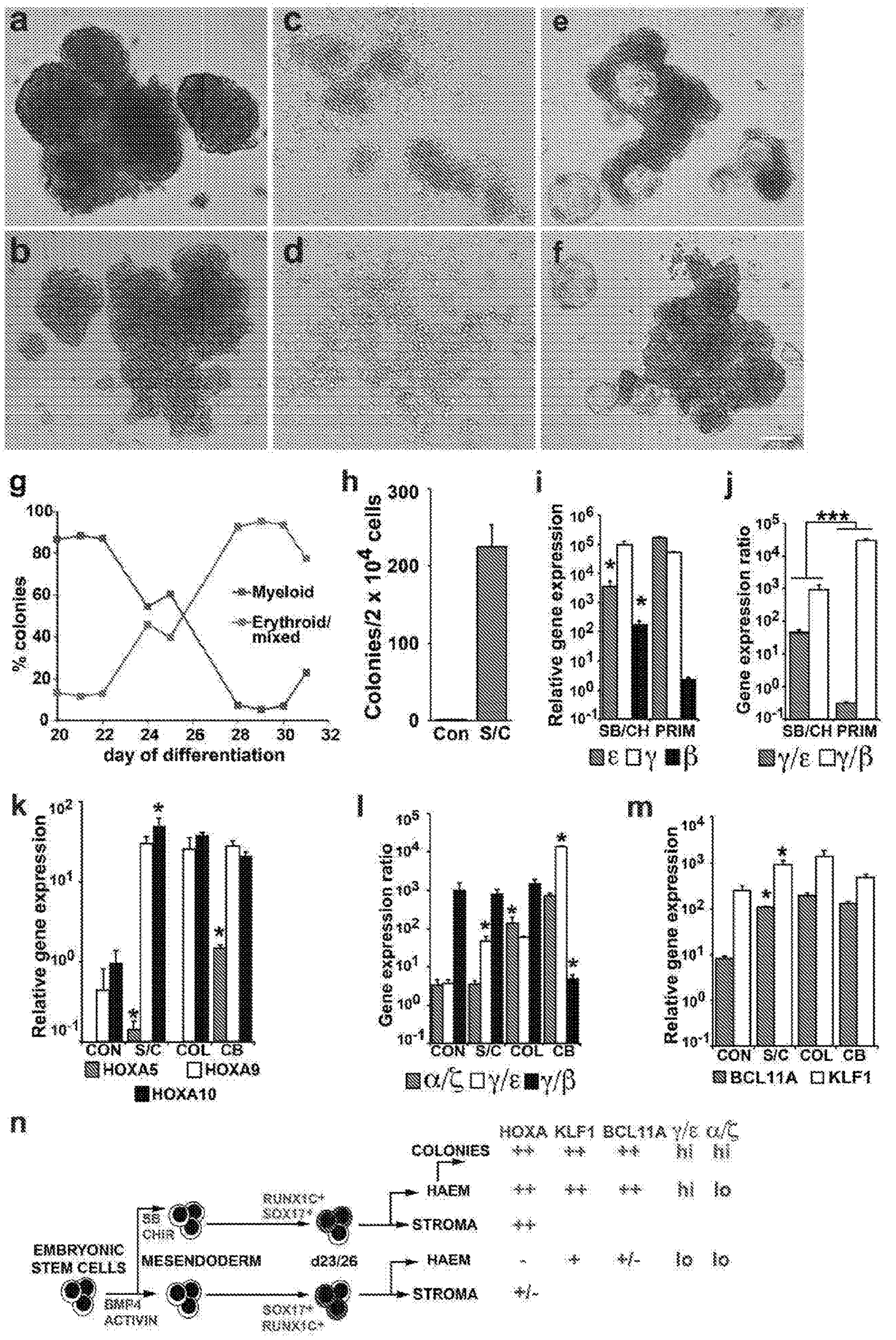

FIG. 13. Generation of foetal stage erythroid cells from $HOXA^{+}$ cultures.

(a-f) Multifocal erythroid burst colonies (a,b), mixed erythroid myeloid colony (c), myeloid colony (d), and erythroid colonies apposed to stromal cysts in MATRIGEL™ supplemented methycellulose (e, f). Panel (a) was a colony from a d23 culture, the remaining panels came from d31 colonies. Scale bar, 100 μM. (g) Proportion of myeloid and erythroid/mixed colony types in methylcellulose in SB/CHIR treated cultures assayed at the day of differentiation indicated. Data represent results from 7 independent experiments with two of the experiments assayed at both earlier and later time points. (h) Bar plot showing the frequency of CFCs in control and SB/CHIR (S/C) cultures. Data is the mean±SEM for 5 experiments (d23-33), $p<0.01$ for S/C versus control using Student's t test. (i) Log scale bar graph showing the relative gene expression of β globin genes in SB/CHIR colonies compared with primitive erythroid colonies (PRIM). Data is the mean±SEM for 6 SB/CHIR and 14 primitive erythroid samples. *, $p<0.005$ using Student's t test. (j) Log scale bar graph showing the ratio of γ/ε and γ/β globin expression in the same data set as (i). ***, $p<0.001$ using Student's t test. (k) Log scale bar graph of the relative gene expression of HOXA genes in control (CON), SB/CHIR cultures (S/C), erythroid colonies (COL) and d10 differentiated cord blood $CD34^+$ cells (CB). Data is the mean±SEM for 3 experiments. *, $p<0.05$ versus CON using Student's t test (1) Log scale bar graph of the ratio of γ/ζ, γ/ε and γ/β globin chain expression in the same experiments as (k). *, $p<0.01$ for γ/ε □□□□ S/C versus CON and CB versus S/C, for α/ζ COL versus S/C and for γβ in CB versus CON, using Student's t test. (m) Log scale bar graph of the relative gene expression of BCL11A and KLF1 in the same experiments as (k)*, $p<0.05$ versus CON using Student's t test. (n) Summary of the experiments in panels (k-m), showing that HOXA expression induced by SB/CHIR translates into persistent clonogenic cells in 3-4 week cultures. These late colonies have increased BCL11A and KLF1 expression and down-regulated embryonic EPSILON and ZETA globin genes, similar to an early foetal liver stage of development.

Figure 14:
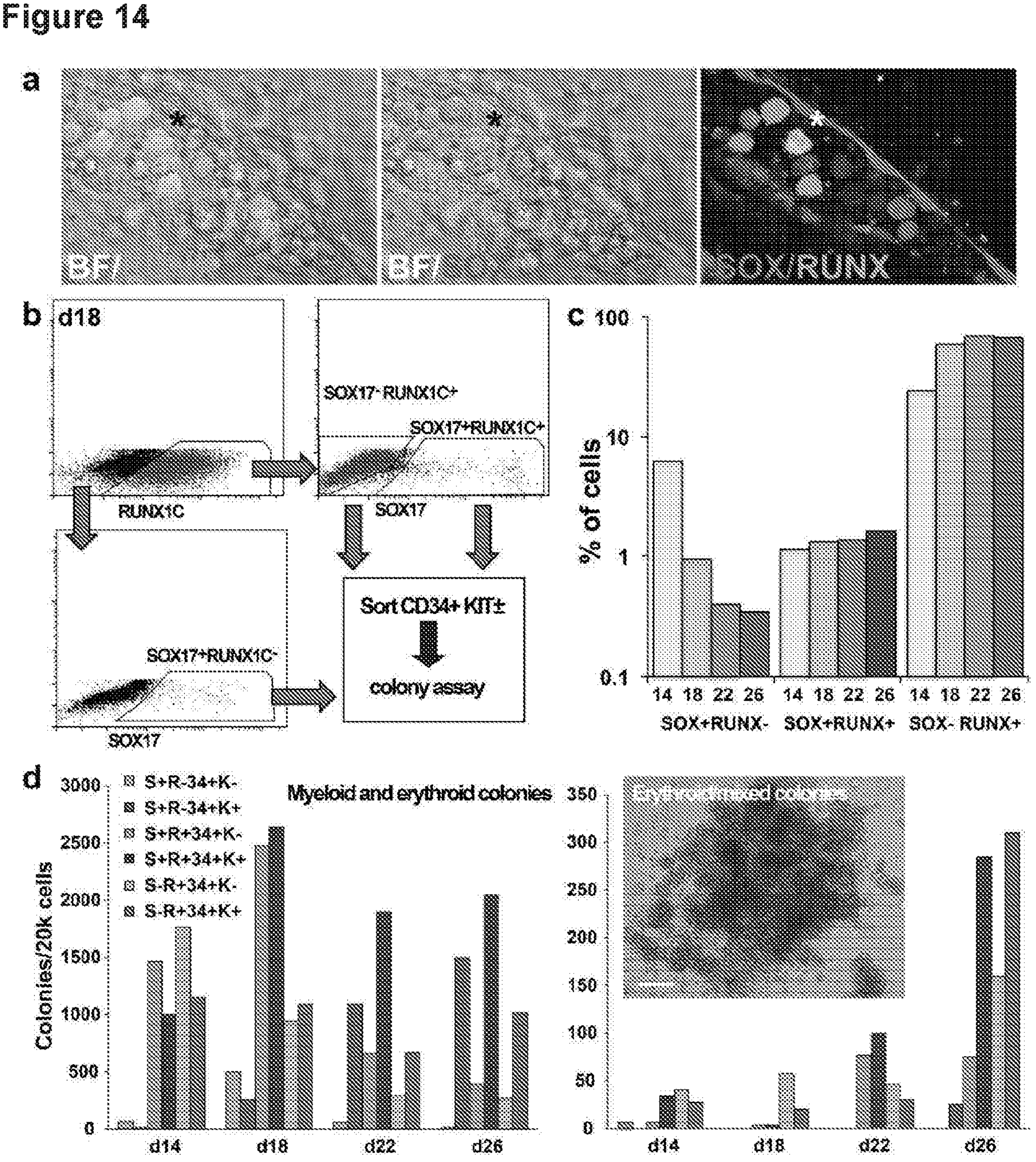

FIG. 14. Emergence of SOX17 and RUNX1C expressing stem/progenitors.

(a) Confocal images of a d18 SB/CHIR culture showing a vessel containing a cell co-expressing SOX17 and RUNX1C. (b) Gating strategy showing the isolation of $SOX^+RUNX^-$, $SOX^+RUNX^+$ and SOX $RUNX^+$ populations that were further stratified by CD34 and KIT expression. (c) Bar plot of the percentage of cells in each indicated fraction across a developmental time course from d14 to d26 of differentiation, showing reciprocal changes in proportions of $SOX^+RUNX^-$ and $SOX^-RUNX^+$ populations. (d) Clonogenic frequency at each time point of populations sorted on SOX17 (S), RUNX1C (R), CD34 (34), and KIT (K). The left panel shows the total number of myeloid and erythroid colonies and the right panel shows only the erythroid-containing colony frequency. The inset shows a multifocal mixed erythroid/myeloid colony from a d26 $S^+R^+34^+K^+$ culture. Scale bar, 100 μM. These data represent a series of 4 independent experiments.

Figure 15:
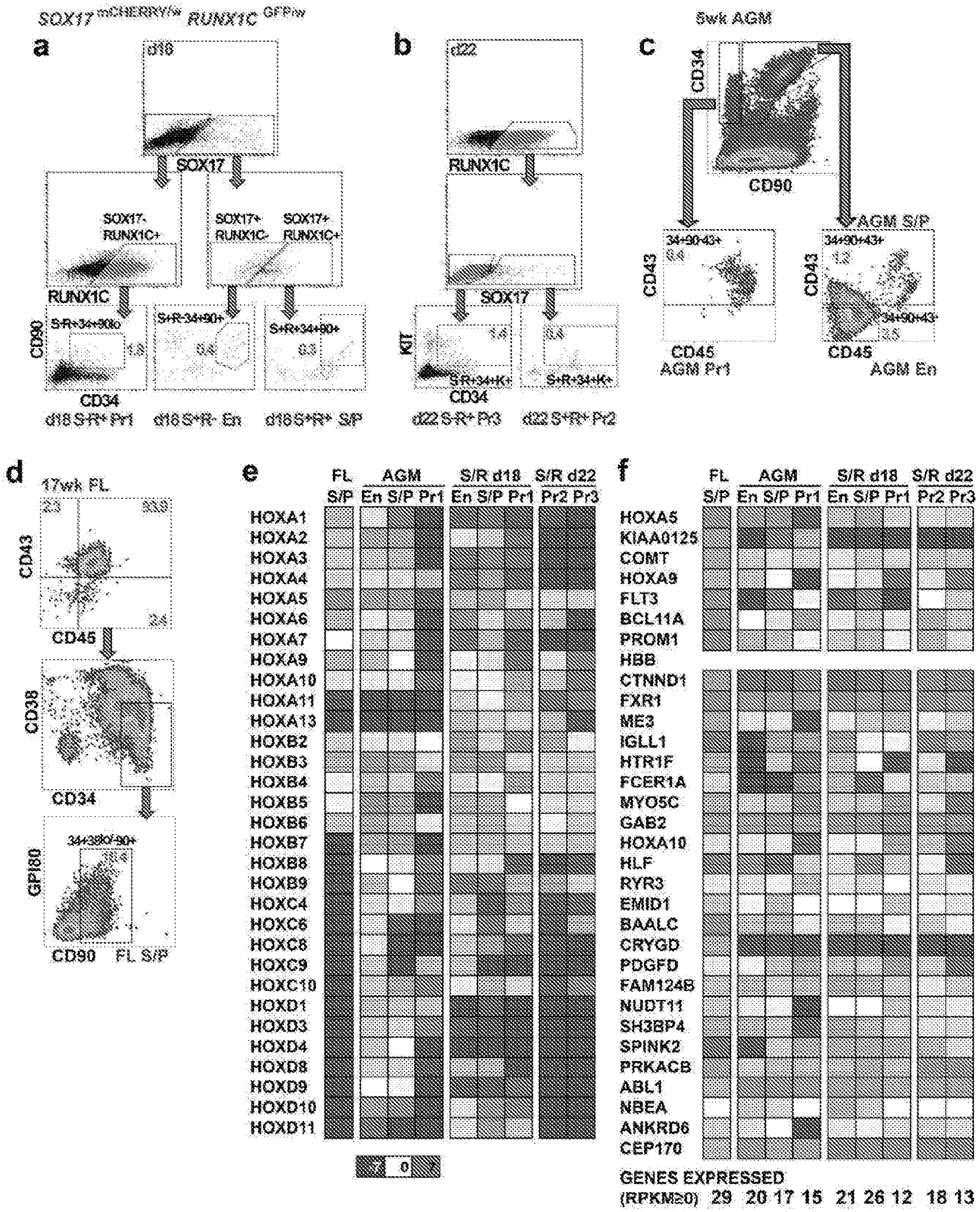

FIG. 15. RNA-Seq Analysis of human FL, AGM and sorted SOX/RUNX d18 and d22 samples.

Sorting strategy for generating (a) $SOX17^{mCHERRY/w}RUNX1^{GFP/w}$ d18 endothelial ($S^+R^-34^+90^+$)(d18 $S^+R^-$ En), stem/progenitor ($S^+R^+34^+90^+$)(d18 $S^+R^+$S/P) and progenitor ($S^-R^+34^+90^{lo}$) (d18 $S^-R^+$Pr1) populations, (b) $SOX17^{mCHERRY/w}RUNX1^{GFP/w}$ d22 progenitor ($S^+R^+34^+K^+$)(d22 $S^+R^+$Pr2) and ($S^-R^+34^+K^+$) (d22 $S^-R^+$Pr3) populations, (c) 5 week AGM endothelium ($34^+90^+43^-$) (En), cells transiting from haemogenic endothelium to haematopoietic stem/progenitors ($34^+90^+43^+$) (S/P) and committed progenitor cell ($34^+90^-43^+$) (Pr1) populations and (d) 17 week foetal liver (FL) sample ($CD43^+CD45^+$) enriched for haematopoietic stem/progenitor cells ($34^+38^{lo/-}90^+$) (S/P). For panels (a-d), the percentage of live cells sorted for each fraction is shown in red type. The $RUNX1C^+$ fractions in panels (a, b) also expressed CD43 or CD45. (e) Expression of HOX genes by RNA-Seq in FL, AGM, and d18 and d22 SOX/RUNX fractions sorted as shown in panels (a-d).

(f) Expression of the list of 32 genes differentially expressed between cord blood and d14 $RUNX1C^+34^+$ cells (see FIG. 5*c*) by RNA-Seq in FL, AGM, and d18 and d22 SOX/RUNX fractions sorted as shown in panels (a-d). HBB was not detected in any sample. The number of genes expressed at ≥0 RPKM in each sort fraction is indicated. Scale is in $\log_2$ RPKM.

Figure 16:
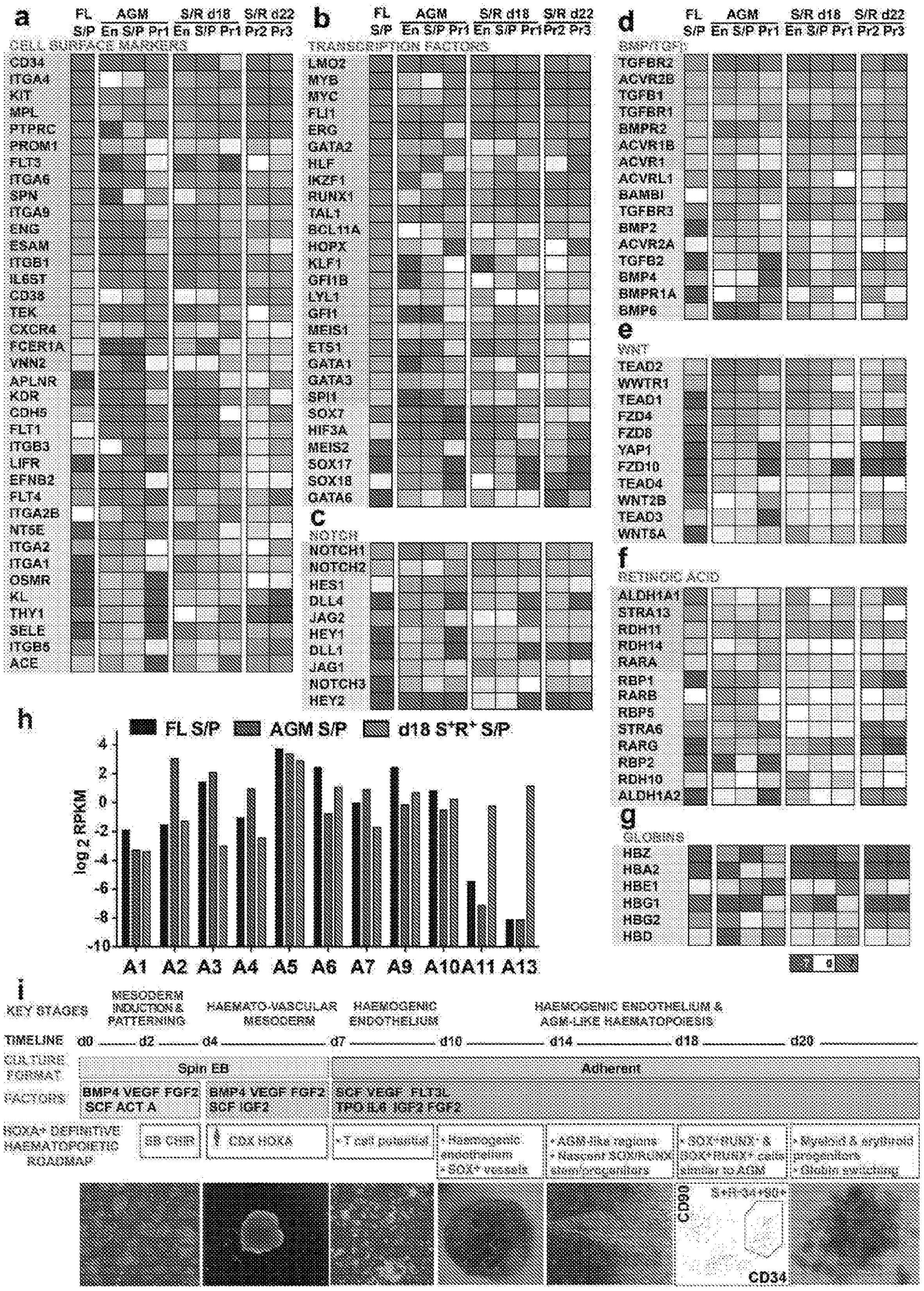

FIG. 16. Transcriptional similarity between SOX/RUNX expressing cells and human AGM.

RNA-seq profiling comparing human foetal liver (FL), human AGM and SOX/RUNX (S/R) populations sorted at d18 and d22. 'S/P' refers to populations with a stem/progenitor phenotype, 'En' marks endothelium and 'Pr1-3' refer to committed progenitor populations with an increasingly mature phenotype. See text for further details. Heatmaps show (a) cell surface markers, (b) transcription factors, (c) NOTCH, (d) BMP/TGFβ (e) WNT, (f) retinoic acid signaling pathway genes and (g) globin genes. Red shaded gene groups are expressed in FL S/P cells, and blue shaded genes are selectively expressed in the AGM S/P fraction. Scale is in $\log_2$ RPKM. (h) Bar graph showing expression of HOXA genes in FL, AGM and d18 $S^+R^+$ S/P populations. These data represent the results of a single flow sorting experiment. (i) Summary of the developmental stages, culture format, growth factors and the haematopoietic differentiation pathway during the transition from hPSC to AGM-like stem/progenitor cells. Thumbnail images illustrate the developmental stages.

FIG. 17 is an amino acid sequence (SEQ ID NO: 1) representing a polypeptide that as a homodimer is one example of human ACTIVIN A.

FIG. 18 is an amino acid sequence (SEQ ID NO: 2) representing a polypeptide that as a homodimer is one example of human BMP4. SEQ ID NO: 2 corresponds to amino acids 303 to 408 of an amino acid sequence of a full length BMP4 precursor.

FIG. 19 is an amino acid sequence (SEQ ID NO: 3) representing a polypeptide that is one example of human FGF2.

FIG. 20 is an amino acid sequence (SEQ ID NO: 4) representing a polypeptide that as a homodimer is one example of human vascular endothelial growth factor (VEGF), also known as VEGF-A.

FIG. 21 is an amino acid sequence (SEQ ID NO: 5) representing a polypeptide that is one example of human stem cell factor (SCF), corresponding to the secreted soluble form of SCF.

FIG. 22 is an amino acid sequence (SEQ ID NO: 6) representing a polypeptide that is one example of human insulin-like growth factor 2 (IGF2).

FIG. 23 is an amino acid sequence (SEQ ID NO: 7) representing a polypeptide that is one example of human interleukin 6 (IL-6).

FIG. 24 is an amino acid sequence (SEQ ID NO: 8) representing a 174 amino acid polypeptide that is one example of human thrombopoietin (TPO) comprising the erythropoietin-like domain of the full length TPO protein.

FIG. 25 is an amino acid sequence (SEQ ID NO: 9) representing a polypeptide that is one example of human FLT3 receptor ligand (FLT3L).

FIG. 26 is an amino acid sequence (SEQ ID NO: 10) representing a polypeptide that is one example of human interleukin 3 (IL-3).

FIG. 27 is an amino acid sequence (SEQ ID NO: 11) representing a polypeptide that is one example of human erythropoietin (EPO).

FIG. 28 is an amino acid sequence (SEQ ID NO: 12) representing a polypeptide that is one example of human granulocyte-macrophage colony-stimulating factor (GM-CSF).

FIG. 29 is a bar graph showing expression of 'anterior' genes HOXA2, HOXA3, HOXA5 and HOXA7, and 'posterior' genes HOXA9 and HOXA10 in hPSCs differentiated in medium supplemented with CHIR99021, BMP4, VEGF, SCF, ACTIVIN A and FGF2 (denoted CH BVSAF) from d0-4, or with an additional pulse of SB431542 and CHIR99021 (denoted SB CHIR) from d2-4 in the absence (denoted 0) or presence of the retinoic acid analogue EC23 at $10^{-5}$ M or $10^{-5}$ M concentrations from d2-4 (denoted 10-5 and 10-7, respectively).

DETAILED DESCRIPTION

Repopulating HSCs have an origin distinct from the yolk sac, and are first located in the aorta-gonad-mesonephros (AGM) and placenta. Cell clusters budding from the ventral aortic endothelium in the AGM harbour the earliest HSCs and express the transcription factor RUNX1, without which clusters do not form and foetal liver haematopoiesis fails.

Three isoforms of RUNX1 (RUNX1A-C) are transcribed from two promoters in humans and mice. In mouse embryos, Runx1b marks haemogenic endothelium, whilst Runx1c is expressed in haematopoietic progenitor cells and is the dominant isoform in foetal liver haematopoietic cells. Runx1b is required in AGM endothelium for definitive haematopoiesis and Runx1b heterozygous mice display defects in HSC and progenitor generation. Conversely, loss of both Runx1c alleles only modestly impacts haematopoiesis and a phenotype for haploinsufficient Runx1c has not been reported.

SOX17 is a second critical transcription factor required for early definitive haematopoiesis in the mouse. In haematovascular development, SOX17 is largely expressed in the arterial system of the embryo. It marks haemogenic endothelium in the AGM and is required for the generation of nascent HSCs from the AGM and for their maintenance in the foetal liver. As with RUNX1C, a haploinsufficient phenotype was not reported for SOX17.

Based on these key roles in haemogenic endothelium and in identifying haematopoietic progenitors, the inventors generated reporter cell lines for SOX17 and/or RUNX1C. In initial studies, RUNX1C marked a subset of $CD34^+$ cells highly enriched for haematopoietic progenitors that homed to the bone marrow, but did not engraft. Exploring molecular differences between PSC-derived and repopulation-competent cord blood (CB) $CD34^+$ cells, the inventors revealed that the $RUNX1C^+CD34^+$ cells failed to express HOXA genes, indicating incorrect mesoderm patterning.

Consequently, the inventors have shown that simultaneous modulation of WNT and ACTIVIN signaling yields haematopoietic stem/progenitor cells with HOXA codes that more closely resemble those of cord blood. These cultures generate a network of aorta-like $SOX17^+$ vessels, from which $RUNX1C^+$ blood cells emerge—reminiscent of definitive haemogenesis within the AGM. Transcriptional profiles of nascent haematopoietic progenitors and corresponding cells sorted from human AGM displayed striking similarity in expression of cell surface receptors, signaling molecules and transcription factors. The inventors demonstrate that HOXA codes are an indicator of mesoderm patterning, thereby enabling generation of definitive haematopoietic lineages from PSCs.

Using HOXA gene expression of human CB progenitor cells as a guide, the inventors devised a differentiation protocol that generates AGM-like structures from hPSCs (FIG. 16*i*). The development of this system was facilitated by a unique $SOX17^{mCHERRY/w}RUNX1C^{GFP/w}$ reporter line and included an EB-based differentiation that retained cellular associations between endothelial, stromal and haematopoietic cells, contrasting with previous approaches that purified endothelial precursors prior to emergence of haematopoietic cells. Providing the combination of a WNT agonist and ACTIVIN antagonist, non-limiting examples of which are CHIR99021 and SB431542 (SB/CHIR) respectively, during a specific temporal window patterned nascent mesoderm to induce sustained HOXA gene expression, and switched differentiation from yolk sac-type primitive haematopoiesis towards definitive haematopoiesis. SB/CHIR treatment led to the development of haemogenic $SOX17^+$ vascular structures and erythroid colony forming cells that displayed a globin profile switching from embryonic to foetal development. Most notably, transcriptional profiling of the most immature hPSC-derived haematopoietic stem/progenitor cells revealed very similar patterns of expression to human AGM, validating the fidelity of the differentiation protocol in generating definitive haematopoietic cells from hPSCs.

The inventors were struck by the low levels of HOXA expression in hPSC-derived vascular and haematopoietic progenitors derived under control culture conditions. Given that HOXA5, HOXA7, HOXA9 and HOXA10 are expressed in HSCs, the inventors hypothesized that acquisition of a HOXA 'signature' during hPSC differentiation would underpin the capacity to eventually generate repopulating cells.

Because HOX genes are first expressed in the primitive streak, the inventors trialed factors that influenced mesodermal patterning. These experiments led to the finding that 2 days of culture with the combination of SB and CHIR up-regulated CDX and HOXA gene expression to a greater extent than either agent alone. The inventors found that 2 days was important, as no or minimal effect was observed at 24 hours. The inventors also observed that the synergistic effect of SB/CHIR was unexpected owing to the fundamental unpredictability in the art.

Chromatin accessibility was increased following SB/CHIR and, in the context of hypomethylation of the HOX clusters, indicated that a permissive environment was generated for transcription factor-mediated HOXA gene expression.

A striking consequence of SB/CHIR patterning was the emergence of $SOX17^+$ vessels from day 10 (d10) of differentiation. The expression of aorta-associated genes and the appearance of haematopoietic cells from these vessels resembled AGM development. The restriction of haematopoiesis to discrete regions shows that blood cells only arose from a subset of the $SOX17^+34^+$ endothelium, consistent with reports that haemogenic endothelium displays a distinct phenotype. Indeed, these studies identified that the d10 $SOX17^+$ haemogenic precursors were restricted to the small CD73-negative fraction and that the frequency was greatly increased in cells with lower SOX17 expression.

In previous studies, deletion of Hoxa9 or the whole Hoxa cluster in mesoderm led to significant haematopoietic defects. Additionally, knockdown of HOXA5 or HOXA7 in human foetal liver depleted cells with an HSC-like phenotype and engraftment ability, confirming the importance of HOXA genes in human definitive haematopoiesis. Despite this, studies aiming to generate HSCs through overexpression of HOXA genes have not been successful. A cocktail of genes, of which HOXA9 was one component, was insufficient to generate long term engraftable cells from hPSC-derived $CD34^+$ cells in one study. In a second study, enforced HOXA9 expression in hESCs enhanced haematopoiesis but did not generate HSCs. In the HOXA5 or HOXA7 knockdown study above, it was concluded that even overexpression of multiple HOXA genes did not confer HSC properties on hPSC derived haematopoietic progenitors. These results show that the ability of HOXA genes to orchestrate a functional HSC phenotype requires the correct cellular context.

In contrast to control cultures, SB/CHIR cultures generated late progenitors with globin chain synthesis indicative of a switch to a foetal developmental stage. Erythroid differentiated hPSCs usually express EPSILON and GAMMA globin, although prolonged culture in human plasma or on stromal layers has yielded predominantly GAMMA or GAMMA and BETA globin expressing cells. A switch from EPSILON to GAMMA globin exclusively in SB/CHIR cultures, associated with the increased expression of KLF1 and its target gene BCL11A was identified. In addition, ZETA globin down-regulation was observed later, in the progeny of colony forming cells from SB/CHIR cultures, indicating that distinct factors regulate silencing at the ALPHA globin locus (FIG. 13*l, n*). The residual EPSILON and ZETA expression in SB/CHIR erythroid colonies resembles early mouse foetal liver BFU-e that express some βH1 despite expression of BCL11A and KLF1.

Molecular analysis of human AGM has been limited to date, and the present study represents the first example of transcriptional profiling of sorted fractions from this tissue, with comparisons to human foetal liver and AGM-like populations derived from hPSCs. It has been shown elsewhere that AGM-derived HSCs exclusively derived from the ventral aorta, possessed a $CD34^+CDH5^+CD45^+KIT^+THY1^+ENG^+RUNX1^+CD38^{-/lo}CD45RA^-$ phenotype. It is noteworthy that the AGM S/P and d18 $S^+R^+$ S/P fractions match this phenotype (FIG. 16*a, b*), validating the human AGM sample and supporting the similarity of the hPSC generated cells to these primary cells. It has been shown that, in the mouse, haematopoietic stem/progenitor cells emerging from $Runx1^+$ AGM endothelium expressed Fli1, Kdr, Gata2, Tal1, Lmo2, Lyl1, Erg, Tek and Itga2b in both haemogenic endothelium and emerging haematopoietic progenitor cells, with the added expression of Ptprc, Gfi1b, Runx1, Itgb3, Sfpi1, Gfi1 and Myb in the haematopoietic progenitors. These results show a high degree of concordance with this data set, with most of the genes expressed in the AGM S/P and d18 $S^+R^+$ S/P fractions (FIG. 16*a, b*).

One laboratory transcriptionally profiled endothelial and haematopoietic populations from day 10.5-11 AGM. The laboratory identified transcription of the 'heptad' transcription factors (Tal1, Lyl1, Erg, Fli1, Runx1, Gata2 and Lmo2), in addition to Cdh5, Tek, Esam, Kdr and Eng in haemogenic endothelium and in the HSC compartment. They observed that many additional transcription factors influencing HSC development were selectively expressed in their HSC compartment. The majority of the genes they described were enriched in both the AGM and d18 $S^+R^+$ En and S/P fractions (FIG. 16*a, b*).

These transcriptional data of human primary AGM and hPSC-derived samples show a high degree of concordance with existing human and mouse data, supporting the inventors' conclusion that the hPSC-derived samples represent definitive, human AGM haematopoietic cells, and that there is substantial conservation of definitive haematopoietic development between the species.

In summary, the in vitro differentiation of human PSCs that are 'switched' to definitive haematopoiesis through exposure to SB/CHIR, timed to overlap with the peak expression of primitive streak genes is described herein. Analysis of these cultures revealed the early and sustained expression of HOXA genes, followed by the development of $SOX17^+$ vascular structures from which haematopoietic cells then emerged, resembling the developing mammalian AGM. This is the first report of a culture system that encompasses human haematopoietic development from mesoderm specification to an AGM-like stage and provides robust generation of transplantable human haematopoietic stem cells from pluripotent stem cells.

Unless defined otherwise in this specification, technical and scientific terms used herein have the same meaning as commonly understood by the person skilled in the art to which this invention belongs and by reference to published texts.

It is to be noted that the term "a" or "an" refers to one or more, for example, "a molecule," is understood to represent one or more molecules. As such, the terms "a" or "an", "one or more," and "at least one" may be used interchangeably herein.

In the claims which follow and in the description of the invention, except where the context requires otherwise due to express language or necessary implication, the word "comprise" or variations such as "comprises" or "comprising" is used in an inclusive sense, i.e. to specify the presence of the stated features but not to preclude the presence or addition of further features in various embodiments of the invention.

The term "about" as used herein contemplates a range of values for a given number of ±25% the magnitude of that number. In other embodiments, the term "about" contemplates a range of values for a given number of ±20%, ±15%, ±10%, or ±5% the magnitude of that number. For example, in one embodiment, "about 3 μM" indicates a value of 2.7 to 3.3 μM (i.e. 3 μM±10%), and the like.

Similarly, while differentiation processes include ordered, sequential events, the timing of the events may be varied by at least 25%. For example, while a particular step may be disclosed in one embodiment as lasting one day, the event may last for more or less than one day. For example, "one day" may include a period of about 18 to about 30 hours. In other embodiments, periods of time may vary by ±20%, ±15%, ±10%, or ±5% of that period of time. Periods of time indicated that are multiple day periods may be multiples of "one day," such as, for example, two days may span a period of about 36 to about 60 hours, and the like. In another embodiment, time variation may be lessened, for example, where day 2 is 48±3 hours from day 0; day 4 is 96±3 hours from day 0, and day 5 is 120 hours±3 hours from day 0.

As used herein, a "WNT agonist" is a substance that mimics or increases WNT signaling. A WNT agonist is not to be restricted to a substance acting directly on WNT as the substance may act elsewhere in the WNT signaling pathway.

Non-limiting examples of WNT agonists according to the first or fifth aspects of the invention include small molecules CHIR99021 (CAS 252917-06-9), a 2-amino-4,6-disubstituted pyrimidine, e.g. BML 284 (CAS 853220-52-7), SKL 2001 (CAS 909089-13-0), WAY 262611 (CAS 1123231-07-1), WAY 316606 (CAS 915759-45-4), SB 216763 (CAS 280744-09-4), IQ 1 (CAS 331001-62-8), QS 11 (CAS 944328-88-5), deoxycholic acid (CAS 83-44-3), BIO (CAS 667463-62-9), kenpaullone (CAS 142273-20-9), or a (hetero)arylpyrimidine. A WNT agonist may also be an agonist antibody or functional fragment thereof or an antibody-like polypeptide.

In one embodiment of the first or fifth aspects of the invention, the WNT agonist is CHIR99021 ((CHIR) CAS 252917-06-9), and the PSC is cultured in a medium comprising about 3 μM. In other embodiments, the medium may comprise about 2 μM, about 2.1 μM, about 2.2 μM, about 2.3 μM, about 2.4 μM, about 2.5 μM, about 2.6 μM, about 2.7 μM, about 2.8 μM, about 2.9 μM, about 3 μM, about 3.1 μM, about 3.2 μM, about 3.3 μM, about 3.4 μM, about 3.5 μM, about 3.6 μM, about 3.7 μM, about 3.8 μM, about 3.9 μM, about 4 μM, about 4.1 μM, about 4.2 μM, about 4.3 μM, about 4.4 μM, about 4.5 μM, about 4.6 μM, about 4.7 μM, about 4.8 μM, about 4.9 μM, or about 5 μM CHIR.

Lithium chloride (LiCl) activates WNT signaling and is included in differentiation medium to improve mesoderm induction during the first 48 hours of differentiation, which is understood in the art. The concentration of LiCl in the differentiation medium may be about 0.5 mM, about 0.6 mM, about 0.7 mM, about 0.8 mM, about 0.9 mM, about 1 mM, about 1.1 mM, about 1.2 mM, about 1.3 mM, about 1.4 mM, about 1.5 mM, about 1.6 mM, about 1.7 mM, about 1.8 mM, about 1.9 mM, about 2 mM, about 2.1 mM, about 2.2 mM, about 2.3 mM, about 2.4 mM, or about 2.5 mM. Preferably, as understood in the art, concentration of LiCl in the medium may be about 2 mM.

As used herein, an "ACTIVIN antagonist" is a substance that inhibits or decreases ACTIVIN signaling. An ACTIVIN antagonist is not to be restricted to a substance acting directly on ACTIVIN as the substance may act elsewhere in the ACTIVIN signaling pathway.

Non-limiting examples of ACTIVIN antagonists according to the first or fifth aspects of the invention include small molecules SB 431542 (CAS 301836-41-9), SB 505124 (CAS 694433-59-5), LDN 193189 (CAS 1062368-24-4), LDN 193719 (CAS 1062368-49-3), Dorsomorphin (CAS 866405-64-3), A 83-01 (CAS 909910-43-6), DMH 1 (CAS 1206711-16-1), RepSox (CAS 446859-33-2), or LY 364947 (CAS 396129-53-6). An ACTIVIN antagonist may also be an antagonist antibody or functional fragment thereof or an antibody-like polypeptide.

In one embodiment of the first or fifth aspects of the invention, the ACTIVIN antagonist is SB 431542 ((SB) CAS 301836-41-9), and the PSC is cultured in a medium comprising about 3-4 μM SB. In other embodiments, the medium may comprise about 2 μM, about 2.1 μM, about 2.2 μM, about 2.3 μM, about 2.4 μM, about 2.5 μM, about 2.6 μM, about 2.7 μM, about 2.8 μM, about 2.9 μM, about 3 μM, about 3.1 μM, about 3.2 μM, about 3.3 μM, about 3.4 μM, about 3.5 μM, about 3.6 μM, about 3.7 μM, about 3.8 μM, about 3.9 μM, about 4 μM, about 4.1 μM, about 4.2 μM, about 4.3 μM, about 4.4 μM, about 4.5 μM, about 4.6 μM, about 4.7 μM, about 4.8 μM, about 4.9 μM or about μM SB.

In some embodiments of the first or fifth aspect, the medium may further comprise a retinoid, e.g. retinol or all trans retinoic acid, or a retinoic acid analogue, e.g. AM580 or EC23. The retinoid or retinoic acid analogue may be used in culturing at concentrations between $1\times10^{-9}$ M and $1\times10^{-4}$ M, e.g. $1\times10^{-9}$ M, $0.5\times10^{-9}$ M, $1\times10^{-9}$ M, $0.5\times10^{-7}$ M, $1\times10^{-7}$ M, $0.5\times10^{-6}$ M, $1\times10^{-6}$ M, $0.5\times10^{-5}$ M, $1\times10^{-5}$ M, $0.5\times10^{-4}$ M, or $1\times10^{-4}$ M for a period ranging from one day to one week during differentiation. The retinoid or retinoic acid analogue may be added at or about d1, d2, d3, d4, d5, d6, or d7, d8, d9, d10, d11, or at later time points of differentiation. The retinoid or retinoic acid analogue may be added at or about d4 of differentiation, at or about d7 of differentiation or at or about d12 of differentiation. The retinoid or retinoic acid analogue may be added at more than one differentiation time point.

Determining an effective concentration of a WNT agonist other than SB and/or determining an effective concentration of an ACTIVIN antagonist As used herein, "pluripotent stem cell" or "PSC" refers to a cell that has the ability to reproduce itself indefinitely, and to differentiate into any other cell type. There are two main types of pluripotent stem cell: embryonic stem cells (ESCs) and induced pluripotent stem cells (iPSCs).

As used herein, "embryonic stem cell" or "ESC" refers to a cell isolated from a five to seven day-old embryo donated with consent by subjects who have completed in vitro fertilisation therapy, and have surplus embryos. The use of ESCs has been hindered to some extent by ethical concerns about the extraction of cells from human embryos.

Suitable ESCs for use in the first or fifth aspects of the invention include, but are not limited to, H1 and H9 human ESCs.

As used herein, "induced pluripotent stem cell" or "iPSC" refers to an ESC-like cell derived from adult cells. iPSCs have very similar characteristics to ESCs, but avoid the ethical concerns associated with ESCs, since iPSCs are not derived from embryos. Instead, iPSCs are typically derived from fully differentiated adult cells that have been "reprogrammed" back into a pluripotent state.

Suitable human iPSCs for use in the first or fifth aspects of the invention include, but are not limited to, iPSC 19-9-7T, MIRJT6i-mND1-4 and MIRJT7i-mND2-0 derived from fibroblasts and iPSC BM119-9 derived from bone marrow mononuclear cells. Other suitable iPSCs may be obtained from Cellular Dynamics International of Madison, WI, USA.

As used herein, "definitive haematopoietic stem/precursor cell" refers to a cell or population of cells responsible for producing all mature blood cells throughout the lifespan of an organism. Clinically, they are important for transplantation in blood-related diseases, particularly in subjects undergoing myeloablative therapy. Definitive haematopoiesis is distinguished from primitive haematopoiesis that occurs transiently during early development and arises from the yolk sac.

A definitive haematopoietic stem/precursor cell of the first aspect of the invention or produced by the method of the fifth aspect of the invention may be further characterized by gene and protein expression as detailed in the examples and figures.

As used herein, "embryoid body" and "EB" refers to a three-dimensional aggregate of PSCs. Advantageously, EBs in may be cultured in suspension, thus making EB cultures scalable for clinical applications. Additionally, the three-dimensional structure of EBs, including the establishment of complex cell adhesions and paracrine signaling within the EB microenvironment, enables differentiation and morphogenesis which yields microtissues that are similar to native tissue structures, for example the AGM as disclosed herein.

In one embodiment of the first or fifth aspects of the invention, the PSCs of the present disclosure are cultured as an EB.

Methods for culturing EBs are known the art. A specific example of a spin EB method that may be used in the present invention is described in Ng et al. *Nature Protocols* 3, 768-776 (2008).

As used herein, "increased HOXA gene expression" refers to a PSC expressing one or more genes from the NOXA cluster at a greater level as a result one or more specific culture conditions relative to expression of one or more genes from the HOXA cluster by a reference PSC cultured in the absence of the specific culture conditions. The specific culture conditions encompassed by the present invention are culture of the PSC in the presence of a WNT agonist and an ACTIVIN antagonist.

Gene expression may be measured by a number of means known in the art. For example, gene expression may be measured quantitatively by real time RT-PCR, or gene expression may be measured qualitatively by microarray.

Increased HOXA gene expression may be binary, either "on" or "off". Alternatively, increased HOXA gene expression may be about a 1% increase, about a 2% increase, about a 3% increase, about a 4% increase, about a 5% increase, about a 6% increase, about a 7% increase, about a 8% increase, about a 9% increase, about a 10% increase, about a 20% increase, about a 30% increase, about a 40% increase, about a 50% increase, about a 60% increase, about a 70% increase, about a 80% increase, about a 90% increase, about a 100%, or greater increase. Alternatively, increased HOXA gene expression may be about a 2-fold, about a 3-fold, about a 4-fold, about a 5-fold, about a 6-fold, about a 7-fold, about an 8-fold about a 9-fold, about a 10-fold, or more increase.

In some embodiments of the first or fifth aspects of the invention, the HOXA gene is one or more of HOXA1, HOXA2, HOXA3, HOXA4, HOXA5, HOXA6, HOXA7, HOXA8, HOXA9, HOXA10, HOXA11, and HOXA13. In some embodiments of the first or fifth aspects of the invention, the HOXA gene is one or more of HOXA3, HOXA5 and HOXA9, HOXA10, HOXA11, and HOXA13. In some embodiments, the HOXA gene is one or more of HOXA3, HOXA7, HOXA9 and HOXA10.

As used herein, a "reporter" refers to an expression product, i.e. a nucleic acid or a protein, expressed from a specific locus that is measurable and indicative of transcription from the locus. The reporter may be endogenous or heterologous. Preferably, the reporter is a heterologous protein, examples of which include enzymes, immunoaffinity tags, and fluorescent proteins. Preferably, the reporter is a fluorescent protein. Many examples of fluorescent proteins are known in the art. Examples include GFP, EGFP, YFP, tdTomato, mCherry, mBanana, mTagBFP2 and so on.

According to the present disclosure, a PSC may comprise two or more reporters targeted to different loci, which therefore report expression of the different loci. To be meaningful where multiple reporters are potentially expressed in the same cell, the reporters are selected such that they are distinguishable. With respect to fluorescent proteins, this generally means non-overlapping or minimally-overlapping emission spectra.

Where multiple reporters are potentially expressed in the same cell, the reporters may be expressed at separate times or simultaneously. In one embodiment of the second aspect, the SOX17 reporter and the RUNX1C reporter are expressed at separate times or simultaneously.

In one embodiment of the second aspect, the SOX17 reporter comprises a first fluorescent protein expressed by the cell and the RUNX1C reporter comprises a second fluorescent protein expressed by the cell.

As used herein, "differentiating" and "differentiation" refers to a process of a cell changing from one cell type to another, in particular a less specialized type of cell becoming a more specialized type of cell.

As used herein, "tracking differentiation" refers to the ability to observe differentiation, for example, to observe the endothelial (SOX17) to haematopoietic (RUNX1C) transition of during PSC differentiation to definitive haematopoietic stem/precursor cells.

As used herein, "medium" or its plural "media" refers to a liquid or gel designed to support the growth of cells. In some embodiments, the cell culture medium comprises APEL medium.

As used herein, "APEL" medium refers to the Albumin Polyvinylalcohol Essential Lipids medium described in Ng et al. *Nature Protocols* 3, 768-776 (2008). APEL medium is available commercially. In an embodiment of the first or fifth aspects of the invention, the medium is APEL medium.

All proteins described herein are known to the person skilled in the art, and most if not all proteins described herein are available commercially.

Although the presently disclosed media may include specific components (e.g. morphogens, small molecules, and hematopoietic cytokines), it is contemplated that other components with the same, equivalent, or similar properties may be used in addition to or in place of those disclosed, as are known in the art.

In some embodiments of the first or fifth aspects of the invention, the medium comprises 20-40 ng/mL BMP4, 20-30 ng/mL VEGF, ng/mL SCF, 10-20 ng/mL ACTIVIN A, and 10 ng/mL FGF2.

In some embodiments of the first or fifth aspects of the invention, the concentration of BMP4 in the medium is about 5 ng/mL, about 10 ng/mL, about 15 ng/mL, about 20 ng/mL, about 25 ng/mL, about 30 ng/mL, about 35 ng/mL, about 40 ng/mL, about 45 ng/mL, about 50 ng/mL, about 55 ng/mL, or about 60 ng/mL.

In some embodiments of the first or fifth aspects of the invention, the concentration of VEGF in the medium is about 10 ng/mL, about 15 ng/mL, about 20 ng/mL, about 25 ng/mL, about 30 ng/mL, about 35 ng/mL, about 40 ng/mL, about 45 ng/mL, about 50 ng/mL, about 55 ng/mL, about 60 ng/mL, about 65 ng/mL, or about 70 ng/mL.

In some embodiments of the first or fifth aspects of the invention, the concentration of SCF in the medium is about 10 ng/mL, about 15 ng/mL, about 20 ng/mL, about 25 ng/mL, about 30 ng/mL, about 35 ng/mL, about 40 ng/mL, about 45 ng/mL, about 50 ng/mL, about 55 ng/mL, about 60 ng/mL, about 70 ng/mL, about 80 ng/mL, about 90 ng/mL, about 100 ng/mL, about 110 ng/mL, or about 120 ng/mL.

In some embodiments of the first or fifth aspects of the invention, the concentration of ACTIVIN A in the medium is about 1 ng/mL, about 2 ng/mL, about 3 ng/mL, about 4 ng/mL, about 5 ng/mL, about 6 ng/mL, about 7 ng/mL, about 8 ng/mL, about 9 ng/mL, about ng/mL, about 11 ng/mL, about 12 ng/mL, about 13 ng/mL, about 14 ng/mL, about 15 ng/mL, about 16 ng/mL, about 17 ng/mL, about 18 ng/mL, about 19 ng/mL, about 20 ng/mL, about 21 ng/mL, about 22 ng/mL, about 23 ng/mL, about 24 ng/mL, about 25 ng/mL, or about ng/mL.

In some embodiments of the first or fifth aspects of the invention, the concentration of FGF2, also known as basic fibroblast growth factor, in the medium is about 1 ng/mL, about 2 ng/mL, about 3 ng/mL, about 4 ng/mL, about 5 ng/mL, about 6 ng/mL, about 7 ng/mL, about 8 ng/mL, about 9 ng/mL, about 10 ng/mL, about 11 ng/mL, about 12 ng/mL, about 13 ng/mL, about 14 ng/mL, about 15 ng/mL, about 16 ng/mL, about 17 ng/mL, about 18 ng/mL, about 19 ng/mL, or about 20 ng/mL.

In some embodiments of the first or fifth aspects of the invention, the concentration of IGF2 in the medium is about 20 ng/mL, about 25 ng/mL, about 30 ng/mL, about 35 ng/mL, about 40 ng/mL, about 45 ng/mL, or about 50 ng/mL. Preferably, the medium comprises IGF2 at 30 ng/mL.

In some embodiments of the first or fifth aspects of the invention, the concentration of IL-6 in the medium is about 10 ng/mL, about 15 ng/mL, about 20 ng/mL, about 25 ng/mL, about 30 ng/mL, about 35 ng/mL, about 40 ng/mL, about 45 ng/mL, or about 50 ng/mL. Preferably, the concentration of IL-6 in the medium is 25 ng/mL to 30 ng/mL.

In some embodiments of the first or fifth aspects of the invention, the concentration of IL-3 in the medium is about 10 ng/mL, about 15 ng/mL, about 20 ng/mL, about 25 ng/mL, about 30 ng/mL, about 35 ng/mL, about 40 ng/mL, about 45 ng/mL, or about 50 ng/mL. Preferably, the concentration of IL-3 in the medium is 25 ng/mL to 30 ng/mL.

In some embodiments of the first or fifth aspects of the invention, the concentration of TPO in the medium is about 10 ng/mL, about 15 ng/mL, about 20 ng/mL, about 25 ng/mL, about 30 ng/mL, about 35 ng/mL, about 40 ng/mL, about 45 ng/mL, or about 50 ng/mL. Preferably, the concentration of TPO in the medium is 25 ng/mL to 30 ng/mL.

In some embodiments of the first or fifth aspects of the invention, the concentration of FLT3L in the medium is about 1 ng/mL, about 2 ng/mL, about 3 ng/mL, about 4 ng/mL, about 5 ng/mL, about 6 ng/mL, about 7 ng/mL, about 8 ng/mL, about 9 ng/mL, about 10 ng/mL, about 15 ng/mL, about 20 ng/mL, about 25 ng/mL, about 30 ng/mL, about 35 ng/mL, about 40 ng/mL, about 45 ng/mL, about 50 ng/mL, about 55 ng/mL, about 60 ng/mL, or about 70 ng/mL.

In some embodiments of the first or fifth aspects of the invention, the concentration of EPO in the medium is about 1 U/mL, about 2 U/mL, about 3 U/mL, about 4 U/mL, about 5 U/mL, about 6 U/mL, about 7 U/mL, about 8 U/mL, about 9 U/mL, or about 10 U/mL. Preferably, the medium comprises 3 U/mL, 4 U/mL or 5 U/mL EPO.

In some embodiments of the first or fifth aspects of the invention, the concentration of GM-CSF in the medium is about 10 ng/mL, about 15 ng/mL, about 20 ng/mL, about 25 ng/mL, about 30 ng/mL, about 35 ng/mL, about 40 ng/mL, about 45 ng/mL, or about 50 ng/mL. Preferably, the concentration of GM-CSF in the medium is 25 ng/mL.

Media disclosed herein may be also made in concentrated, including dried, forms that are diluted prior to use, such as 2×, 10×, 100×, or 1000× concentrations.

As used herein, "culturing" refers to the process by which cells are grown under controlled, in vitro conditions.

As used herein, "extracellular matrix" refers to the non-cellular component of all tissues and organs that provides essential physical scaffolding for the cellular components and initiates crucial biochemical and biomechanical cues that are required for tissue morphogenesis, differentiation and homeostasis. It follows that an "extracellular matrix protein" is a protein present in and/or derived from the extracellular matrix. Examples of extracellular matrix proteins include collagens, elastin, fibronectin, laminin, and proteoglycans. Extracellular matrix proteins, including mixtures, are available commercially, e.g. MATRIGEL™.

As used herein, a "condition, disease or disorder requiring HSC transplantation" may be a malignant condition, disease or disorder, for example acute myeloid leukemia (AML), chronic myeloid leukemia (CML), acute lymphoblastic leukemia (ALL), Hodgkin lymphoma (relapsed, refractory), Non-Hodgkin (relapsed or refractory) lymphoma, neuroblastoma, Ewing sarcoma, multiple myeloma, a myelodysplastic syndrome, a glioma, or other solid tumour, or may be a non-malignant condition, disease or disorder, for example thalassemia, sickle cell anemia, aplastic anemia, Fanconi anemia, an immune deficiency syndrome, or an inborn error of metabolism.

A haematopoietic stem/progenitor cell of the first or sixth aspect or produced according to fifth aspect of the invention may be used for treating a condition, disease or disorder requiring HSC transplantation following myeloablative therapy in a subject. Alternatively, haematopoietic stem/progenitor cell of the first or sixth aspect or produced according to fifth aspect of the invention may be used for treating a condition, disease or disorder requiring HSC transplantation that does not require myeloablative therapy in a subject.

As used herein, "myeloablative therapy" refers to treatment, generally radiation or chemotherapy, that kills cells in the bone marrow, including cancer cells.

It will be appreciated by the person skilled in the art that the exact manner of administering to a subject a therapeutically effective amount of a haematopoietic stem/progenitor cell of or produced according to the invention for treating a condition, disease or disorder will be at the discretion of the medical practitioner. The mode of administration, including dosage, combination with other agents, timing and frequency of administration, and the like, may be affected by the diagnosis of a subject's likely responsiveness to treatment with the haematopoietic stem/progenitor cell of or produced according to the invention, as well as the subject's condition and history.

As used herein, the term "therapeutic composition" refers to a composition comprising a haematopoietic stem/progenitor cell of or produced according to the invention that has been formulated for administration to a subject. Preferably, the therapeutic composition is sterile. In one embodiment, the therapeutic composition is pyrogen-free.

The haematopoietic stem/progenitor cell of or produced according to the invention will be formulated, dosed, and administered in a fashion consistent with good medical practice. Factors for consideration in this context include the particular type of condition, disease or disorder being treated, the particular subject being treated, the clinical condition of the subject, the site of administration, the method of administration, the scheduling of administration, possible side-effects and other factors known to medical practitioners. The therapeutically effective amount of the haematopoietic stem/progenitor cell of or produced according to the invention to be administered will be governed by such considerations.

The haematopoietic stem/progenitor cell of the first or sixth aspect or produced according to the fifth aspect of the invention may be administered to a subject by any suitable method including intravenous (IV), intra-arterial, intramuscular, intraperitoneal, intracerobrospinal, subcutaneous (SC), intra-articular, intrasynovial, intrathecal, intracoronary, transendocardial, surgical implantation, topical and inhalation (e.g. intrapulmonary) routes. Most preferably, the haematopoietic stem/progenitor cell of or produced according to the invention is administered IV.

The term "therapeutically effective amount" refers to an amount of the haematopoietic stem/progenitor cell of or produced according to the invention effective to treat a condition, disease or disorder in a subject.

The terms "treat", "treating" or "treatment" refer to both therapeutic treatment and prophylactic or preventative measures, wherein the aim is to prevent or ameliorate a condition, disease or disorder in a subject or slow down (lessen) progression of a condition, disease or disorder in a subject. Subjects in need of treatment include those already with the condition, disease or disorder as well as those in which the condition, disease or disorder is to be prevented.

The terms "preventing", "prevention", "preventative" or "prophylactic" refers to keeping from occurring, or to hinder, defend from, or protect from the occurrence of a condition, a disease or disorder, including an abnormality or symptom. A subject in need of prevention may be prone to develop the condition, disease or disorder.

The term "ameliorate" or "amelioration" refers to a decrease, reduction or elimination of a condition, a disease or disorder, including an abnormality or symptom. A subject in need of treatment may already have the condition, disease or disorder, or may be prone to have the condition, disease or disorder, or may be in whom the condition, disease or disorder is to be prevented.

As used herein, the term "subject" refers to a mammal. The mammal may be a primate, particularly a human, or may be a domestic, zoo, or companion animal. Although it is particularly contemplated that the method and its resulting definitive haematopoietic stem/progenitor cell or population of definitive haematopoietic stem/progenitor cells disclosed herein are suitable for medical treatment of humans, they are also applicable to veterinary treatment, including treatment of domestic animals such as horses, cattle and sheep, companion animals such as dogs and cats, or zoo animals such as felids, canids, bovids and ungulates.

EXAMPLES

Methods

Generation and Validation of Targeted RUNX1C$^{GFP/w}$, RUNX1C$^{GFP/GFP}$, SOX17$^{mCHERRY/w}$ and SOX17$^{mCHERRY/w}$ RUNX1C$^{GFP/w}$ hESC Lines The RUNX1C targeting vectors comprised a 5.9 kb 5' homology arm, sequences encoding GFP, a loxP flanked antibiotic resistance cassette with a PGK promoter driving either neomycin phosphotransferase (PGKneo) or hygromycin resistance (PGKhygro) genes and a 3 kb 3' homology arm (FIG. 2*a*). The homology arms were amplified by polymerase chain reaction (PCR) from HES3 genomic DNA. The GFP sequences were cloned in frame with the start codon of RUNX1C in exon 1, downstream of the distal promoter. Vectors were linearized with XhoI prior to electroporation into wild-type HES3 cells and selection for antibiotic resistant colony growth. Targeted clones were identified by PCR screening using primer pairs p7/p4 (PGK-neo) or p3/p4 (PGKhygro) (FIG. 2*a, b* and Table 1) that produced a 3.4 kb fragment when the 3' homology arm of the vector was correctly integrated. Six targeted clones were identified from a total of 231 screened (2.6%), two from the PGKneo vector and four from the PGKhygro vector. Homologous recombination of the GFP-containing 5' homology arm was confirmed for all positive clones by PCR using primers p1 and p2 (FIG. 2*b*). Correct targeting of the RUNX1C locus was further verified by sequencing the PCR-generated fragments from 5' and 3' arms described above. Two independently isolated RUNX1C$^{GFP/w}$ clones (35 and 67) were expanded and the loxP flanked antibiotic resistance cassettes were excised by transient transfection with a Cre-recombinase plasmid, pEFBOS-Cre-IRESpuro. Several subclones were screened by PCR for the removal of the PGKneo or PGKhygro selection cassettes as well as for the absence of the Cre expression plasmid. Subclones 35.3 and 67.4 were selected for further analysis. Both lines expressed surface markers of undifferentiated hESCs, retained a normal karyotype and formed teratomas following injection of $2\times10^5$ undifferentiated RUNX1C$^{GFP/w}$ hESCs under the kidney capsule of NOD/SCID/IL2Rγ−/− mice. These data are shown in Ditadi et al. *Nature Cell Biology* 17, 580-591 (2015).

A list of primers used in this study, their sequences and locations within the RUNX1 gene or the targeting vector is provided in Table 1. Primers p1-p10 were used for screening of targeted clones and the remaining primers were used for RT-PCR to distinguish the B (Human Fujita a and Human Fujita c) and C (Human Fujita b and Human Fujita c) isoforms or identify the combination of the B and C isoforms (denoted common RUNX1) (fAML1a and rAML1a). See also FIG. 2.

TABLE 1

RUNX PCR primers.

| Primer | Sequence | SEQ ID NO: | Location | Comment |
|---|---|---|---|---|
| p1 | CCCAAATGCTTGAAAGATCATATCC | 13 | 5' of Exon 1 | |
| p2 | GTCGCCGTCCAGCTCGACCAGGATG | 14 | GFP rev | |
| p3 | CTCCGCATTGGTCTTGACCAACTC | 15 | HYGRO fwd | |
| p4 | GCAGCTTTGTACTTGGCAATTCCC | 16 | Intron 1 rev | |
| p5 | TACGTCGACCATCGCTTCCTCCTGA AAATGCAC | 17 | Exon 1 rev | |
| p6 | TCTCACGCACCGACTGAACACTCC | 18 | Intron 1 rev | |
| p7 | CGGTGGGCTCTATGGCTTCTGAGG | 19 | G418R fwd | |
| p9 | TCGGCATGGACGAGCTGTACAAG | 20 | GFP fwd | |
| p10 | CACACTGAATGCAAACCACAGGG | 21 | Exon 1 fwd | |
| Human Fujita a | ACGTGTATGTTGGTCTCCCG | 22 | Exon 3 fwd (5' UTR) | a, c detects RUNX1A/B |
| Human Fujita b | AAGCGATGGCTTCAGACAG | 23 | Exon 1 fwd | b, c detects RUNX1C |
| Human Fujita c | TCACAGTGACCAGAGTG | 24 | Exon 4 rev | |

TABLE 1-continued

| RUNX PCR primers. | | | | |
|---|---|---|---|---|
| Primer | Sequence | SEQ ID NO: | Location | Comment |
| fAML1a | TGTGGTCCTATTTAAGCCAGCCCC | 25 | Exon 8 fwd (3' UTR) | fAML1a and fAML1b detect RUNXB/C |
| rAML1a | TCAGGCTGGGCACGACGAATGCTC | 26 | Exon 8 rev (3' UTR) | |

To generate the RUNX1C$^{GFP/GFP}$ knockout hESC line, the RUNX1C$^{GFP/w}$ line (clone 67.4) was electroporated with the RUNX1C PGKhygro construct described above, resulting in the identification of 2/308 hygromycin resistant clones that were targeted at the 3' end following PCR screening using p3/p4 primers (FIG. 2*e*-*g*). A second PCR using a GFP forward primer (p9) and p4, performed to identify and distinguish the alleles RUNX1C$^{GFP}$ (3.4 kb) and RUNX1C$^{GFPHyg}$ (5.5 kb), confirmed that both alleles were targeted in one of the two clones (#253) and that the PGKhygro vector replaced the previously targeted allele in the second clone (#180). A third PCR screen with a RUNX1C 5' UTR primer (p10) and p6, amplified wild type (600 bp) and GFP targeted (1.7 kb) alleles and confirmed the absence of a wild type allele in RUNX1C$^{GFPHyg}$ clone 253 (FIG. 2*g*). The hygromycin selection cassette was removed by Cre recombinase as described above. The RUNX1C$^{GFP/GFP}$ null line expressed surface markers of undifferentiated hESCs and retained a normal karyotype (data not shown). Differentiated RUNX1C$^{GFP/GFP}$ did not express RUNX1C by PCR (FIG. 2*h*).

The SOX17$^{mCHERRY/w}$ H9 line has been described previously. Briefly, The SOX17-mCHERRY targeting vector comprised an 8.3 kb 5' homology arm that encompassed genomic sequences located immediately upstream of the SOX17 translational start site, sequences encoding mCHERRY, a loxP-flanked PGK-Neo antibiotic resistance cassette and a 3.6 kb 3' SOX17 homology arm. The human ESC line H9 (purchased from WiCell) was electroporated with the linearized vector and correctly targeted clones identified using a PCR based screening strategy as described above. The antibiotic resistance cassette was excised using CRE recombinase. The SOX17$^{mCHERRY/w}$ human ESC line used in this study was validated by demonstrating the correlation between SOX17 and protein and mCHERRY expression on endodermally differentiated cells (FIG. 2*j*).

The dual reporter SOX17$^{mCHERRY/w}$RUNX1$^{GFP/w}$ line was generated in H9 by retargeting GFP to the RUNX1C locus in the SOX17$^{mCHERRY/w}$ human ESC line, as outlined above.

For all lines, genomic integrity was confirmed using the Illumina HumanCytoSNP-12 v2.1 array.

Gene Expression Analysis

Total RNA was prepared from ES cells and dissociated EBs using the Qiagen RNeasy kit or the Bioline Isolate II RNA Mini Kit according to the manufacturers' instructions. cDNA was reverse transcribed using random hexamer priming and Superscript III (Invitrogen) or Tetro (Bioline) cDNA synthesis kits as specified by the manufacturer. Human RUNX1 isoform specific primers (Table 1) were based on those designed for mouse Runx1 previously. For other genes, TaqMan gene expression probes and reagents (Applied Biosystems) were used for quantitative real-time PCR analysis and GAPDH was used as the reference gene to normalize data.

Culture and Differentiation of hESCs

The HES3 and H9 human embryonic stem cell lines used in these studies were obtained from ES Cell International (now owned by Biotime Inc) and WiCell. The human ESC work was approved by the Monash Medical Centre and Royal Children's Hospital Human Research Ethics Committees. Culture and enzymatic passaging of hESC lines was performed as reported in Ng et al. *Nature Protocols* 3, 768-776 (2008). Differentiation of hESC lines was performed using the spin EB method in APEL medium as described in Ng et al. *Nature Protocols* 3, 768-776 (2008) supplemented for the first 4 days with 20-40 ng/mL recombinant human (rh) bone morphogenetic protein 4 (BMP4, R&D Systems), 20-30 ng/mL rh vascular endothelial growth factor (VEGF, PeproTech) and 20-40 ng/mL rh stem cell factor (SCF, PeproTech), 10-20 ng/mL rh ACTIVIN A (R&D Systems) and 10 ng/mL rh FGF2 (PeproTech) (FIG. 7*a*). Where indicated, cultures included additional CHIR99021 3 μM (Tocris Biosciences), SB431542 3-4 μM (Cayman Chemicals). After 4 days, the differentiation medium on the spin EBs was changed to APEL medium supplemented with 50 ng/mL rhVEGF, 20 ng/mL BMP4, 10 ng/mL FGF2, 50 ng/mL rh SCF and 30 ng/mL rh insulin-like growth factor 2 (IGF2, PeproTech). At d7-8 of differentiation, EBs were transferred onto gelatinized 6-well plates at 20-30 EBs/well in APEL medium including 50 ng/mL rhVEGF, 50-100 ng/mL rh SCF, 25-30 ng/mL rh interleukin (IL)-3 (PeproTech), 25 ng/mL rh IL-6 (PeproTech), 30 ng/mL rh thrombopoietin (TPO, Peprotech), 30 ng/mL rh FLT3 receptor ligand (FLT3L, PeproTech), 3 U/mL rh erythropoietin (EPO, PeproTech), 10 ng/mL FGF2, 50 ng/mL rh SCF and 30 ng/mL rh insulin-like growth factor 2 (IGF2, PeproTech). In later experiments, the IL-3 and EPO were omitted. Medium was changed at least weekly thereafter. For analysis, the EBs were harvested at various time points and dissociated into a single cell suspension using TrypLE Select (Invitrogen) and, for timepoints after d14, Collagenase type I (Worthington) and passaged through a 23-gauge needle as described in Ng et al. *Nature Protocols* 3, 768-776 (2008). Brightfield and fluorescence images comparing RUNX1C$^{GFP/w}$ with RUNX1C$^{GFP/GFP}$ cell cultures shown in FIG. 1*b* were representative of 3 independent experiments. Images of SOX17$^{mCHERRY/w}$RUNX1$^{GFP/w}$ cell culture in FIG. 12*a*-*h* were representative of more than 10 independent experiments and those in FIG. 11*d, e* were representative of 5 independent experiments.

Differentiation of hESCs in Spinner Flasks

To obtain larger yields of haematopoietic cells for d7 T cell assays, after the first 4 days of spin EB culture, the EBs were transferred to 125 ml spinner flasks (Corning Life Sciences) at a density of 60 EBs per 60 ml and cultured for a further 3 days in APEL medium/0.1% methylcellulose supplemented with 50 ng/mL rhVEGF, 3 U/mL rh EPO, 50 ng/mL rh SCF, 10 ng/mL rh FGF2, 30 ng/mL rh TPO, ng/mL rh FLT3L and 30 ng/mL rh IGF2. For analysis, the EBs were harvested and dissociated into a single cell suspension using TrypLE Select and passaged through a 23-gauge needle prior to cell sorting as described in Ng et al. *Nature Protocols* 3, 768-776 (2008).

Flow Cytometry and Cell Sorting

Antibodies directed against the following cell surface antigens (fluorochrome, manufacturer, catalogue number, clone [where known]) were used for staining dissociated EBs for flow cytometric analysis: CD34 (phycoerythrin[pe]-cy7, Biolegend #343515, clone 581) CD45 (brilliant violet, Biolegend #304032, clone H130), VE-CADHERIN (allophycocyanin [apc], Biolegend #348508, clone bv9), CD33 (apc, BD Pharmingen #340474), TIE2 (BD Pharmingen #557039, clone 33), platelet-derived growth factor receptor alpha (PDGFRα) (BD Pharmingen #556001, clone aR1), CD41a (apc, BD Pharmingen #559777, clone HIP8), CD43 (apc, Biolegend #343206, clone 10G7), Glycophorin A (apc, BD Parmingen #551336, clone GA-R2[HIR2]), CD7 (apc, Biolegend #343107, clone 6B7), CD5 (pe-cy7, Biolegend #300622, clone UCHT2), CD4 (apc, BD Pharmingen #555349, clone RPA-T4), CD8 (pe-cy7, Biolegend #344712, clone SK1), CD56 (pe, BD Pharmingen #555516, clone B159), CD90 (apc, BD Pharmingen #559869, clone 5E10), KIT (apc, Biolegend #313206, clone 10D2) and DLL4 (apc, Biolegend #346508, MHD4-46). Unconjugated primary antibodies (TIE2 #557039, clone 33 and PDGFRα #556001, clone aR1, both BD Pharmingen) were detected with anti-mouse secondary antibodies conjugated to apc (BD Pharmingen #550826). Flow cytometric analysis was performed using FACSCALIBUR™ and BD FORTESSA™ analysers and cell sorting was done using FACS DIVA™, FACS ARIA™ and BD INFLUX™ cell sorters (BD Biosciences). Flow cytometry plots shown in FIGS. 2*j*, 3, 6*c*, 11*a,b*, 12*k* and 14*b* were representative of 3-5 independent experiments. Each flow cytometry plot shown in FIG. 15*a-d* relates to one sorting experiment.

T Cell Assays

Flow sorted fractions of d7-8 differentiated SOX17$^{mCHERRY/w}$RUNX1$^{GFP/w}$ cells were co-cultured with OP9 DL4 cells in αMEM (Invitrogen) supplemented with 20% FCS, 10 ng/nl rh FLT3L, 10 ng/mL rh IL7 (PeproTech) and 25 ng/mL rh SCF. Twenty thousand sorted cells were cultured per well of OP9 DL4 on 12-well plates (Costar). Cells were passaged weekly onto fresh OP9 DL4 layers by pipetting the cultures and passing cell through a 40 μM cell strainer. Cultures were analysed by flow cytometry after −21 and −28 days of culture on OP9 DL4. Brightfield and fluorescent images in FIG. 11*d,e* and flow cytometry profiles in FIG. 11*a,b,f,g* were representative of 4 experiments and FIG. 11*j* was representative of 2 experiments.

Colony Forming Assays

Hemangioblast colonies (B1-CFCs) were identified by culturing 5×10$^3$ dissociated cells from d2-4 EBs in serum-free MethoCult (StemCell Technologies) or in a formulation denoted MC-APEL (1% methylcellulose in APEL medium) supplemented with 30 ng/mL VEGF, 50 ng/mL SCF and 3 U/mL EPO, with 20 ng/mL BMP4 and 10 ng/mL FGF2 also added to MC-APEL cultures. For the identification of hematopoietic CFCs emerging at later times, 2-20×10$^3$ differentiated cells were cultured in serum free MethoCult or MC-APEL supplemented with 5 U/mL rh EPO, 50 ng/mL rh VEGF, 30 ng/mL rh IL-3, 30 ng/mL rh IL-6, 25 ng/mL rh GM-CSF, 25 ng/mL rh TPO, 50 ng/mL rh FLT3L and 100 ng/mL rh SCF. Plates were scored for colony formation between 7 and 14 days. Cytocentrifuge preparations of harvested colonies were stained with May-Grunwald-Giemsa (Sigma) according to the manufacturer's instructions. Brightfield and fluorescence images of stained cytocentrifuge preparations shown in FIG. 1*h, i* were representative of 3 independent experiments, and the colonies shown in FIG. 13*a-f* were representative of 5 independent experiments.

Transcriptional Profiling by Illumina Microarray

In the first series of experiments, differentiated cultures of RUNX1$^{GFP/w}$ cells were harvested daily for 8 days. In a second experiment, differentiated cultures of RUNX1$^{GFP/w}$ and RUNX1C$^{GFP/GFP}$ cells were dissociated at d14 and flow sorted based on their expression of CD34 and GFP using a BD INFLUX™ cell sorter. Finally, three cord blood cell samples sorted for CD34 expression were profiled in parallel with the d14 differentiated RUNX1$^{GFP/w}$ and RUNX1C$^{GFP/GFP}$ samples. In all experiments, total RNA was extracted from the collected cell fractions (High Pure RNA Isolation Kit, Roche Applied Science) and RNA quality was assessed using a NanoDrop 2000 analyzer (Thermo Scientific). Total RNA from each fraction was amplified, labeled, and hybridized to Human HT12 v3 and v4 BeadChips0 according to Illumina standard protocols (Illumina) at the Australian Genome Research Facility. Initial data analysis was performed using GenomeStudio Version 2010.2 (Illumina), using average normalization across all the samples. Further data analysis was performed in R/BioConductor using algorithms within the lumi package (function: bgAdjust.affy and quantile normalization). Subsequent data analysis was performed using MultiExperiment Viewer. Principle component analysis was performed to determine the overall relationship between samples. Differentially expressed genes were identified using SAM (Significance Analysis for Microarrays) with a zero false discovery rate. Hierarchical clustering of genes was performed using Pearson correlation with average linkage clustering. Differentially expressed genes were subjected to pathway over-representation and functional clustering analysis using the DAVID public database (Database for Annotation, Visualization and Integrated Discovery). The microarray data reported here are deposited with Array Express, accession number E-MEXP-3356, and Gene Expression Omnibus, accession number GSE64876.

The experiment describing HOX gene expressing in differentiated cultures of d4 MIXL1$^{GFP/w}$ cells used data derived from a previous sorting experiment. The Array Express accession number for this data is E-MEXP-2495.

Transcriptional Profiling Using RNA-Seq

Differentiated SOX17$^{mCHERRY/w}$RUNX1$^{GFP/w}$ cells at d10/11 cultured with or without additional SB/CHIR from d2-4 were flow sorted as shown in FIG. 6*c*. Samples were sent for RNA sequencing at the Australian Genome Research Facility. In total, data from 26 samples from three independent experiments were sequenced. In a second series of experiments, differentiated SOX17$^{mCHERRY/w}$RUNX1$^{GFP/w}$ cells at d18 or d22 cultured with SB/CHIR from d2-4 were flow sorted as shown in FIG. 15*a,b*. The 5 samples from two independent experiments were sequenced on the same run as the human AGM and foetal liver samples (FIG. 15*c,d*) at the University of California, Los Angeles, core sequencing facility. Analysis for both series of sequences was performed by the Murdoch Childrens Research Institute bioinformatics research unit. The STAR aligner (v2.4.0h1) was used to map the 100 bp single end reads to the human reference genome (hg19) in the two pass mapping mode. The uniquely mapped reads were summarized across genes with featureCounts (v1.4.6) using Gencode Release 19 comprehensive annotation. Lowly expressed genes were filtered out (less than one count per million in fewer than two samples), leaving 18,456 genes for further analysis. The data was TMM normalized, voom transformed and differential expression assessed using moderated t-tests from the R Bioconductor limma package, taking into account the different culture medium base. Genes that had a false discovery rate of less than 5% were called significantly differentially expressed for the various comparisons of interest. Gene ontology analysis was performed using DAVID.

Assay for Transposase-Accessible Chromatin with High Throughput Sequencing (ATAC-Seq)

Differentiated SOX17$^{mCHERRY/w}$RUNX1$^{GFP/w}$ cells at d10 cultured with or without additional SB/CHIR from d2-4 were flow sorted as shown in FIG. 6*c* and samples of 5×10$^{4}$ SOX17$^{+}$34$^{+}$ and SOX17$^{-}$34$^{+}$ endothelial cells were processed for ATAC-Seq analysis using a protocol published by Buenrostro et al. *Curr Protoc Mol Biol* 109, 21 29 21-29 (2015) with minor adjustments. Duplicate samples were processed for each of two independent experiments for both control and SB/CHIR differentiations. Nuclei were purified by the addition to the cellular pellet of 250 μl of cold lysis buffer (10 mM Tris-HCl, pH 7.4, 10 mM NaCl, 3 mM $MgCl_2$, 0.1% IGEPAL CA-630), pelleted and resuspended in the transposition reaction mix (Nextera DNA Library Prep Kit, Illumina) and incubated at 37° C. for 30 minutes. Transposed DNA was column purified and used for library amplification with custom made adaptor primers using NEBNext High-Fidelity 2×PCR Master Mix (New England Labs). The amplification was interrupted after 5 cycles and a SyBR green qPCR was performed with 1/10 of the sample to estimate for each sample the additional number of cycle to perform, before saturation was achieved. Total amplification was between 10 and 15 cycles. Purified Libraries were then sequenced using HIseq-2000 (Illumina). The sequencing run for the first experiment used 50 bp PE reads, whilst the second run used 50 bp SE reads. The reads were trimmed using Trimmomatic (v0.33); bases with a Phred score <15 were trimmed from both 5' and 3' ends, and using a sliding window of 5 bp. Reads <30 bp after trimming were discarded. Reads were then mapped to the human genome (hg19) using bowtie2 (v2.1.0). Duplicates were removed with picard (v1.99(1563)). Reads were summarized across hg19 RefSeq genes (including 2 kb upstream) using featureCounts (v1.4.6). The summarised data contained counts for 26,402 genes. Genes with ≥10 counts per million (CPM) in ≥2 samples were retained for further analysis (17,974). The data was TMM normalized. Differential 'accessibility' was assessed using likelihood ratio tests from the R Bioconductor edgeR package. Genes that had a Benjamini-Hochberg false discovery rate of less than 5% were significantly differentially 'accessible' for the various comparisons of interest.

DNA Methylation Analysis Using Illumine Infinium 450 Microarray

Differentiated SOX17$^{mCHERRY/w}$RUNX1C$^{GFP/w}$ cells at d10 cultured with or without additional SB/CHIR from d2-4 were flow sorted as shown in FIG. 6*c* and genomic DNA was extracted from control and SB/CHIR samples of 5×10$^{5}$ SOX17$^{+}$34$^{+}$ and SOX17$^{-}$34$^{+}$ endothelial cells, and SOX17$^{-}$34$^{-}$ stromal cells for two independent experiments. Genomic DNA was bisulphite converted using MethylEasy Xceed kit according to manufacturer's instructions (Human Genetic Signatures, Australia). The conversion efficiency was assessed by bisulphite-specific PCR. Bisulphite DNA hybridization to Illumina Human Methlylation450 (HM450) arrays was carried out at the Australian Genome Research Facility. Data exploration and analysis was performed in R using the Bioconductor packages minfi and limma. The data was normalized using stratified quantile normalization (SQN). Probes with a detection p-value 0.01 in one or more samples were excluded from the subsequent analysis. Non-specific probes and probes with common SNPs at either the CpG or single base extension (SBE) site were also excluded. After filtering, 428,990 probes remained for further analysis. Differential methylation was assessed using moderated t-tests from the R Bioconductor limma package. P values were adjusted for multiple testing using the Benjamini-Hochberg (FDR) method.

Mice

NOD/SCID mice were purchased from ARC (Perth, Australia) and housed in specific pathogen free (SPF) conditions at Monash University Animal Services (MAS, Melbourne, Australia). NOD.Cg-Prkdc$^{scid}$ Il2rg$^{tm1\,Wjl}$/SzJ mice (NOD/SCID/IL2Rγ−/−, NSG) (stock number 005557, The Jackson Laboratory) were bred at MAS in SPF conditions. The colony was regularly checked for γ-c deficiency by PCR according to the Jackson Laboratory protocol. The Monash University institutional animal ethics committee approved all animal protocols, and experiments were carried out under its guidelines for the care and use of laboratory animals.

Human Tissue Collection, Processing and Sequencing i) AGM Tissue Procurement and Processing This study was performed in accordance with institutional guidelines and was approved by the local research ethics committee (University of Tubingen IRB #406/2011B02, #710/2012BO2 and #690/2013BO2). Human first trimester tissue (5 weeks of gestation) was obtained from an electively aborted fetus following informed consent and de-identification. After procurement, the tissues was immediately washed in sterile Dulbecco's phosphate buffered saline (DPBS, Invitrogen, Cat #14190-169), placed in medium (DMEM/F12, Gibco, Cat #31330-095) that was supplemented with 5% foetal bovine serum (ThermoFisher, Cat #16000-044), 1% Penicillin-Streptomycin (Gibco, Cat #15140-122) and 2.5 μg/mL Amphotericin B (Sigma Aldrich, Cat #A9528), and processed for gene expression analyses within 48 hours. The embryo was dissected to isolate the AGM region. The tissue was digested in 2.5 U dispase (Gibco), 90 mg collagenase A (Worthington), and 0.075 mg DNase I (Sigma) per ml in PBS containing 10% FBS, for 90 minutes at 37° C. Cells were then disaggregated by pipetting, and filtered through a 70 μm cell strainer.

ii) Foetal Liver Tissue Collection and Processing

Foetal liver was de-identified, discarded material obtained from elective termination of a second trimester pregnancies following informed consent. Specimen age for this study (17 weeks) is denoted as developmental age, two weeks less than gestational age, and was determined by ultrasound or estimated by the date of the last menstrual period. Tissues were harvested into PBS 5% FBS (Hyclone), Ciprofloxacin HCl (10 ng/mL, Sigma), amphotericin B (2.50 μg/mL, Invitrogen), 1% penicillin/streptomycin, transported on ice and processed the same day. Tissues were mechanically dissociated using scalpels and syringes. Mononuclear cells were enriched on a Ficoll layer according to manufacturer's protocol (GE Healthcare Biosciences AB) and strained through a 70 μm mesh.

iii) Antibody Staining and Flow Cytometric Sorting

Cells were stained with the following antibodies: human-CD45-APC-H7 cl.2D1 (Biolegend 368516; 1:100), CD34-APC cl. 581 (BD 555824; 1:20), CD90-BV421 cl. 5E10 (BD 562556; 1:100), CD38-PE-Cy7 cl. HIT2 (BD 560677; 1:100), CD43-FITC c1.1G10 (BD 555475; 1:20), GPI-80-PE cl. 3H9 (MBL D087-5; 1:50). The indicated populations (FIG. 15*c, d*) were sorted into RLT buffer (Qiagen) using a BD FACS Aria cell sorter and snap frozen at −80° C.

iii) RNA Extraction and Library Preparation and RNA-Sequencing.

Total RNA from 500-2000 sorted cells was extracted using the RNeasy Mini kit (Qiagen) and library was constructed using Ovation Rna-seq system System v2 (Nugen), followed by KAPA LTP Library Preparation Kit. Libraries were sequenced using HIseq-2000 (Illumina) to obtain single end 50 bp long reads. Demultiplexing of the reads based on the barcoding was performed using in house Unix shell script. Sequencing was performed at the University of California, Los Angeles, core sequencing facility.

Cord Blood Cells

Samples of human umbilical cord blood from healthy subjects were obtained from the Mercy Hospital for Women, Studley Road, Heidelberg, Victoria 3084, under auspices of the hospital Human Research Ethics Committee. Mononuclear cells or flow sorted $CD34^+$ cells were isolated and cryopreservation for subsequent use in transcriptional profiling or transplantation assays.

Analysis of Bone Marrow Homing of CFSE-Labeled Differentiated Cells i) CFSE Labeling of Differentiated hPSCs Differentiated $RUNX1C^{GFP/w}$ and $RUNX1C^{GFP/GFP}$ cells were flow sorted at d14 based on CD34 and GFP expression, or at earlier time points on the basis of CD34 and CD41 expression. Viable cells were labeled with 5-(and 6)-carboxyfluorescein diacetate succinimidyl ester (CFSE; Molecular Probes). Briefly, cell populations were resuspended in PBS 0.5% heat-inactivated (HI) foetal calf serum (FCS; Hyclone, Logan, UT, USA) at a density of $1\times10^6$ cells/mL and pre-incubated at 37° C. for 3 minutes. CFSE was diluted to 5 mM in dimethyl sulfoxide (DMSO) and then to 5 μM in PBS. CFSE was added to the cells to give a final concentration of 0.5 μM, and the dye solution/cell mixture was incubated at 37° C. for a further 10 minutes. Staining was stopped by adding 10 times the dye solution/cell volume of ice-cold PBS containing 20% FCS.

ii) Irradiation of Immunodeficient Mice

The ability of cells to reconstitute haematopoiesis was analyzed in NSG mice receiving a near-lethal dose of irradiation (2.75 Gy), delivered from two opposing $^{137}Cs$ sources (Gammacell 40; Atomic Energy of Canada, Ottawa, ON, Canada) at a dose rate of 1.4 Gy/minute.

iii) Cell Homing

Sorted, CFSE-labeled cells were transplanted in 0.2 ml of PBS by injection into the lateral tail vein of near-lethally irradiated NSG mice, with 3 recipients per sorted cell fraction, for each of 4 experiments. As a result, the data accumulated are the result of multiple sorts at each time point. On average, $1\times10^5$ sorted, $CFSE^+$ cells were co-injected with $2\times10^6$ irradiated (15 Gy), unlabelled human cord-blood mononuclear cells. The homing ability was analysed 15 hours post-transplant. For the analysis of homing, bone marrow samples were prepared from individual mice as described below. The analysis of the proportion of $CFSE^+$ donor cells in each fraction was performed using the number of live white blood cells (WBC) as the denominator for the total number of cells analysed by flow cytometry. No statistical method was used to predetermine sample size and the experiments were not randomized. The investigators were not blinded to allocation during experiments and outcome assessment.

iv) Isolation of Hematopoietic Cells

NSG mice were humanely killed by cervical dislocation. Bone marrow was routinely collected from femurs, tibiae and iliac crests. These bones were thoroughly ground in a mortar and pestle in phosphate-buffered saline (PBS) supplemented with 2% heat inactivated FCS. Bone fragments were washed, and the supernatant cell suspension was filtered through a 40 μM filter (Becton Dickinson, NJ, USA). The marrow was centrifuged (400 g, 5 minutes) and resuspended in fresh buffer. The cell supernatant was re-filtered through a 40 μM filter and diluted to $1\times10^7$ cells/mL PBS supplemented with 2% heat inactivated FCS (buffer). Donor cells labeled with CFSE that homed to the bone marrow were identified by flow cytometry.

Statistical Analysis

Experiments were analysed using GraphPad Prism versions 5 and 6 (GraphPad Software Inc.) and Microsoft Excel (Microsoft corporation). Tests for statistical significance are listed with each experiment and included two sided Student's t test for paired analyses and ANOVA for experiments with multiple comparisons of one or more grouped variables, accompanied by the post-tests (Dunnett, Tukey, Holmes-Sidak) indicated as appropriate by the software. No statistical method was used to predetermine sample size.

Results

RUNX1C is Expressed in Human hESC-Derived Haematopoietic Cells

To identify haematopoietic stem/progenitor cells during hPSC differentiation, reporter lines targeting GFP to the RUNX1C locus (FIG. 1*a* and FIG. 2*a-c*) were generated. This choice was based on observations that Runx1c marked mouse haematopoietic progenitor cells, and that disruption of one allele did not adversely affect haematopoiesis. Differentiation of heterozygous $RUNX1^{GFP/w}$ cells as spin embryoid bodies (EBs) in APEL medium supplemented with haematopoietic growth factors was indistinguishable from differentiation of unmodified cells. GFP was restricted to RUNX1C-expressing cells, validating the reporter line (FIG. 1*b* and FIG. 2*d*). $RUNX1C^+$ cells appeared between differentiation day (d) 8 and 11, initially expressing CD34, although by d15 most $RUNX1C^+$ cells expressed CD45 (FIG. 1*c,d*). They did not express mesodermal (PDGFRα) or vascular (TIE2/TEK) markers (FIG. 1*c,d*), confirming the haematopoietic specificity of RUNX1C expression.

Sequential expression of the haematopoietic cell surface markers CD34, CD43 and CD41, antedated RUNX1C expression (FIG. 3*a,b*). The earliest $RUNX1C^+$ cells expressed these markers, and by d16 many $RUNX1C^+$ cells co-expressed VE-CADHERIN and CD45, considered markers of 'pre-HSCs' in the mouse AGM (FIG. 3*c,d*).

Figure 1:
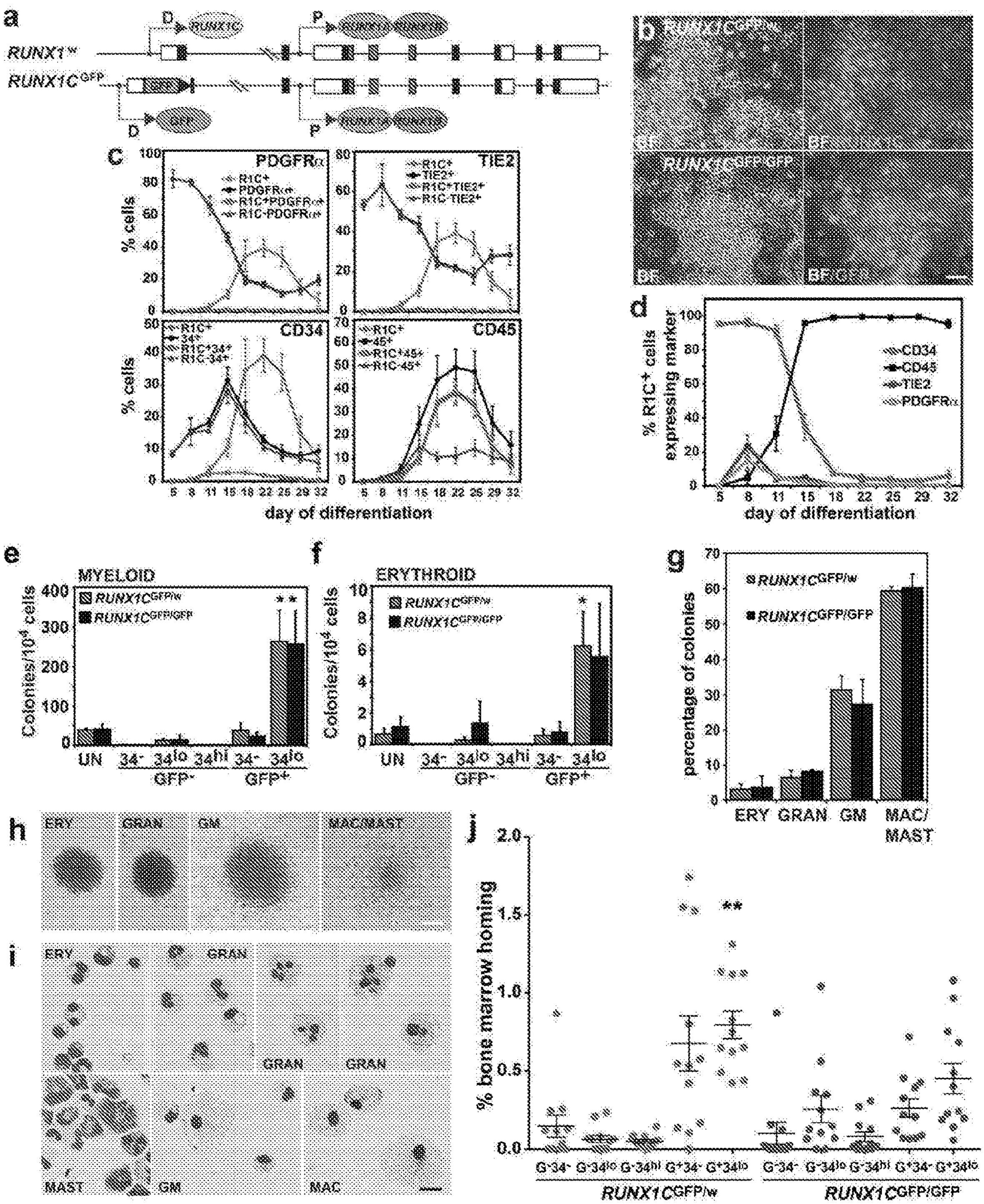
FIG. 1. Characterization of RUNX1C$^{GFP/w}$ and RUNX1C$^{GFP/GFP}$ hESCs.

RUNX1C Expression Identifies $CD34^+$ Cells with Clonogenic and Bone Marrow Homing Ability Given the hematopoietic specificity of the RUNX1C isoform, homozygous $RUNX1C^{GFP/GFP}$ cells to assess whether RUNX1C was required for human haematopoiesis (FIG. 2*e-h*) were generated. $RUNX1^{GFP/w}$ and $RUNX1C^{GFP/GFP}$ lines displayed similar morphology, GFP and cell surface marker expression (FIG. 1*b* and FIG. 3*e-h*). Clonogenic frequency was enriched in $GFP^+34^{lo}$ populations derived from both $RUNX1C^{GFP/w}$ and $RUNX1C^{GFP/GFP}$ cultures, with similar colony morphology in each case (FIG. 1 *e-i* and FIG. 3*i*). These experiments indicated that although RUNX1C expression marked $CD34^+$ clonogenic cells, these precursors formed independently of RUNX1C.

Homing to bone marrow of d14 differentiated cells; an ability needed for long-term engraftment was evaluated. Significant homing was observed in $GFP^+CD34^{lo}$ cells sorted from the heterozygous, but not the null line (FIG. 1*j*). The frequency of bone marrow homing (0.79±0.09%) was approximately half that reported for $CD34^+$ cells in cord blood (CB) (1.7%). These results demonstrate that bone marrow homing activity resides in RUNX1C$^{+}34^{lo}$ cells, and that this is compromised in the absence of RUNX1C. However, despite their clonogenic activity and bone marrow homing ability, the RUNX1C$^{+}34^{lo}$ cells were unable to engraft.

hPSC-Derived and Cord Blood Progenitor Cells Display Discordant HOX Gene Expression To explore the reasons for engraftment failure of hPSC-derived hematopoietic cells, transcriptional profiles of cells sorted from d14 RUNX1C$^{GFP/w}$ and RUNX1C$^{GFP/GFP}$ EBs with repopulation-competent CB CD34$^{+}$ cells were compared. RUNX1C$^{GFP/w}$ and RUNX1C$^{GFP/GFP}$ EBs were transcriptionally nearly identical, judged by hierarchical clustering of sorted fractions, scatter plot analysis, Pearson correlation coefficients (FIG. 4*a-e*) and the expression of transcription factors and cell surface proteins (FIG. 5*a*). To explain the functional differences between hPSC- and CB-derived CD34$^{+}$ cells, differentially expressed genes were sought, identifying 273 probes (249 genes) up-regulated and 292 probes (270 genes) down-regulated in CB CD34$^{+}$ cells. These up-regulated CB CD34$^{+}$ genes with a list of genes expressed in CB HSCs were compared. Thirty-two genes in common, including transcription factors (BCL11A, HLF, HOXA5, HOXA9 and HOXA10), cell surface receptors (FLT3, PROM, IGLL1, HTR1F and RYR3), and signaling pathway intermediates (CTNND1, GAB2, SH3BP4, PRKACB and ABL1) (FIG. 5*b,c*) were identified. Given the early developmental divergence of the primitive and definitive haematopoietic programs, it was hypothesized that expression of transcription factors influencing early cell fate decisions might best mark cells committed to definitive haematopoiesis. Although both BCL11A and HLF are expressed in foetal haematopoietic stem and progenitor cells, they do not regulate early cell fate. Moreover, neither gene was selectively expressed in nascent mesoderm (FIG. 4*h,i*), arguing against a role in directing definitive haematopoietic commitment.

Conversely, HOXA5, HOXA9 and HOXA10 are expressed in the primitive streak and also in HSCs. Furthermore, deletion of Hoxa9 or the whole Hoxa cluster in mesoderm is associated with severe haematopoietic defects. Lastly, failure to express HOXA genes was a major difference between hPSC-derived haematopoietic cells and CB CD34$^{+}$ cells (FIG. 4*f*).

HOXB, but not HOXA, genes were first expressed at d2-3 of hPSC differentiation, coincident with the expression of MIXL1 and BRACHYURY (T) primitive streak genes, and the CDX genes that regulate HOX expression (FIG. 4*g,h*). Analysis of d4 differentiated cultures confirmed that CDX and HOXB genes were expressed in MIXL1$^{+}$ cells (FIG. 4*i*). Therefore, it was hypothesized that HOXA gene expression could be used as a surrogate marker to identify culture conditions that generated definitive blood cells.

HOXA Expression in Mesoderm is Induced by a Combination of WNT Agonist and ACTIVIN Antagonist The effects of adding the WNT agonist, CHIR99021 (CHIR), and the ACTIVIN receptor-like kinase (ALK) inhibitor, SB431542 (SB), from differentiation days 2 to 4, the period during which HOX gene expression is initiated (FIG. 4*g*) were explored. Compared with control cultures, SB addition increased HOXA3, HOXA7 and HOXA9 expression, whilst CHIR increased HOXA9 and HOXA10 expression (FIG. 5*d* and FIG. 6*a*). When the two molecules were combined (denoted SB/CHIR), greater up-regulation of HOXA expression was observed than with either alone (FIG. 5*d* and FIG. 6*a*). Mediating the changes in HOXA expression, transient up-regulation in CDX gene expression (FIG. 5*d, e* and FIG. 6*b*) were observed. Treatment with SB/CHIR also suppressed primitive haematopoiesis, evidenced as a reduction in CD43$^{+}$ haematopoietic cells at d7 (FIG. 5*f*).

RNA-Seq Analysis Confirms Enhanced HOXA Gene Transcription as a Major Consequence of SB/CHIR Treatment It was hypothesized that the SB/CHIR protocol (FIG. 7*a*) would pattern the haemogenic endothelium from which definitive blood cells arose. To facilitate visualization of the endothelial to haematopoietic transition, a dual reporter line (SOX17$^{mCHERRY/w}$RUNX1C$^{GFP/w}$) in which mCHERRY was targeted to SOX17 (given its expression in mouse AGM), and GFP to RUNX1C (FIG. 2*i,j*) was generated.

The transcriptional profiles of d10 control and SB/CHIR differentiated SOX17$^{mCHERRY/w}$RUNX1C$^{GFP/w}$ cells were compared, sorting cultures on CD34, CD43 and SOX17 expression into haematopoietic (43$^{+}$), endothelial (SOX17$^{+}$34$^{+}$ and SOX17$^{-}$34$^{+}$) and CD34$^{-}$ adherent cells (SOX17$^{+}$34$^{-}$ and SOX17$^{-}$34$^{-}$) (FIG. 6*c*). Multidimensional scaling (MDS) plots showed that control and SB/CHIR samples with the same surface phenotype expressed similar genes, and clustered together in the first two dimensions, with culture treatment separating control from SB/CHIR populations in the third and fourth dimensions (FIG. 7*b, c*). In keeping with this, many of the genes enriched in CD34$^{+}$ endothelial fractions were common to both control and SB/CHIR culture conditions (FIG. 6*d, e*). Genes differentially expressed between SB/CHIR and control cultures were observed in all populations, with many of the differentially transcribed genes common to both SOX17$^{+}$ and SOX17$^{-}$ fractions (FIG. 6*f, g*).

HOXA cluster genes were up-regulated in all populations sorted from SB/CHIR cultures (FIG. 7*d* and FIG. 8*a-g*). More highly transcribed members included HOXA5 and HOXA9-HOXA13, especially in the endothelial fractions (FIG. 7*d*). Furthermore, the gene ontology terms enriched in genes differentially expressed in SB/CHIR derived endothelia reflected embryonic patterning and almost exclusively comprised homeobox genes (FIG. 7*e*). These data confirmed that HOXA genes were major targets up-regulated by SB/CHIR.

Endothelia from SB/CHIR Treated Cultures Express Genes Indicative of Aortic Fate To define the endothelium developing under control and SB/CHIR conditions, these populations were examined for the expression of genes defining umbilical cord arterial and venous endothelia (FIG. 8*h*). At this differentiation stage, arterial and venous genes were transcribed in all d10 endothelia irrespective of SOX17 expression or culture conditions (FIG. 8*h*), suggesting that the arterial-venous lineage bifurcation occurs later than d10 of hPSC differentiation.

Importantly, genes were not identified whose expression indicated that SB/CHIR directed endothelium towards an aorta-like fate, from which definitive haematopoeitic cells could subsequently arise. The angiotensin II type 2 receptor (AGTR2), expressed in foetal rat aorta, was transcribed in SB/CHIR patterned SOX17$^{+}$ endothelium, whilst the type 1 receptor (AGTR1) was expressed in control endothelia (FIG. 7*f*). The transcription factor NKX2-3, and matrix metallopeptidase 9 (MMP9), both expressed in spleen but not in the major arteries, were more highly expressed in control endothelium (FIG. 7*g*). Similarly, control endothelium expressed both FGF23 and its co-receptor, KLOTHO, whilst SB/CHIR SOX17$^{+}$ endothelium expressed only KLOTHO, in keeping with human aorta (FIG. 7*h*). SELEC- TINS were also differentially expressed, with SELE up-regulated in SB/CHIR endothelium and SELP and SELL more highly expressed in control endothelia (FIG. 7*i*). In zebrafish, SELE expression localizes to sites of definitive haematopoiesis in the posterior trunk and the AGM-like caudal hematopoietic tissue. Synthesis of retinoic acid, dependent upon ALDH1A2 expression, is a hallmark of definitive haemogenic endothelium in the mouse AGM. ALDH1A2 expression was elevated in SB/CHIR endothelium, with higher ALDH1A1 levels in control endothelia (FIG. 7*j*). Taken together, these data indicate that aorta-like endothelial precursors were selectively generated in SB/CHIR cultures.

The transcriptional programs of the SOX17$^+$34$^+$ and SOX17$^-$34$^+$ SB/CHIR derived endothelial populations were then compared. It was observed that HOXA and NOTCH pathway genes were more highly expressed in SOX17$^+$34$^+$ cells, whilst haematopoietic transcription factors and surface markers were up-regulated in SOX17$^-$34$^+$ populations (FIG. 6*a*). Using limit dilution experiments, the haemogenic potential of SB/CHIR endothelia (CD34$^+$CD43$^+$RUNX1C$^-$ SOX17$^\pm$), sorted on SOX17 expression into SOX17-bright, SOX17-dull and SOX17-negative fractions (FIG. 9*b*) were compared. Populations were also stratified on the basis of CD73 expression, because prior studies have shown that CD73 distinguishes vascular from haemogenic endothelium. As expected, haematopoietic cells only arose from CD73$^-$ endothelium, with the highest frequency seen in SOX17-dull and -negative fractions (FIG. 9*b* and Table 2). These data identify a reciprocal relationship between SOX17 expression and haemogenic capacity, and suggest that this gene may be down regulated during the endothelial-haematopoietic transition.

TABLE 2

Haemogenic precursor frequency in d10 SB/CHIR endothelium. See also FIG. 9b.

| Cell phenotype | Cells/well | Haematopoietic cells | Clonal frequency* |
|---|---|---|---|
| 73$^+$34$^{++}$43$^-$ | | | |
| SOX17$^{++}$ | 1 | 0/288 | <1/100,000 |
| | 3 | 0/288 | |
| | 10 | 0/240 | |
| | 1000 | 0/8 | |
| | 5000 | 0/8 | |
| | 10000 | 1/8 | |
| SOX17$^+$ | 1 | 0/24 | <1/100,000 |
| | 3 | 0/24 | |
| | 1000 | 0/5 | |
| | 5000 | 0/3 | |
| SOX17$^-$ | 1 | 0/288 | <1/100,000 |
| | 3 | 0/288 | |
| | 10 | 0/240 | |
| | 1000 | 0/5 | |
| 73$^{lo/-}$34$^{++}$43$^-$ | | | |
| SOX17$^{++}$ | 1 | 0/192 | 1:509 |
| | 3 | 1/288 | |
| | 10 | 2/120 | |
| | 300 | 3/8 | |
| | 1000 | 7/8 | |
| | 5000 | 4/4 | |
| SOX17$^+$ | 1 | 0/24 | 1:54 |
| | 3 | 0/24 | |
| | 10 | 8/48 | |
| | 300 | 6/6 | |
| | 1000 | 2/2 | |
| SOX17$^-$ | 1 | 0/192 | 1:65 |
| | 3 | 0/288 | |
| | 10 | 2/136 | |
| | 300 | 6/6 | |
| | 1000 | 2/2 | |

*Poisson distribution was used to calculate clonal frequency, which was equated to the cell number giving 37% negative wells.

Adherent CD34$^-$ cells from control and SB/CHIR cultures expressed a host of growth factor genes including WNT3, WNT5A, BMP4, JAG1, KITLG and VEGF. Additional genes such as CXCL12, DLL1, FGF2, and ALDH1A2 were selectively up-regulated in SB/CHIR patterned CD34 cells, highlighting the potential supportive role that these cells might play (FIG. 7*k*).

A Pulse of SB/CHIR Increases Chromatin Accessibility of HOX Cluster Genes

The mechanisms underpinning the sustained increase in HOXA expression induced by SB/CHIR were explored. Evaluation of CpG methylation in d10 SOX17$^+$ and SOX17$^-$ endothelia and SOX17$^-$34$^-$ cells by microarray showed that the HOX clusters were hypomethylated in all populations in both treatment groups, indicating that changes in methylation did not play a major role in HOXA gene induction by SB/CHIR (FIG. 9*c* and FIG. 10*a,b,d-f*). This analysis was extended using the Assay for Transposase-Accessible Chromatin with high throughput sequencing (ATAC-Seq), to determine whether HOX gene loci differed in chromatin accessibility between control and SB/CHIR-treated endothelia. MDS plots showed that samples clustered by phenotype and by culture treatment (FIG. 10*c*). Of the loci that were more accessible in SB/CHIR cultures, 13 in SOX17$^+$ and 22 in SOX17$^-$ endothelium mapped to HOX clusters, with 8 and 10 respectively localized to the HOXA cluster. These data indicate that a more accessible chromatin configuration underpinned the enhanced HOXA gene expression in response to SB/CHIR.

Correlating the RNA-Seq and ATAC-Seq experiments revealed that the increased chromatin accessibility was accompanied by selective gene expression (FIG. 9*c* and FIG. 10*d-f*). For example, the highest expression across the HOXA cluster induced by SB/CHIR was observed for HOXA9 and HOXA10. These data suggest that the CDX genes induced by SB/CHIR (FIG. 5*d, e* and FIG. 6*a, b*) predominantly up-regulated posterior HOXA genes, and that other factors were needed to enhance anterior HOXA transcription.

Overall, these analyses indicate that SB/CHIR changes the transcriptional profile of multiple cell populations within treated cultures, opening chromatin in the HOXA cluster and generating SOX17$^+$ endothelial cells that bear markers of human aortic cells.

T Cells are Generated from SB/CHIR and Control Cultures

SB/CHIR treatment was correlated with T lymphoid differentiation capacity of d7 endothelial (SOX17$^-$34$^+$ and SOX17$^+$34$^+$) and haematopoietic (RUNX1C$^-$43$^+$ and RUNX1C$^+$34$^{lo}$) cells using previously published protocols (FIG. 11*a-c*). Endothelial cells from both control and SB/CHIR cultures formed an adherent layer of SOX17-expressing cells on OP9 DL4 cells prior to lymphoid development (FIG. 11*d,e*). All sorted populations generated CD45$^+$CD56$^-$CD7$^+$CD5$^\pm$ T lymphoid progenitors and CD45$^+$CD56$^{hi}$CD7$^\pm$ NK cells, although production of CD4$^+$ CD8$^+$CD56$^-$ T cells appeared to be greater from SB/CHIR treated cultures (FIG. 11*f-j*). These data are consistent with studies reporting generation of T cells using a range of protocols and with observations that murine T cell precursors arise from two distinct origins—from the pre-circulation mouse yolk sac and from the AGM.

Haemogenic SOX17$^+$ Vascular Structures Arise Exclusively from SB/CHIR Treated EBs When d7 EBs were transferred onto MATRIGEL™-coated plates, it was that observed SOX17$^+$ vascular structures from d10, exclusively in SB/CHIR cultures (FIG. 12*a*). Haematopoietic cells were abundant in control cultures but virtually absent from SB/CHIR treated cultures, consistent with the suppression of primitive haematopoiesis (FIG. 12*a* and FIG. 6*c*). By day 14, extensive SOX17$^+$ vessels were present in SB/CHIR cultures and RUNX1C$^+$ blood cells were evident (FIG. 12*b*). Over subsequent days, some regions of the SOX17$^+$ vessels expanded and RUNX1C$^+$ and RUNX1C$^+$ blood cells were seen within, and emerging from, these structures (FIG. 12*c-h*). Marrying these findings with RNA-Seq data showing a gene expression pattern in d10 SOX17$^+$ vasculature predictive of a future aorta-like fate, suggested that the regional generation of blood cells resembled the emergence of haematopoietic cells from the AGM.

SB/CHIR Cultures Retain Cells Expressing Haematopoietic Stem/Progenitor Cell Surface Markers and Progenitors for Erythroid Colonies Expressing Foetal Globin Genes Differences between control and SB/CHIR cultures were not restricted to the SOX17$^+$ endothelium. The percentage of viable haematopoietic cells, compared to controls, was increased in SB/CHIR cultures. These cultures also included increased numbers of CD34$^+$ cells, some of which co-expressed foetal liver HSC markers such as ACE and GPI80 (VNN2) or the FCER1A receptor, up-regulated in CB CD34$^+$ cells (FIG. 12*i*-1).

Clonogenic assays from d20-33 revealed that CFCs persisted in SB/CHIR cultures, with an initial myeloid preponderance followed later by predominantly erythroid or mixed colonies, frequently forming multifocal bursts (FIG. 13*a-h*). When MATRIGEL™ was included in the methylcellulose colony cultures, the erythroid colonies were frequently seen in close apposition to SOX17 cystic structures (FIG. 13*e,f*), consistent with the observation that the non-hematopoietic component of SB/CHIR cultures expressed supportive growth factors.

Globin gene expression between colonies derived from d23-26 SB/CHIR cultures and primitive haemangioblast colonies generated from control cultures at d4 were compared, and marked reduction in EPSILON globin and increase in BETA globin expression in the former (FIG. 13*i,j*) was observed, suggesting that cells arising following SB/CHIR treatment represented a later developmental stage.

HOXA9 and HOXA10 expression levels in the haematopoietic and stromal components of d23-26 SB/CHIR cultures and the d39-44 derived haematopoietic colonies were similar to in vitro differentiated CB CD34$^+$ cells, whilst minimal HOXA expression was seen cells from control cultures (FIG. 13*k*). This demonstrated that HOXA expression induced by SB/CHIR persisted for over 40 days in vitro. In control cultures, a yolk sac-type of embryonic globin gene expression pattern persisted (FIG. 13*l*), whilst in cells derived from SB/CHIR cultures, the GAMMA/EPSILON ratio was elevated, reflecting down-regulation of EPSILON globin, the first of the β globin switches. Moreover, in the SB/CHIR derived haematopoietic colonies, the ALPHA/ZETA ratio was increased, indicating that down-regulation of ZETA globin represented a separate switch from embryonic to adult a globin (FIG. 13*l*). These data place the late SB/CHIR colonies at a foetal-like developmental stage between the yolk sac-like embryonic precursors and perinatal CB cells. The suppression of EPSILON correlated with expression of KLF1 and BCL11A, genes associated with the silencing of GAMMA globin. It was observed that SB/CHIR cultures up-regulated both genes, similar to CB (FIG. 13*m*). These results (summarized in FIG. 13*n*) indicate that the cultures encompassed two globin switches—EPSILON to GAMMA and ZETA to ALPHA—that were dependent upon SB/CHIR mesodermal patterning.

Nascent Haematopoietic Progenitors Transiently Co-Express SOX17 and RUNX1C.

It was hypothesized that haematopoietic progenitors emerging from the SOX17$^+$ vascular structures would progress from a SOX17$^+$RUNX1C$^-$ phenotype, via a SOX17$^+$ RUNX1C$^+$ intermediate, to a more mature SOX17$^-$ RUNX1C$^+$ phenotype. In support of this, CHERRY$^+$GFP$^+$ haematopoietic cells were observed by microscopy, a result confirmed by flow cytomtery (FIG. 14*a,b*). Flow cytometric analysis also showed that the frequency of SOX17$^+$ RUNX1C$^-$ cells decreased between day 14 and 26, whilst the percentage of SOX17$^-$RUNX1C$^+$ increased (FIG. 14*c*). Phenotype was correlated with clonogenic frequency, assaying cells sorted on the basis of SOX17, RUNX1C, CD34 and the stem/progenitor cell marker, KIT. Clonogenic cells at d14 and d18 were predominantly myeloid, and enriched in the SOX17$^+$RUNX1C$^+$34$^+$ and SOX17$^-$RUNX1C$^+$34$^+$ populations. KIT expression, which was low at these time points, did not enrich further for clonogenic cells (FIG. 14*d*). In d22 and d26 cultures, however, KIT expression strongly selected for clonogenic cells for all SOX17 and RUNX1C phenotypes (FIG. 14*d*). Whilst the SOX17$^+$RUNX1C$^-$34$^+$ KIT$^+$ colony forming cells remained myeloid restricted, increasing numbers of multifocal erythroid and mixed colonies emerged from SOX17$^+$RUNX1C$^+$34$^+$KIT$^+$ and SOX17$^-$RUNX1C$^+$34$^+$KIT$^+$ populations (FIG. 14*d*). This later emergence of erythroid colonies was consistent with the timecourse observed with unsorted cultures (FIG. 13*g*).

hPSC-Derived Stem/Progenitor Cells Share Expression of Key Haematopoietic Genes with Human AGM.

The transcriptional profiles of SOX17 and RUNX1C populations from SB/CHIR cultures with populations that included developing human HSCs sorted from a human 5 week AGM (equivalent to mouse E11.5) and a human 17 week foetal liver (FL) were compared. The AGM sample was fractionated on CD34, CD90 and CD43 into 34$^+$90$^+$43$^-$ endothelium (AGM En), a 34$^+$90$^+$43$^+$ population of cells transiting from haemogenic endothelium to haematopoietic stem/progenitors (AGM S/P), and 34$^+$90$^-$43$^+$ committed progenitor cells (AGM Pr1). The CD43$^+$ CD45$^+$ FL sample was sorted further on CD34, CD38 and CD90 to enrich for haematopoietic stem/progenitor cells (34$^+$38$^{lo/-}$90$^+$) (FL S/P). Day 18 hPSC samples included similar populations to the AGM, with SOX17$^+$RUNX1C$^+$34$^+$90$^+$ endothelial (d18 S$^+$R$^-$ En), SOX17$^+$RUNX1C$^+$34$^+$90$^+$ haematopoietic stem/progenitor (d18 S$^+$R$^+$ S/P), and SOX17$^-$RUNX1C$^+$34$^+$90$^{lo}$ committed progenitor (d18 S$^-$R$^+$Pr1) fractions. In addition, d22 samples were included, enriched for committed progenitor cells, SOX17$^+$RUNX1C$^+$34$^+$KIT$^+$ (d22 S$^+$R$^+$Pr2) and SOX17 RUNX1C$^+$34$^+$KIT$^+$ (d22 S$^-$ R$^+$ Pr3) (FIG. 15*a-d*). The RUNX1C$^+$ populations from day 18 and day 22 also expressed CD45 and CD43.

If the differentiation cultures indeed generated AGM-like haematopoiesis, it was anticipated that the day 18 S$^+$R$^-$ En and S$^+$R$^+$ S/P cells would share expression of key genes with the AGM En and S/P fractions, whilst the more mature day 18 $S^-R^+$Pr1, day 22 $S^+R^+$ Pr2 and $S^-R^+$ Pr3 samples might show greater similarity to the AGM Pr1 committed progenitors.

It was observed that most hematopoietic and vascular cell surface markers expressed on FL S/P cells were shared with AGM S/P and d18 $S^+R^+$ S/P cells (FIG. 16*a*). However, a cohort of markers shared by the AGM En and S/P fractions and the d18 $S^+R^-$ En and $S^+R^+$ S/P cells were poorly expressed on FL S/P and inconsistently present on committed progenitor cells. These included endothelial and haematopoietic genes, integrins, growth factor receptors (APLNR, LIFR, OSMR), and the previously identified aorta markers KLOTHO and E-SELECTIN (FIG. 7*h,i*). Similarly, a group of haematopoietic transcription factors poorly expressed on FL S/P were more highly expressed by the AGM En and S/P fractions and d18 $S^+R^-$ En and $S^+R^+$ S/P cells, including F-box SOX genes, HIF3A, MEIS2 and GATA6 (FIG. 16*b*).

Very similar patterns of gene expression in corresponding AGM and d18 hPSC En and S/P samples were observed for the NOTCH, BMP/TGFβ and WNT signaling genes (FIG. 16*c-e*). WNT expression was strongly biased to the non-canonical pathway, known to antagonize canonical signals, consistent with the argument that WNT signals are inhibited to enable emergence of HSCs from the mouse AGM. The retinoic acid synthesis enzyme ALDH1A1 was more highly expressed in FL S/P cells, whilst ALDH1A2 was preferentially expressed in the AGM En and S/P and d18 $S^+R^-$ En and $S^+R^+$ S/P cells. Several retinoic acid pathway genes were more highly expressed in AGM En and S/P than in d18 $S^+R^-$ En and $S^+R^+$ S/P cells (FIG. 16*f*). Similarly, HOXA2-HOXA4 genes remained more highly expressed in AGM En and S/P than in d18 $S^+R^-$ En and $S^+R^+$ S/P cells (FIG. 15*e* and FIG. 16*h*). Significantly, patterns of globin gene expression were virtually identical in AGM and d18 hPSC samples, with residual EPSILON globin observed in Pr1 fractions (FIG. 16*g*).

Finally, the list of genes differentially expressed between CB and the $HOXA^-$ $RUNX1C^+34^+$ cells (FIG. 5*c*) was revisited. Most of the genes (29/32) were expressed in FL S/P cells, indicating considerable similarity with CB. Day 18 $S^+R^-$ En and $S^+R^+$ S/P cells bore greater similarity to the AGM samples than to FL S/Ps, with 15-20 of the 32 genes expressed in the AGM En, S/P and Pr1 populations and 12-26 expressed in the three d18 hPSC samples (FIG. 15*f*). Taken together, the transcriptional profiling data argue strongly that the in vitro derived d18 $S^+R^-$ En and $S^+R^+$ S/P cells represent emerging definitive haematopoietic cells at a similar developmental stage to human AGM En and S/P populations.

Expression of Anterior and Posterior HOXA Genes Requires a Combination of Retinoic Acid Signaling and SB/CHIR hPSCs were differentiated in medium supplemented with CHIR99021, BMP4, VEGF, SCF, ACTIVIN A and FGF2 (denoted CH BVSAF in FIG. 29) from d0-4, or with an additional pulse of SB431542 and CHIR99021 (denoted SB CHIR in FIG. 29) from d2-4. Cultures also were treated with the retinoic acid analogue EC23 at 0, $10^{-5}$ M or $10^{-7}$ M concentrations from d2-4 (denoted 0, 10-5 and 10-7, respectively in FIG. 29). Samples were harvested at d0, d2, d4 and d7 of differentiation and cDNA was analysed for HOXA2, HOXA3, HOXA5 and HOXA7, which are considered 'anterior' genes, and HOXA9 and HOXA10, which are considered 'posterior' genes. Gene expression was normalized to GAPDH and is shown in arbitrary units in FIG. 29.

In the absence of retinoic acid signaling, SB/CHIR, but not CH BVSAF, induced low levels of anterior (FIG. 29*a,b*) and high levels of posterior (FIG. 29*c,d*) HOXA genes.

Retinoic acid signaling from d2-4 induced predominantly anterior HOXA genes irrespective of SB CHIR treatment (FIG. 29).

Combining EC23 with SB CHIR induced a balance of both anterior and posterior HOXA genes (FIG. 29).

Both $10^{-5}$ M and $10^{-7}$ M concentrations of EC23 were effective (FIG. 29).

A comparison of FIG. 16*h*, representing cells cultured in the absence of retinoic acid signaling, with FIG. 29, representing cells cultured in the presence of retinoic acid signaling, demonstrates that retinoic acid signaling improves the HOXA expression patterning of cells differentiated according to the procedure disclosed herein, thereby producing cells that replicate AGM HOXA expression patterning with greater fidelity.

Treating Acute Myeloid Leukaemia

Haematopoietic stem/progenitor cells produced according to the present disclosure will be administered to a subject diagnosed with acute myeloid leukaemia (AML) at a dose of $3\times10^6$ cells/kg who has undergone myeloablative therapy according to standard protocols prior to allogeneic HSC transplantation. Administration of the haematopoietic stem/progenitor cells will result in an equivalent or improved response in the subject.

Treating Acute Lymphocytic Leukaemia

Haematopoietic stem/progenitor cells produced according to the present disclosure will be administered to a subject diagnosed with acute lymphocytic leukaemia (ALL) at a dose of $3\times10^6$ cells/kg who has undergone myeloablative therapy according to standard protocols prior to allogeneic HSC transplantation. Administration of the haematopoietic stem/progenitor cells will result in an equivalent or improved response in the subject.

The invention claimed is:

1. A method for differentiating a pluripotent stem cell (PSC) into a definitive haematopoietic stem/progenitor cell, the method comprising increasing HOXA gene expression by culturing the PSC as an embryoid body in a medium and adding a WNT agonist and an ACTIVIN antagonist to the medium at about day 2 to day 4, wherein the medium further comprises a retinoid or retinoic acid analogue added to the medium from day 2 or day 3, and wherein increased HOXA gene expression is relative to a cell net cultured in the medium to which the WNT agonist and the ACTIVIN antagonist are not added.

2. The method of claim 1, wherein the HOXA gene is one or more of HOXA3, HOXA5, HOXA7, HOXA9, HOXA10, HOXA11, and HOXA13.

3. The method of claim 1, wherein the WNT agonist is CHIR99021.

4. The method of claim 3, wherein the medium added with WNT agonist and the Activin antagonist comprises 2-5 μM CHIR99021.

5. The method of claim 1, wherein the ACTIVIN antagonist is SB431542.

6. The method of claim 5, wherein the medium added with WNT agonist and the Activin antagonist comprises 2-5 μM SB431542.

7. The method of claim 1, wherein the medium comprises about 5-60 ng/ml BMP4, about 10-70 ng/ml vascular endothelial growth factor (VEGF), about 10-120 ng/mL SCF, about 1-30 ng/ml ACTIVIN A and about 1-20 ng/mL fibroblast growth factor 2 (FGF2).

8. The method of claim 7, further comprising replacing the medium with a medium comprising BMP4, VEGF, SCF, FGF2 and insulin-like growth factor 2 (IGF2) at about day 5, wherein the medium comprises about 5-60 ng/ml BMP4, about 10-70 ng/mL VEGF, about 10-120 ng/mL SCF, about 1-20 ng/mL FGF2, and about 20-50 ng/ml IGF2.

9. The method of claim 8, further comprising transferring the PSC to a culture surface comprising an extracellular matrix protein at about day 7 and culturing the PSC adherently in a medium comprising VEGF, SCF, FGF2, IGF2, interleukin 6 (IL-6), thrombopoietin (TPO), FLT3 receptor ligand (FLT3L), and interleukin 3 (IL-3) and/or erythropoietin (EPO), wherein the medium comprises about 10-70 ng/ml VEGF, about 10-120 ng/mL SCF, about 10-50 ng/ml IL-6, about 10-50 ng/ml TPO, about 1-70 ng/mL FLT3L, about 1-20 ng/ml FGF2 and about 20-50 ng/ml IGF2, and about 10-50 ng/mL IL-3 and/or about 1-10 U/mL EPO.

10. The method of claim 1, wherein the medium is Albumin Polyvinylalcohol Essential Lipids (APEL) medium.

11. The method of claim 1, wherein the definitive haematopoietic stem/progenitor cell is capable of producing a SOX17+ blood vessel cell or a RUNX1C+ blood cell.

12. The method of claim 1, wherein the pluripotent stem cell is an embryonic stem cell (ESC) or an induced PSC (iPSC).

13. The method of claim 1, wherein the PSC is human.

14. The method of claim 1, wherein the retinoid or retinoic acid analogue excludes all trans retinoic acid.

* * * * *

SEQUENCE LISTING

```
Sequence total quantity: 25
SEQ ID NO: 1            moltype = AA  length = 116
FEATURE                 Location/Qualifiers
REGION                  1..116
                        note = MISC_FEATURE - Human Activin A
source                  1..116
                        mol_type = protein
                        organism = Homo sapiens
SEQUENCE: 1
GLECDGKVNI CCKKQFFVSF KDIGWNDWII APSGYHANYC EGECPSHIAG TSGSSLSFHS  60
TVINHYRMRG HSPFANLKSC CVPTKLRPMS MLYYDDGQNI IKKDIQNMIV EECGCS      116

SEQ ID NO: 2            moltype = AA  length = 106
FEATURE                 Location/Qualifiers
```

```
REGION                1..106
                      note = MISC_FEATURE - Human BMP4
source                1..106
                      mol_type = protein
                      organism = Homo sapiens
SEQUENCE: 2
KKNKNCRRHS LYVDFSDVGW NDWIVAPPGY QAFYCHGDCP FPLADHLNST NHAIVQTLVN  60
SVNSSIPKAC CVPTELSAIS MLYLDEYDKV VLKNYQEMVV EGCGCR                 106

SEQ ID NO: 3          moltype = AA  length = 288
FEATURE               Location/Qualifiers
REGION                1..288
                      note = MISC_FEATURE - Human FGF2
source                1..288
                      mol_type = protein
                      organism = Homo sapiens
SEQUENCE: 3
MVGVGGGDVE DVTPRPGGCQ ISGRGARGCN GIPGAAAWEA ALPRRRPRRH PSVNPRSRAA  60
GSPRTRGRRT EERPSGSRLG DRGRGRALPG GRLGGRGRGR APERVGGRGR GRGTAAPRAA  120
PAARGSRPGP AGTMAAGSIT TLPALPEDGG SGAFPPGHFK DPKRLYCKNG GFFLRIHPDG  180
RVDGVREKSD PHIKLQLQAE ERGVVSIKGV CANRYLAMKE DGRLLASKCV TDECFFFERL  240
ESNNYNTYRS RKYTSWYVAL KRTGQYKLGS KTGPGQKAIL FLPMSAKS               288

SEQ ID NO: 4          moltype = AA  length = 165
FEATURE               Location/Qualifiers
REGION                1..165
                      note = MISC_FEATURE - Human vascular endothelial growth
                       factor (VEGF)
source                1..165
                      mol_type = protein
                      organism = Homo sapiens
SEQUENCE: 4
APMAEGGGQN HHEVVKFMDV YQRSYCHPIE TLVDIFQEYP DEIEYIFKPS CVPLMRCGGC  60
CNDEGLECVP TEESNITMQI MRIKPHQGQH IGEMSFLQHN KCECRPKKDR ARQENPCGPC  120
SERRKHLFVQ DPQTCKCSCK NTDSRCKARQ LELNERTCRC DKPRR                  165

SEQ ID NO: 5          moltype = AA  length = 165
FEATURE               Location/Qualifiers
REGION                1..165
                      note = MISC_FEATURE - human stem cell factor (SCF)
source                1..165
                      mol_type = protein
                      organism = Homo sapiens
SEQUENCE: 5
MEGICRNRVT NNVKDVTKLV ANLPKDYMIT LKYVPGMDVL PSHCWISEMV VQLSDSLTDL  60
LDKFSNISEG LSNYSIIDKL VNIVDDLVEC VKENSSKDLK KSFKSPEPRL FTPEEFFRIF  120
NRSIDAFKDF VVASETSDCV VSSTLSPEKD SRVSVTKPFM LPPVA                  165

SEQ ID NO: 6          moltype = AA  length = 67
FEATURE               Location/Qualifiers
REGION                1..67
                      note = MISC_FEATURE - Human insulin-like growth factor 2
                       (IGF2)
source                1..67
                      mol_type = protein
                      organism = Homo sapiens
SEQUENCE: 6
AYRPSETLCG GELVDTLQFV CGDRGFYFSR PASRVSRRSR GIVEECCFRS CDLALLETYC  60
ATPAKSE                                                            67

SEQ ID NO: 7          moltype = AA  length = 184
FEATURE               Location/Qualifiers
REGION                1..184
                      note = MISC_FEATURE - Human interleukin 6 (IL-6)
source                1..184
                      mol_type = protein
                      organism = Homo sapiens
SEQUENCE: 7
PVPPGEDSKD VAAPHRQPLT SSERIDKQIR YILDGISALR KETCNKSNMC ESSKEALAEN  60
NLNLPKMAEK DGCFQSGFNE ETCLVKIITG LLEFEVYLEY LQNRFESSEE QARAVQMSTK  120
VLIQFLQKKA KNLDAITTPD PTTNASLLTK LQAQNQWLQD MTTHLILRSF KEFLQSSLRA  180
LRQM                                                               184

SEQ ID NO: 8          moltype = AA  length = 174
FEATURE               Location/Qualifiers
REGION                1..174
                      note = MISC_FEATURE - Human thrombopoietin (TPO) comprising
                       the erythropoietin-likedomain of the full length TPO
                       protein
```

```
source                 1..174
                       mol_type = protein
                       organism = Homo sapiens
SEQUENCE: 8
SPAPPACDLR VLSKLLRDSH VLHSRLSQCP EVHPLPTPVL LPAVDFSLGE WKTQMEETKA  60
QDILGAVTLL LEGVMAARGQ LGPTCLSSLL GQLSGQVRLL LGALQSLLGT QLPPQGRTTA  120
HKDPNAIFLS FQHLLRGKVR FLMLVGGSTL CVRRAPPTTA VPSRTSLVLT LNEL        174

SEQ ID NO: 9           moltype = AA  length = 155
FEATURE                Location/Qualifiers
REGION                 1..155
                       note = MISC_FEATURE - Human FLT3 receptor ligand (FLT3L)
source                 1..155
                       mol_type = protein
                       organism = Homo sapiens
SEQUENCE: 9
TQDCSFQHSP ISSDFAVKIR ELSDYLLQDY PVTVASNLQD EELCGGLWRL VLAQRWMERL  60
KTVAGSKMQG LLERVNTEIH FVTKCAFQPP PSCLRFVQTN ISRLLQETSE QLVALKPWIT  120
RQNFSRCLEL QCQPDSSTLP PPWSPRPLEA TAPTA                             155

SEQ ID NO: 10          moltype = AA  length = 133
FEATURE                Location/Qualifiers
REGION                 1..133
                       note = MISC_FEATURE - Human interleukin 3 (IL 3)
source                 1..133
                       mol_type = protein
                       organism = Homo sapiens
SEQUENCE: 10
APMTQTTSLK TSWVNCSNMI DEIITHLKQP PLPLLDFNNL NGEDQDILME NNLRRPNLEA  60
FNRAVKSLQN ASAIESILKN LLPCLPLATA APTRHPIHIK DGDWNEFRRK LTFYLKTLEN  120
AQAQQTTLSL AIF                                                     133

SEQ ID NO: 11          moltype = AA  length = 166
FEATURE                Location/Qualifiers
REGION                 1..166
                       note = MISC_FEATURE - Human erythropoietin (EPO)
source                 1..166
                       mol_type = protein
                       organism = Homo sapiens
SEQUENCE: 11
APPRLICDSR VLERYLLEAK EAENITTGCA EHCSLNENIT VPDTKVNFYA WKRMEVGQQA  60
VEVWQGLALL SEAVLRGQAL LVNSSQPWEP LQLHVDKAVS GLRSLTTLLR ALGAQKEAIS  120
PPDAASAAPL RTITADTFRK LFRVYSNFLR GKLKLYTGEA CRTGDR                 166

SEQ ID NO: 12          moltype = AA  length = 128
FEATURE                Location/Qualifiers
REGION                 1..128
                       note = MISC_FEATURE - Human granulocyte-macrophage
                        colony-stimulating factor (GM-CSF
source                 1..128
                       mol_type = protein
                       organism = Homo sapiens
SEQUENCE: 12
MAPARSPSPS TQPWEHVNAI QEARRLLNLS RDTAAEMNET VEVISEMFDL QEPTCLQTRL  60
ELYKQGLRGS LTKLKGPLTM MASHYKQHCP PTPETSCATQ IITFESFKEN LKDFLLVIPF  120
DCWEPVQE                                                           128

SEQ ID NO: 13          moltype = AA  length = 25
FEATURE                Location/Qualifiers
REGION                 1..25
                       note = Synthetic construct
source                 1..25
                       mol_type = protein
                       organism = synthetic construct
SEQUENCE: 13
CCCAAATGCT TGAAAGATCA TATCC                                        25

SEQ ID NO: 14          moltype = AA  length = 25
FEATURE                Location/Qualifiers
REGION                 1..25
                       note = Synthetic construct
source                 1..25
                       mol_type = protein
                       organism = synthetic construct
SEQUENCE: 14
GTCGCCGTCC AGCTCGACCA GGATG                                        25

SEQ ID NO: 15          moltype = AA  length = 24
FEATURE                Location/Qualifiers
```

```
REGION                  1..24
                        note = Synthetic construct
source                  1..24
                        mol_type = protein
                        organism = synthetic construct
SEQUENCE: 15
CTCCGCATTG GTCTTGACCA ACTC                                          24

SEQ ID NO: 16           moltype = AA  length = 24
FEATURE                 Location/Qualifiers
REGION                  1..24
                        note = Synthetic construct
source                  1..24
                        mol_type = protein
                        organism = synthetic construct
SEQUENCE: 16
GCAGCTTTGT ACTTGGCAAT TCCC                                          24

SEQ ID NO: 17           moltype = AA  length = 33
FEATURE                 Location/Qualifiers
REGION                  1..33
                        note = Synthetic construct
source                  1..33
                        mol_type = protein
                        organism = synthetic construct
SEQUENCE: 17
TACGTCGACC ATCGCTTCCT CCTGAAAATG CAC                                33

SEQ ID NO: 18           moltype = AA  length = 24
FEATURE                 Location/Qualifiers
REGION                  1..24
                        note = Synthetic construct
source                  1..24
                        mol_type = protein
                        organism = synthetic construct
SEQUENCE: 18
TCTCACGCAC CGACTGAACA CTCC                                          24

SEQ ID NO: 19           moltype = AA  length = 24
FEATURE                 Location/Qualifiers
REGION                  1..24
                        note = Synthetic construct
source                  1..24
                        mol_type = protein
                        organism = synthetic construct
SEQUENCE: 19
CGGTGGGCTC TATGGCTTCT GAGG                                          24

SEQ ID NO: 20           moltype = AA  length = 23
FEATURE                 Location/Qualifiers
REGION                  1..23
                        note = Synthetic construct
source                  1..23
                        mol_type = protein
                        organism = synthetic construct
SEQUENCE: 20
CACACTGAAT GCAAACCACA GGG                                           23

SEQ ID NO: 21           moltype = AA  length = 20
FEATURE                 Location/Qualifiers
REGION                  1..20
                        note = MISC_FEATURE - Human Fujita a
source                  1..20
                        mol_type = protein
                        organism = Homo sapiens
SEQUENCE: 21
ACGTGTATGT TGGTCTCCCG                                               20

SEQ ID NO: 22           moltype = AA  length = 19
FEATURE                 Location/Qualifiers
REGION                  1..19
                        note = MISC_FEATURE - Human Fujita b
source                  1..19
                        mol_type = protein
                        organism = Homo sapiens
SEQUENCE: 22
AAGCGATGGC TTCAGACAG                                                19

SEQ ID NO: 23           moltype = AA  length = 17
```

-continued

```
FEATURE                Location/Qualifiers
REGION                 1..17
                       note = MISC_FEATURE - Human Fujita c
source                 1..17
                       mol_type = protein
                       organism = Homo sapiens
SEQUENCE: 23
TCACAGTGAC CAGAGTG                                                   17

SEQ ID NO: 24          moltype = AA  length = 24
FEATURE                Location/Qualifiers
REGION                 1..24
                       note = Synthetic construct
REGION                 1..24
                       note = MISC_FEATURE - fAML1a
source                 1..24
                       mol_type = protein
                       organism = synthetic construct
SEQUENCE: 24
TGTGGTCCTA TTTAAGCCAG CCCC                                           24

SEQ ID NO: 25          moltype = AA  length = 24
FEATURE                Location/Qualifiers
REGION                 1..24
                       note = Synthetic construct
REGION                 1..24
                       note = MISC_FEATURE - rAML1a
source                 1..24
                       mol_type = protein
                       organism = synthetic construct
SEQUENCE: 25
TCAGGCTGGG CACGACGAAT GCTC                                           24
```